United States Patent
Mantell et al.

(10) Patent No.: US 7,238,676 B2
(45) Date of Patent: *Jul. 3, 2007

(54) PURINE DERIVATIVES

(75) Inventors: Simon John Mantell, Sandwich (GB); Sandra Marina Monaghan, Sandwich (GB); Peter Thomas Stephenson, Sandwich (GB)

(73) Assignee: Pfizer Inc., Groton, CT (US)

(*) Notice: Subject to any disclaimer, the term of this patent is extended or adjusted under 35 U.S.C. 154(b) by 0 days.

This patent is subject to a terminal disclaimer.

(21) Appl. No.: 10/869,380

(22) Filed: Jun. 15, 2004

(65) Prior Publication Data

US 2004/0229838 A1 Nov. 18, 2004

Related U.S. Application Data

(62) Division of application No. 09/884,244, filed on Jun. 19, 2001, now Pat. No. 6,921,753.

(60) Provisional application No. 60/218,466, filed on Jul. 14, 2000.

(30) Foreign Application Priority Data

Jun. 27, 2000 (GB) ................................. 0015727.1

(51) Int. Cl.
*A61K 31/70* (2006.01)
*A61K 31/7076* (2006.01)
*C07H 19/167* (2006.01)

(52) U.S. Cl. .................... 514/46; 514/45; 514/825; 514/861; 536/27.6; 536/27.61; 536/27.62

(58) Field of Classification Search .................. 514/46, 514/825, 826, 861, 866, 45; 536/27.6, 27.61, 536/27.62

See application file for complete search history.

(56) References Cited

U.S. PATENT DOCUMENTS 6,350,735 B1 * 2/2002 Monaghan .................... 514/46

FOREIGN PATENT DOCUMENTS

| WO | WO 8803147 | 5/1988 |
|---|---|---|
| WO | WO 9111172 | 8/1991 |
| WO | WO 9402518 | 2/1994 |
| WO | WO 9407905 | 4/1994 |
| WO | WO 9602553 | 2/1996 |
| WO | WO 9855148 | 12/1998 |
| WO | WO 9924451 | 5/1999 |
| WO | WO 9934804 | 7/1999 |
| WO | WO 0023457 | 4/2000 |
| WO | WO 0077018 | 12/2000 |
| WO | WO 0127130 | 4/2001 |
| WO | WO 0127131 | 4/2001 |
| WO | WO 0160835 | 8/2001 |
| WO | WO 0194368 | 12/2001 |

OTHER PUBLICATIONS

Olsson et al., J. Med. Chem. 1986, vol. 29, 1683-1689.*
Jacobson, Kenneth et al., J. of Medicinal Chem. 1992, 35(3), pp. 407-422.
Olsson, R. A. et al., J. of Medicinal Chem., 1986, 29(9), pp. 1683-1689.
Berge, et al., J. Pharm Sci, 66, pp. 1-19, 1977.
J. Med. Chem. 41, pp. 3174-3185, 1998.
J. Amer. Chem. Soc, 105(10), pp. 3136-3147.
J. Med. Chem, 31(7), pp. 1282-1285, 1988.
J. Org. Chem. 36(23), pp. 3539-3541, 1971.
J. Med. Chem. 12(1), pp. 9-15, 1969.
J. Amer. Chem. Soc., 80, pp. 5168-5173, 1958.
Mambula et al., Infection and Immunity, vol. 68, No. 11, pp. 6257-6264 (Nov. 2000).
Kelly et al., The American Society for Clinical Investigation, Inc., vol. 93, pp. 1257-1265 (Mar. 1994).

* cited by examiner

*Primary Examiner*—Shaojia Anna Jiang
*Assistant Examiner*—Michael C. Henry
(74) *Attorney, Agent, or Firm*—Philip B. Polster, II

(57) ABSTRACT

The present invention relates to compounds of the formula

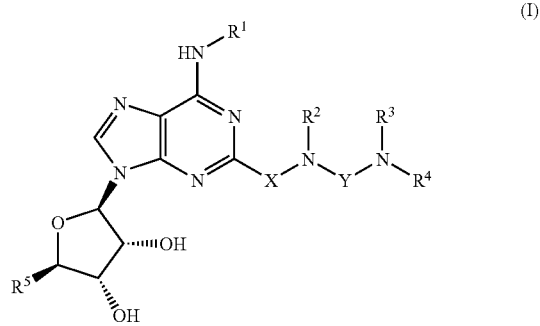

and pharmaceutically acceptable salts and solvates thereof, to processes for the preparation of, intermediates used in the preparation of, and compositions containing such compounds and the uses of such compounds as adenosine A2a receptor agonists.

4 Claims, No Drawings

PURINE DERIVATIVES

CROSS REFERENCE TO RELATED APPLICATIONS

This application is a divisional of U.S. patent application Ser. No. 09/884,244, filed Jun. 19, 2001 now U.S. Pat. No. 6,921,753, which claims the benefit of priority of Great Britain Provisional Patent Application No. 0015727.1, filed Jun. 27, 2000 and to U.S. Provisional Patent Application No. 60/218,466, filed Jul. 14, 2000, all of which are incorporated herein by reference in their entirety.

This invention relates to purine derivatives. More particularly, this invention relates to 2-aminoalkyl-9-(tetrahydro-2-furanyl)-9H-purine derivatives and to processes for the preparation of, intermediates used in the preparation of, compositions containing and the uses of, such derivatives.

These derivatives are selective, functional agonists of the human adenosine A2a receptor and may be used as anti-inflammatory agents in the treatment of, inter alia, diseases of the respiratory tract.

Adenosine is a ubiquitous molecule having a central role in mammalian intermediary metabolism. Independently, adenosine acts on multiple surface receptors to produce a variety of responses. Adenosine receptor classification has revealed the presence of at least four subtypes: A1, A2a, A2b and A3. Stimulation of adenosine A2 receptors on the surface of human neutrophils has been reported to potently inhibit a range of neutrophil functions. Activated neutrophils can damage lung tissue by release of reactive oxygen species, for example, superoxide anion radicals ($O_2^-$.), and granule products, for example, human neutrophil elastase (HNE), amongst other inflammatory mediators. In addition, activated neutrophils perform both de novo synthesis and release of arachidonate products such as leukotriene $B_4$ ($LTB_4$). $LTB_4$ is a potent chemo-attractant that recruits additional neutrophils to the inflammatory focus, whereas released $O_2^-$. and HNE adversely affect the pulmonary extracellular matrix. The A2 receptor subtype mediating many of these responses ($O_2^-$. and LTB4/HNE release and cell adhesion) is established as A2a. The A2 subtype (A2a or A2b) mediating the other effects remains to be established.

Selective agonist activity at the A2a receptor is considered to offer greater therapeutic benefit than the use of non-selective adenosine receptor agonists because interaction with other subtypes is associated with detrimental effects in the lung in animal models and human tissue studies. For example, asthmatics, but not non-asthmatics, bronchoconstrict when challenged with inhaled adenosine. This response is at least in part due to the activation of the A1 receptor subtype. Activation of A1 receptors also promotes neutrophil chemotaxis and adherence to endothelial cells, thus promoting lung injury. Furthermore, many patients with respiratory disease will be co-prescribed $\beta_2$-agonists, and negative interaction has been shown in animal studies between isoprenaline and adenosine receptors negatively coupled to adenylate cyclase. Degranulation of human mast cells is promoted by activation of adenosine A2b receptors, thus selectivity over the A2b receptor is also advantageous.

We have now surprisingly found the present purine derivatives inhibit neutrophil function and are selective agonists of the adenosine A2a receptor. They may also have antagonist activity at the adenosine A3 receptor. The present compounds may be used to treat any disease for which an adenosine A2a receptor agonist is indicated. They can be used to treat a disease where leukocyte (e.g. neutrophil, eosinophil, basophil, lymphocyte, macrophage)-induced tissue damage is implicated. They are useful as anti-inflammatory agents in the treatment of diseases of the respiratory tract such as adult respiratory distress syndrome (ARDS), bronchitis, chronic bronchitis, chronic obstructive pulmonary disease, cystic fibrosis, asthma, emphysema, bronchiectasis, chronic sinusitis and rhinitis. The present compounds may also be used in the treatment of septic shock, male erectile dysfunction, hypertension, stroke, epilepsy, cerebral ischaemia, peripheral vascular disease, post-ischaemic reperfusion injury, diabetes, rheumatoid arthritis, multiple sclerosis, psoriasis, dermatitis, allergic dermatitis, eczema, ulcerative colitis, Crohns disease, inflammatory bowel disease, *Heliobacter pylori* gastritis, non-*Heliobacter pylori* gastritis, non-steroidal anti-inflammatory drug-induced damage to the gastrointestinal tract or a psychotic disorder, or for wound healing.

Accordingly, the present invention provides a compound of the formula

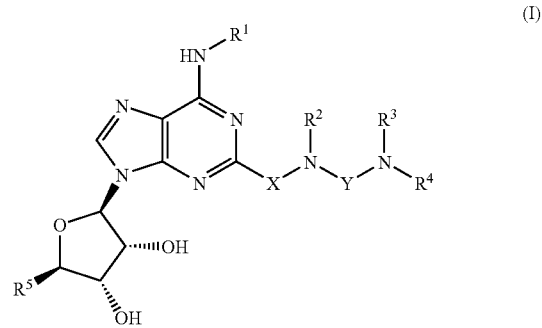

or a pharmaceutically acceptable salt or solvate thereof, wherein $R^1$ is (i) H, (ii) $C_1$–$C_6$ alkyl optionally substituted by 1 or 2 substituents each independently selected from phenyl, naphthyl and fluorenyl, said phenyl, naphthyl and fluorenyl being optionally substituted by $C_1$–$C_6$ alkyl, $C_1$–$C_6$ alkoxy, halo or cyano, or (iii) fluorenyl;

$R^2$ is H or $C_1$–$C_6$ alkyl;

either, $R^3$ and $R^4$, taken together with the nitrogen atom to which they are attached, represent azetidinyl, pyrrolidinyl, piperidinyl, piperazinyl, homopiperidinyl or homopiperazinyl, each being optionally substituted on a ring nitrogen or carbon atom by $C_1$–$C_6$ alkyl or $C_3$–$C_8$ cycloalkyl and optionally substituted on a ring carbon atom not adjacent to a ring nitrogen atom by —$NR^6R^7$ or —$OR^9$, or, $R^3$ is H, $C_1$–$C_6$ alkyl, $C_3$–$C_8$ cycloalkyl or benzyl, said $C_1$–$C_6$ alkyl being optionally substituted by $C_3$–$C_8$ cycloalkyl, and $R^4$ is (a) $C_1$–$C_6$ alkyl, $C_3$–$C_8$ cycloalkyl or $R^{15}$, said $C_1$–$C_6$ alkyl being optionally substituted by $R^{15}$; or (b) —($C_2$–$C_6$ alkylene)-$R^8$, or (c) —($C_1$–$C_6$ alkylene)-$R^{13}$;

$R^5$ is —$CH_2OH$ or —$CONR^{14}R^{14}$;

$R^6$ and $R^7$ are either each independently H or $C_1$–$C_6$ alkyl or, taken together with the nitrogen atom to which they are attached, represent azetidinyl, pyrrolidinyl or piperidinyl, said azetidinyl, pyrrolidinyl and piperidinyl being optionally substituted by $C_1$–$C_6$ alkyl;

$R^8$ is (i) azetidin-1-yl, pyrrolidin-1-yl, piperidin-1-yl, morpholin-4-yl, piperazin-1-yl, homopiperidin-1-yl, homopiperazin-1-yl or tetrahydroisoquinolin-1-yl, each being optionally substituted on a ring carbon atom by $C_1$–$C_6$ alkyl, $C_3$–$C_8$ cycloalkyl, phenyl, $C_1$–$C_6$ alkoxy-($C_1$–$C_6$)-alkyl, $R^9R^9N$—($C_1$–$C_6$)-alkyl, fluoro-($C_1$–$C_6$)-alkyl, —$CONR^9R^9$, —$COOR^9$ or $C_2$–$C_5$ alkanoyl, optionally substituted on a ring carbon atom not adjacent to a ring nitrogen atom by fluoro-($C_1$–$C_6$)-alkoxy, halo, —$OR^9$, cyano, —$S(O)_mR^{10}$, —$NR^9R^9$, —$SO_2NR^9R^9$, —$NR^9COR^{10}$ or —$NR^9SO_2R^{10}$ and optionally benzo-fused, and said piperazin-1-yl and homopiperazin-1-yl being optionally substituted on the ring nitrogen atom not attached to the $C_2$–$C_6$ alkylene group by $C_1$–$C_6$ alkyl, phenyl, $C_1$–$C_6$ alkoxy-($C_2$–$C_6$)-alkyl, $R^9R^9N$—($C_2$–$C_6$)-alkyl, fluoro-($C_1$–$C_6$)-alkyl, $C_2$–$C_5$ alkanoyl, —$COOR^{10}$, $C_3$–$C_8$ cycloalkyl, —$SO_2R^{10}$, —$SO_2NR^9R^9$ or —$CONR^9R^9$, or (ii) —$NR^{11}R^{12}$;

$R^9$ is H, $C_1$–$C_6$ alkyl, $C_3$–$C_8$ cycloalkyl or phenyl;

$R^{10}$ is $C_1$–$C_6$ alkyl, $C_3$–$C_8$ cycloalkyl or phenyl;

$R^{11}$ is $C_1$–$C_6$ alkyl, $C_3$–$C_8$ cycloalkyl or benzyl;

$R^{12}$ is $C_1$–$C_6$ alkyl, $C_3$–$C_8$ cycloalkyl, phenyl, benzyl, fluoro-($C_1$–$C_6$)-alkyl, —$CONR^9R^9$, —$COOR^{10}$, —$COR^{10}$, —$SO_2R^{10}$ or —$SO_2NR^9R^9$, said $C_1$–$C_6$ alkyl being optionally substituted by phenyl;

$R^{13}$ is phenyl, pyridin-2-yl, pyridin-3-yl or pyridin-4-yl, each being optionally substituted by $C_1$–$C_6$ alkyl, $C_1$–$C_6$ alkoxy, halo or cyano;

$R^{14}$ is H or $C_1$–$C_6$ alkyl optionally substituted by cyclopropyl;

$R^{15}$ is azetidin-3-yl, pyrrolidin-3-yl, piperidin-3-yl, piperidin-4-yl, homopiperidin-3-yl or homopiperidin-4-yl, each being optionally substituted by $R^{13}$, $C_1$–$C_6$ alkyl, $C_3$–$C_8$ cycloalkyl or benzyl;

m is 0, 1 or 2;

X is —$CH_2$— or —$CH_2CH_2$—; and

Y is CO, CS, $SO_2$ or C=N(CN).

In the above definitions, halo means fluoro, chloro, bromo or iodo and alkyl, alkylene, alkarioyl and alkoxy groups containing the requisite number of carbon atoms can be unbranched or branched chain. Examples of alkyl include methyl, ethyl, n-propyl, i-propyl, n-butyl, i-butyl, sec-butyl and t-butyl. Examples of alkoxy include methoxy, ethoxy, n-propoxy, i-propoxy, n-butoxy, i-butoxy, sec-butoxy and t-butoxy. Examples of alkanoyl include acetyl and propanoyl. Examples of alkylene include methylene, 1,1-ethylene, 1,2-ethylene, 1,1-propylene, 1,2-propylene, 1,3-propylene and 2,2-propylene. Examples of cycloalkyl include cyclopropyl, cyclobutyl, cyclopentyl, cyclohexyl and cycloheptyl.

The pharmaceutically acceptable salts of the compounds of the formula (I) include the acid addition and the base salts thereof.

Suitable acid addition salts are formed from acids which form non-toxic salts and examples are the hydrochloride, hydrobromide, hydroiodide, sulphate, bisulphate, nitrate, phosphate, hydrogen phosphate, acetate, maleate, fumarate, lactate, tartrate, citrate, gluconate, succinate, saccharate, benzoate, methanesulphonate, ethanesulphonate, benzenesulphonate, para-toluenesulphonate and pamoate salts.

Suitable base salts are formed from bases which form non-toxic salts and examples are the sodium, potassium, aluminium, calcium, magnesium, zinc and diethanolamine salts.

For a review on suitable salts see Berge et al, *J. Pharm. Sci.*, 66, 1–19, 1977.

The pharmaceutically acceptable solvates of the compounds of the formula (I) include the hydrates thereof.

Also included within the present scope of the compounds of the formula (I) are polymorphs thereof.

A compound of the formula (I) may contain one or more additional asymmetric carbon atoms and therefore exist in two or more stereoisomeric forms. The present invention includes the individual stereoisomers of the compounds of the formula (I) together with, where appropriate, the individual tautomers thereof, and mixtures thereof.

Separation of diastereoisomers may be achieved by conventional techniques, e.g. by fractional crystallisation, chromatography or H.P.L.C. of a stereoisomeric mixture of a compound of the formula (I) or a suitable salt or derivative thereof. An individual enantiomer of a compound of the formula (I) may also be prepared from a corresponding optically pure intermediate or by resolution, such as by H.P.L.C. of the corresponding racemate using a suitable chiral support or by fractional crystallisation of the diastereoisomeric salts formed by reaction of the corresponding racemate with a suitable optically active acid or base, as appropriate.

Preferably, $R^1$ is $C_1$–$C_6$ alkyl optionally substituted by 1 or 2 substituents each independently selected from phenyl, naphthyl and fluorenyl, said phenyl, naphthyl and fluorenyl being optionally substituted by $C_1$–$C_6$ alkyl, $C_1$–$C_6$ alkoxy, halo or cyano.

Preferably, $R^1$ is $C_1$–$C_6$ alkyl substituted by 1 or 2 substituents each independently selected from phenyl, naphthyl and fluorenyl, said phenyl, naphthyl and fluorenyl being optionally substituted by $C_1$–$C_6$ alkyl, $C_1$–$C_6$ alkoxy, halo or cyano.

Preferably, $R^1$ is $C_1$–$C_4$ alkyl substituted by 1 or 2 substituents each independently selected from phenyl, naphthyl and fluorenyl, said phenyl, naphthyl and fluorenyl being optionally substituted by $C_1$–$C_6$ alkyl, $C_1$–$C_6$ alkoxy, halo or cyano.

Preferably, $R^1$ is methyl or ethyl substituted by 1 or 2 substituents each independently selected from phenyl, naphthyl and fluorenyl, said phenyl, naphthyl and fluorenyl being optionally substituted by $C_1$–$C_6$ alkyl, $C_1$–$C_6$ alkoxy, halo or cyano.

Preferably, $R^1$ is methyl or ethyl substituted by 1 or 2 substituents each independently selected from phenyl, naphthyl and fluorenyl, said phenyl, naphthyl and fluorenyl being optionally substituted by $C_1$–$C_6$ alkyl or halo.

Preferably, $R^1$ is diphenylethyl, di(chlorophenyl)ethyl, di(methylphenyl)ethyl, naphthylmethyl or fluorenylmethyl.

Preferably, $R^1$ is 2,2-diphenyleth-1-yl, 2,2-di(4-chlorophenyl)eth-1-yl, 2,2-di(3-chlorophenyl)eth-1-yl, 2,2-di(4-methylphenyl)eth-1-yl, 2,2-di(3-methylphenyl)eth-1-yl, naphth-1-ylmethyl or fluoren-9-ylmethyl.

Preferably, $R^1$ is 2,2-diphenyleth-1-yl.

Preferably, $R^2$ is H or $C_1$–$C_4$ alkyl.

Preferably, $R^2$ is H or $C_1$–$C_2$ alkyl.

Preferably, $R^2$ is H or methyl.

Preferably, $R^2$ is H.

Preferably $R^3$ and $R^4$ do not form part of the same cyclic structure.

Preferably, $R^3$ is H or $C_1$–$C_6$ alkyl.

Preferably, $R^3$ is H or $C_1$–$C_4$ alkyl.

Preferably, $R^3$ is H or $C_1$–$C_2$ alkyl.

Preferably, $R^3$ is H or methyl.

Preferably, $R^3$ is H.

Preferably, $R^4$ is (a) $C_1$–$C_4$ alkyl substituted by —$R^{15}$, $C_3$–$C_6$ cycloalkyl or —$R^{15}$; or (b) —($C_2$–$C_4$ alkylene)—$R^8$, or (c) —($C_1$–$C_4$ alkylene)—$R^{13}$.

Preferably, $R^4$ is (a) $C_1$–$C_2$ alkyl substituted by —$R^{15}$, $C_5$–$C_6$ cycloalkyl or —$R^{15}$; or (b) —(ethylene)—$R^8$, or (c) —($C_1$–$C_2$ alkylene)—$R^{13}$.

Preferably, $R^4$ is —$CH_2R^{15}$, cyclohexyl, —$R^{15}$, —$CH_2CH_2R^8$, —$CH_2R^{13}$ or —$CH_2CH_2R^{13}$.

Preferably, $R^4$ is 2-diisopropylaminoeth-1-yl or 2-piperidin-1-yleth-1-yl.

Preferably, $R^5$ is —$CH_2OH$ or —$CONH(C_1$–$C_6$ alkyl).

Preferably, $R^5$ is —$CH_2OH$ or —$CONH(C_1$–$C_4$ alkyl).

Preferably, $R^5$ is —$CH_2OH$ or —$CONH(C_1$–$C_2$ alkyl).

Preferably, $R^5$ is —$CH_2OH$ or —$CONHCH_2CH_3$.

Preferably, $R^8$ is (i) piperidin-1-yl, optionally substituted on a ring carbon atom by $C_1$–$C_6$ alkyl, $C_3$–$C_8$ cycloalkyl, phenyl, $C_1$–$C_6$ alkoxy-($C_1$–$C_6$)-alkyl, $R^9R^9N$—($C_1$–$C_6$)-alkyl, fluoro-($C_1$–$C_6$)-alkyl, —$CONR^9R^9$, —$COOR^9$ or $C_2$–$C_5$ alkanoyl, optionally substituted on a ring carbon atom not adjacent to a ring nitrogen atom by fluoro-($C_1$–$C_6$)-alkoxy, halo, —$OR^9$, cyano, —$S(O)_mR^{10}$, —$NR^9R^9$, —$SO_2NR^9R^9$, —$NR^9COR^{10}$ or —$NR^9SO_2R^{10}$ and optionally benzo-fused, or (ii) —$NR^{11}R^{12}$.

Preferably, $R^8$ is (i) piperidin-1-yl, optionally substituted on a ring carbon atom by $C_1$–$C_6$ alkyl and optionally benzo-fused, or (ii) —$NR^{11}R^{12}$.

Preferably, $R^8$ is (i) piperidin-1-yl, optionally substituted on a ring carbon atom by $C_1$–$C_3$ alkyl and optionally benzo-fused, or (ii) —$NR^{11}R^{12}$.

Preferably, $R^8$ is (i) piperidin-1-yl, optionally substituted on a ring carbon atom by methyl or propyl and optionally benzo-fused, or (ii) —$NR^{11}R^{12}$.

Preferably, $R^8$ is piperidin-1-yl, 4-(2-propyl)piperidin-1-yl, 2,2,6,6-tetramethylpiperidin-1-yl, 1,2,3,4-tetrahydroisoquinolin-2-yl or —$NR^{11}R^{12}$.

Preferably, $R^{11}$ is $C_1$–$C_6$ alkyl or $C_3$–$C_8$ cycloalkyl.

Preferably, $R^{11}$ is $C_1$–$C_5$ alkyl or $C_3$–$C_6$ cycloalkyl.

Preferably, $R^{11}$ is propyl, butyl, pentyl, cyclohexyl or cyclopentyl.

Preferably, $R^{11}$ is —$CH(CH_3)_2$, —$CH_2CH_2CH_2CH_3$, —$CH_2CH(CH_3)_2$, —$C(CH_3)_3$, —$CH(CH_2CH_3)_2$, cyclohexyl or cyclopentyl.

Preferably, $R^{12}$ is $C_1$–$C_6$ alkyl, $C_3$–$C_8$ cycloalkyl, —$COR^{10}$ or —$SO_2R^{10}$ said $C_1$–$C_6$ alkyl being optionally substituted by phenyl.

Preferably, $R^{12}$ is $C_1$–$C_5$ alkyl, $C_3$–$C_6$ cycloalkyl, —$COR^{10}$ or —$SO_2R^{10}$ said $C_1$–$C_6$ alkyl being optionally substituted by phenyl.

Preferably, $R^{12}$ is propyl, butyl, pentyl, cyclohexyl, cyclopentyl, phenylbutyl, —COPh or —$SO_2$Ph.

Preferably, $R^{12}$ is —$CH(CH_3)_2$, —$CH_2CH_2CH_2CH_3$, —$CH_2CH(CH_3)_2$, —$C(CH_3)_3$, —$CH(CH_2CH_3)_2$, —$C(CH_3)_2$Ph, —$SO_2$Ph, —COPh, cyclohexyl or cyclopentyl.

Preferably, $R^{13}$ is phenyl or pyridin-2-yl, each being optionally substituted by $C_1$–$C_6$ alkyl, $C_1$–$C_6$ alkoxy, halo or cyano.

Preferably, $R^{13}$ is phenyl or pyridin-2-yl.

Preferably, $R^{15}$ is pyrrolidin-3-yl or piperidin-4-yl, each being optionally substituted by $R^{13}$, $C_1$–$C_6$ alkyl, $C_3$–$C_8$ cycloalkyl or benzyl.

Preferably, $R^{15}$ is pyrrolidin-3-yl or piperidin-4-yl, each being optionally substituted by $R^{13}$ or benzyl.

Preferably, $R^{15}$ is 1-benzyl-piperidin-4-yl, (1-benzyl-piperidin-4-yl)methyl, 1-(2-pyridinyl)piperidin-4-yl, or 1-benzyl-pyrrolidin-3-yl.

Preferably, X is —$CH_2$—.

Preferably, Y is CO or C=N(CN).

Preferably, Y is CO.

Preferred individual compounds of the formula (I) include Examples 1–40 listed below and pharmaceutically acceptable salts and solvates thereof.

All of the compounds of the formula (I) can be prepared by conventional routes such as by the procedures described in the general methods presented below or by the specific methods described in the Examples section, or by similar methods thereto. The present invention also encompasses any one or more of these processes for preparing the compounds of formula (I), in addition to any novel intermediates used therein.

In the following general methods, $R^1$, $R^2$, $R^3$, $R^4$, $R^5$, X and Y are as previously defined for a compound of the formula (I) unless otherwise stated.

1. Compounds of the formula (I) in which $R^5$ is —$CONR^{14}R^{14}$ may be prepared by the deprotection of a compound of the formula

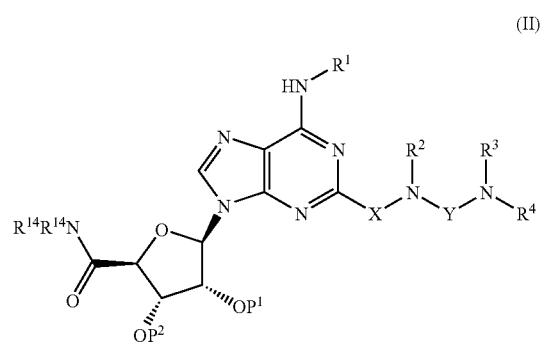

(II)

wherein $P^1$ and $P^2$ are suitable protecting groups which may be the same or different and may optionally form part of the same protecting group. Compounds of the formula (I) in which $R^5$ is —$CH_2OH$ may be prepared by the deprotection of a compound of the formula

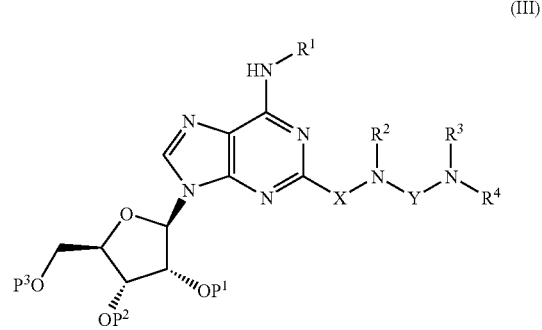

(III)

wherein $P^1$, $P^2$ and $P^3$ are suitable protecting groups which may be the same or different, $P^1$ and $P^2$ optionally forming part of the same protecting group. When deprotecting a compound of the formula (II) or a compound of the formula (III), the relevant protecting groups may be removed separately, progressing through one or more semi-protected intermediates, or together, or in any combination. Examples of suitable protecting groups will be apparent to the skilled person [see, for instance, 'Protecting groups in Organic Synthesis (Second Edition)', Theodora W. Green and Peter G. M. Wuts, John Wiley and Sons, 1991]. Preferred individual protecting groups are alkanoyl and aroyl. Preferred protecting groups where $P^1$ and $P^2$ form part of the same protecting group are where $P^1$ and $P^2$ taken together are $C_1$-$C_6$ alkylene. Particularly preferred individual protecting groups are acetyl and benzoyl. A particularly preferred protecting group where $P^1$ and $P^2$ form part of the same protecting group is where $P^1$ and $P^2$ taken together are dimethylmethylene. Suitable conditions for the deprotection are well known in the art [see, for instance, 'Protecting groups in Organic Synthesis (Second Edition)', Theodora W. Green and Peter G. M. Wuts, John Wiley and Sons, 1991]. In a typical procedure, a solution of a compound of the formula (III), wherein $P^1$, $P^2$ and $P^3$ are each acetyl, in a suitable solvent, such as methanol, is treated with a nucleophilic reagent, such as ammonia or a primary amine, or a base such as potassium carbonate, typically at room temperature. In another typical procedure, a solution of a compound of the formula (II), wherein $P^1$ and $P^2$ are each benzoyl, in a suitable solvent, such as methanol, is treated with a nucleophilic reagent, such as ammonia or a primary amine, or a base such as potassium carbonate, typically at a temperature from room temperature to 60° C.

Compounds of the formula (II) in which X is —$CH_2$— (i.e. compounds of the formula (IIA)) and compounds of the formula (III) in which X is —$CH_2$— (i.e. compounds of the formula (IIIA)) may be prepared according to the route shown in Scheme 1 wherein $P^4$ represents a suitable protecting group.

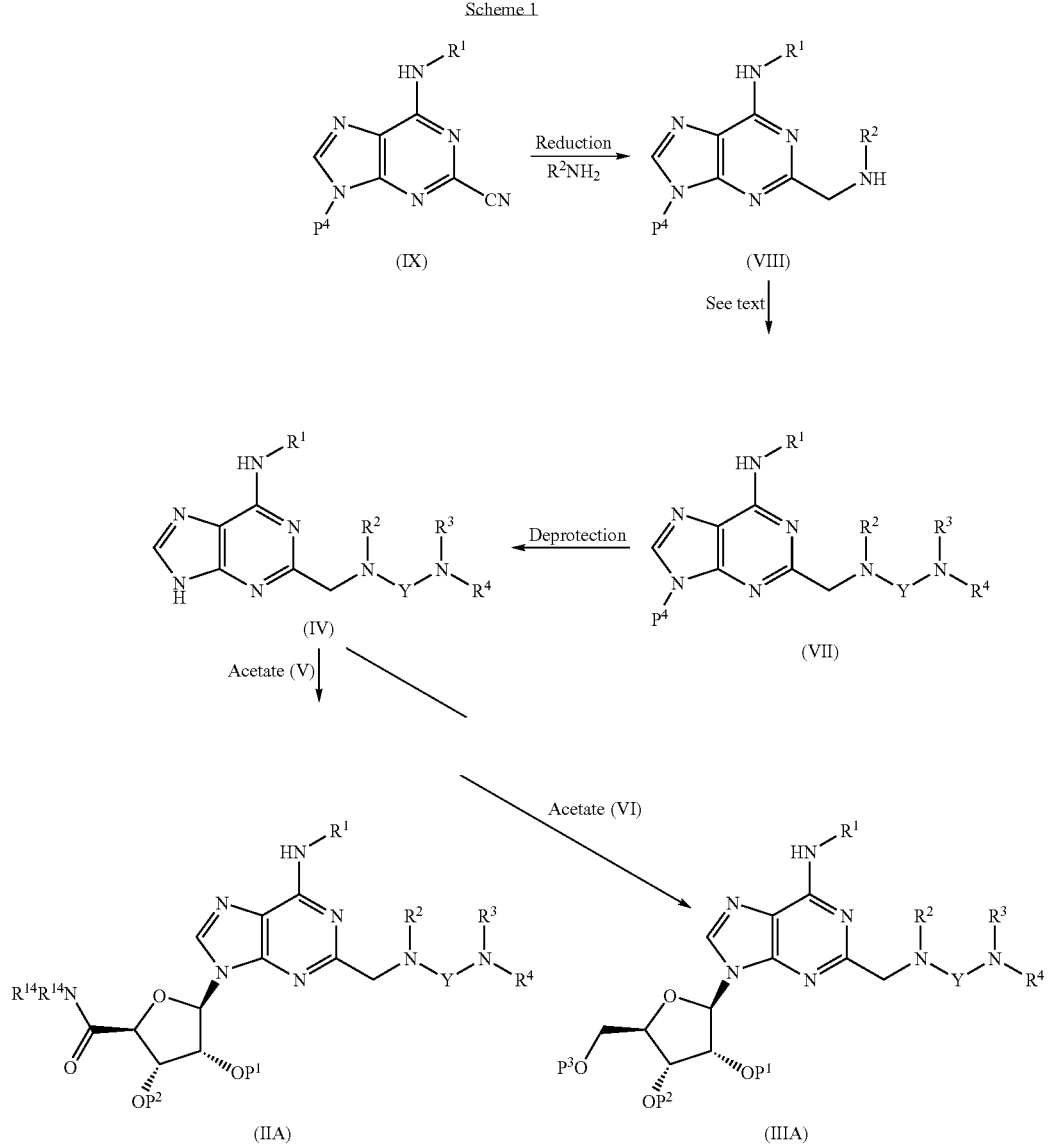

As shown in Scheme 1, compounds of the formula (IIA) may be prepared by the reaction of a compound of the formula

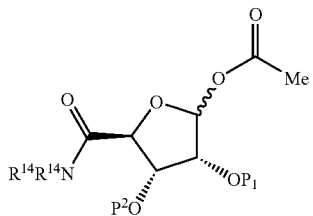

(V)

(in which $P^1$ and $P^2$ are as defined above) with trimethylsilyl trifluoromethanesulfonate and a compound of the formula (IV) which has been derivatised with N,O-bis(trimethylsilyl)acetamide. In a typical procedure, the compound of the formula (IV) is heated in the presence of a suitable solvent, such as 1,1,1-trichloroethane, with N,O-bis(trimethylsilyl)acetamide at an elevated temperature, preferably at about 50° C. The mixture is then allowed to cool and the solvent is evaporated. A solution of the residue in a suitable solvent, such as toluene, is treated with the compound of the formula (V) and trimethylsilyl trifluoromethanesulfonate and the mixture is heated, preferably under reflux, under a nitrogen atmosphere, to give the compound of the formula (IIA).

Compounds of the formula (IIIA) may be prepared by the reaction of a compound of the formula

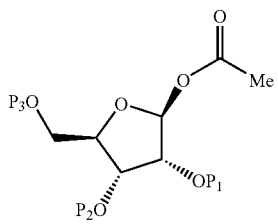

(VI)

(in which $P^1$, $P^2$ and $P^3$ are as defined above) with trimethylsilyl trifluoromethanesulfonate and a compound of the formula (IV) which has been derivatised with N,O-bis(trimethylsilyl)acetamide. In a typical procedure, the compound of the formula (IV) is heated in the presence of a suitable solvent, such as 1,1,1-trichloroethane, with N,O-bis(trimethylsilyl)acetamide at an elevated temperature, preferably at 50° C. The mixture is then allowed to cool and the solvent is removed. A solution of the residue in a suitable solvent such as toluene is treated with the compound of the formula (VI) and trimethylsilyl trifluoromethanesulfonate and the mixture is heated, preferably under reflux, under a nitrogen atmosphere, to give the compound of the formula (IIIA).

Compounds of the formula (IV) may be prepared by the deprotection of a compound of the formula (VII) wherein $P^4$ is a suitable protecting group. Examples of suitable protecting groups will be apparent to the skilled person [see, for instance, 'Protecting groups in Organic Synthesis (Second Edition)', Theodora W. Green and Peter G. M. Wuts, John Wiley and Sons, 1991]. A preferred protecting group is tetrahydropyran-2-yl. Suitable conditions for the deprotection are well known in the art [see, for instance, 'Protecting groups in Organic Synthesis (Second Edition)', Theodora W. Green and Peter G. M. Wuts, John Wiley and Sons, 1991]. In a typical procedure, where $P^4$ is tetrahydropyran-2-yl, the protecting group is removed by treating a solution of the compound of the formula (VII) in a suitable solvent, such as methanol, with an acid such as hydrochloric acid, preferably 2M aqueous hydrochloric acid.

Compounds of the formula (VII) in which Y is CO may be prepared by the reaction of a compound of the formula

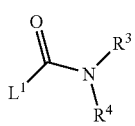

(X)

in which $L^1$ is a suitable leaving group, with a compound of the formula (VIII) in a suitable solvent, such as a mixture of toluene and isopropanol, typically at an elevated temperature, preferably under reflux. The leaving group $L^1$ is preferably halo (e.g. chloro) or imidazol-1-yl, most preferably imidazol-1-yl. Compounds of the formula (X) wherein $L^1$ is imidazol-1-yl may be prepared by the reaction of a compound of the formula $R^3R^4NH$ (XI)

with 1,1'-carbonyldiimidazole. In a typical reaction a compound of the formula (XI) is added to a solution of 1,1'-carbonyldiimidazole in a suitable solvent such as dichloromethane. Compounds of the formula (XI) are either commercially available or may be prepared by standard techniques well known to persons skilled in the art. Other compounds of the formula (X) are either commercially available or easily prepared by methods well known to the person skilled in the art.

Compounds of the formula (VII) in which Y is CO may also be prepared by the reaction of a compound of the formula (VIII) with a compound of the formula $L^2COL^3$ (XII)

in which $L^2$ and $L^3$ are suitable leaving groups, to form an intermediate of the formula

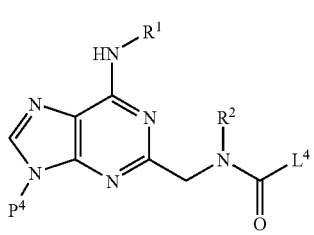

(XIII)

in which $L^4$ represents either of the leaving groups $L^2$ or $L^3$ and $P^4$ is as defined above, followed by the addition of a compound of the formula (XI) to the reaction mixture. Preferably, $L^2$ and $L^3$ are each halo or imidazol-1-yl. Most preferably, $L^2$ and $L^3$ are each imidazol-1-yl. In a typical example, where $L^2$ and $L^3$ are each imidazol-1-yl, a solution of the compound of the formula (VIII) in a suitable solvent, such as dichloromethane, is treated with 1,1'-carbonyldiimidazole. The reaction mixture is stirred, preferably at room temperature, until thin layer chromatography (TLC) indicates a substantially complete reaction has occurred and then a compound of the formula (XI) is added to give the compound of the formula (VII).

Compounds of the formula (VII) in which Y is CS may be prepared by the reaction of a compound of the formula

in which $L^5$ and $L^6$ are suitable leaving groups, with a compound of the formula (VIII), to form an intermediate of the formula

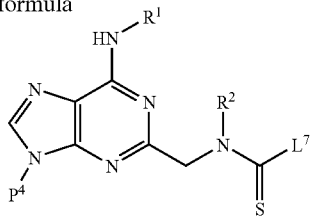

in which $L^7$ represents either of the leaving groups $L^5$ or $L^6$, followed by the addition of a compound of the formula (XI). The leaving groups $L^5$ and $L^6$ may be the same or different and are typically selected from —S(C$_1$–C$_6$ alkyl) or imidazol-1-yl. Preferably, $L^5$ and $L^6$ are each methylthio or imidazol-1-yl. In a typical procedure, a solution of the compound of the formula (XIV) in a suitable solvent, such as ethanol, is treated with the compound of the formula (VII), preferably at an elevated temperature, most preferably under reflux. When analysis by thin layer chromatography shows that a substantially complete reaction has occurred, a compound of the formula (XI) is added and the reaction mixture is preferably heated, most preferably under reflux Alternatively, compounds of the formula (VII) in which Y is CS may be prepared by the reaction of a compound of the formula (XIV) in which $L^5$ and $L^6$ are as defined above, with a compound of the formula (XI), to form an intermediate of the formula

in which $L^8$ represents either of the leaving groups $L^5$ or $L^6$, followed by the addition of a compound of the formula (VIII). In a typical procedure, a solution of the compound of the formula (XIV) in a suitable solvent, such as ethanol, is treated with the compound of the formula (XI), preferably at an elevated temperature, most preferably under reflux. When analysis by thin layer chromatography shows that a substantially complete reaction has occurred, a compound of the formula (VII) is added and the reaction mixture is preferably heated, most preferably under reflux.

Compounds of the formula (VII) in which Y is SO$_2$ may be prepared by the reaction of a compound of the formula

in which $L^9$ is a suitable leaving group, typically halo, with a compound of the formula (VIII), optionally in the presence of an acid acceptor. Preferably, $L^9$ is chloro. In a typical example, a solution of the compound of the formula (VIII)

in a suitable solvent, such as pyridine, is treated with the compound of the formula (XVII) and preferably heated, most preferably at 90° C. Compounds of the formula (XVII) may be prepared by treating a compound of the formula

with an activating agent. In a typical example, where $L^9$ is chloro, a solution of a compound of the formula (XVIII), in a suitable solvent such as toluene, is treated with PCl$_5$ and heated, preferably under reflux. Compounds of the formula (XVIII) may be prepared by treating a compound of the formula (XI) with chlorosulphonic acid. In a typical procedure, a solution of the compound of the formula (XI) in a suitable solvent, such as dichloromethane, is treated with chlorosulphonic acid, optionally in the presence of a proton acceptor such as triethylamine.

Compounds of the formula (VII) in which Y is C═N(CN) may be prepared by the reaction of a compound of the formula

in which $L^{10}$ and $L^{11}$ are suitable leaving groups, with a compound of the formula (VIII), to form an intermediate of the formula

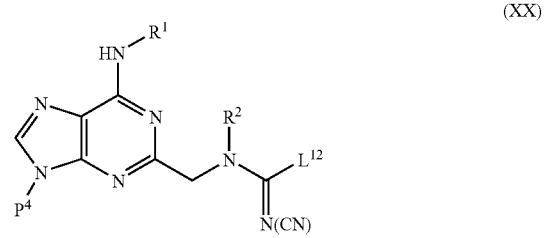

in which $L^{12}$ represents either of leaving groups $L^{10}$ or $L^{11}$, followed by the addition of a compound of the formula (XI). The leaving groups $L^{10}$ and $L^{11}$ may be the same or different and are typically selected from halo and —S(C$_1$–C$_6$ alkyl). Preferably, $L^{10}$ and $L^{11}$ are each methythio. In a typical procedure, where $L^{10}$ and $L^{11}$ are each methylthio, a solution of a compound of the formula (VIII) in a suitable solvent, such as ethanol, is treated with dimethylcyanothioimidocarbamate, preferably at room temperature. When a substantially complete reaction is indicated by thin layer chromatography (TLC), a compound of the formula (XI) is added and the reaction mixture is preferably heated, most preferably under reflux.

Alternatively, compounds of the formula (VII) in which Y is C═N(CN) may be prepared by the reaction of a compound of the formula (XIX) in which $L^{10}$ and $L^{11}$ are as defined above, with a compound of the formula (XI), to form an intermediate of the formula

in which $L^{13}$ represents either of the leaving groups $L^{10}$ or $L^{11}$, followed by the addition of a compound of the formula (VIII). In a typical procedure, where $L^{11}$ and $L^{11}$ are each methylthio, a solution of a compound of the formula (XI) in a suitable solvent, such as ethanol, is treated with dimethylcyanothioimidocarbamate, preferably at room temperature. When a substantially complete reaction is indicated by thin layer chromatography (TLC), a compound of the formula (VIII) is added and the reaction mixture is preferably heated, most preferably under reflux.

Compounds of the formula (VIII) may be prepared by the reduction of a compound of the formula (IX) with a suitable reducing agent, preferably a palladium catalyst and hydrogen gas, in the presence of a compound of the formula $$R^2NH_2 \quad \text{(XXIA)}.$$

In a typical procedure, where $R^2$=H, a compound of the formula (IX) is dissolved in a suitable solvent, such as ethanol, which has been saturated with ammonia gas, a palladium catalyst such as 10% w/w palladium on carbon is added and the reaction mixture is stirred under an atmosphere of hydrogen gas, typically at a pressure of 414 kPa (60 psi). Compounds of the formula (IX) are known in the art (see, for example, WO-A-00/23457). Compounds of the formula (XXIA) are either commercially available or readily prepared by methods well known to those skilled in the art.

Compounds of the formula (III) in which X is —$CH_2CH_2$— (i.e. compounds of the formula (IIIB)) may be prepared according to the route shown in Scheme 2 wherein A represents an activating group and $P^1$, $P^2$ and $P^3$ represent suitable protecting groups. $P^1$, $P^2$ and $P^3$ may be the same or different, $P^1$ and $P^2$ optionally forming part of the same protecting group. Examples of suitable protecting groups will be apparent to the skilled person [see, for instance, 'Protecting groups in Organic Synthesis (Second Edition)', Theodora W. Green and Peter G. M. Wuts, John Wiley and Sons, 1991]. Preferred individual protecting groups are tri($C_1$–$C_6$)alkylsilyl, di($C_1$–$C_6$)alkylphenylsilyl and ($C_1$–$C_6$) alkyldiphenylsilyl. Preferred protecting groups where $P^1$ and $P^2$ form part of the same protecting group are where $P^1$ and $P^2$ taken together are $C_1$–$C_6$ alkylene. Particularly preferred individual protecting groups are tert-butyldimethylsilyl and triethylsilyl. A particularly preferred protecting group where $P^1$ and $P^2$ form part of the same protecting group is where $P^1$ and $P^2$ taken together are dimethylmethylene.

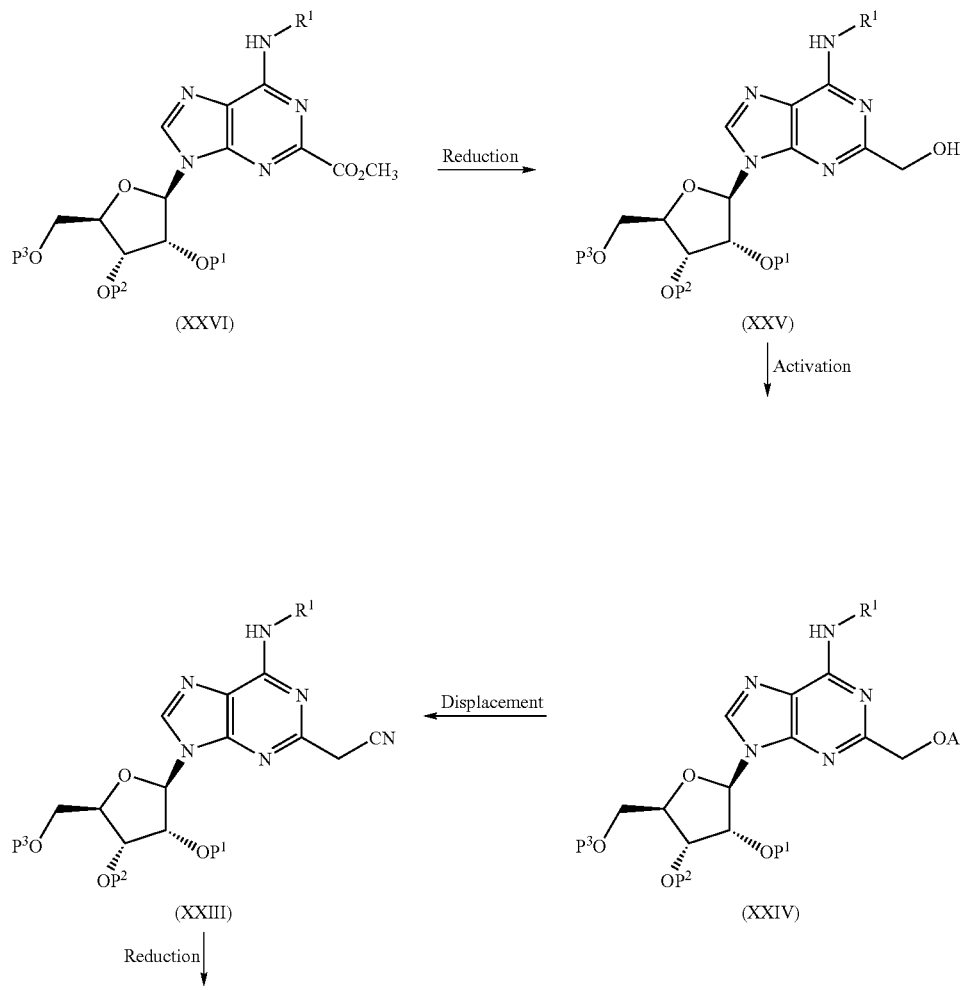

-continued

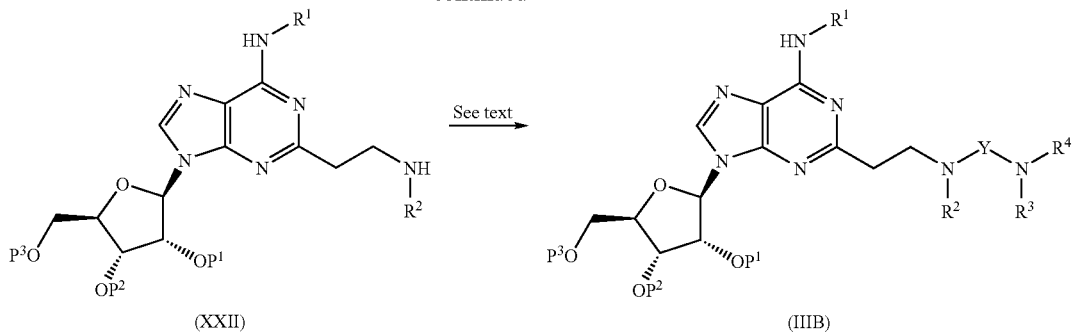

(XXII)　　　　　　　　　　　(IIIB)

In Scheme 2, the compounds of the formula (IIIB) in which Y is CO may be prepared by the reaction of compound of the formula (X), in which $L^1$ is as defined above, with a compound of the formula (XXII) in a suitable solvent, such as a mixture of toluene and isopropanol, typically at an elevated temperature, preferably under reflux.

Alternatively, compounds of the formula (IIIB) in which Y is CO may be 10 prepared by the reaction of a compound of the formula (XXII) with a compound of the formula (XII), in which $L^2$ and $L^3$ are as defined above, to form an intermediate of the formula

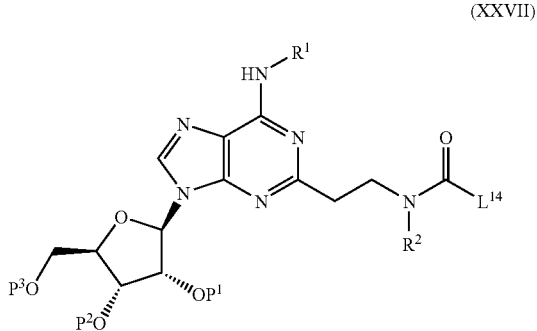

(XXVII)

in which $L^{14}$ represents either of leaving groups $L^2$ or $L^3$. The intermediate (XXVII) is reacted with a compound of the formula (XI) to provide a compound of the formula (IIIB). In a typical example, where $L^2$ and $L^3$ are each imidazol-1-yl, a solution of the compound of the formula (XXII) in a suitable solvent, such as dichloromethane, is treated with 1,1'-carbonyldiimidazole. The reaction mixture is stirred, preferably at room temperature, until thin layer chromatography (TLC) indicates a substantially complete reaction has occurred and then a compound of the formula (XI) is added to give the compound of the formula (IIIB).

Compounds of the formula (I) in which Y is CS may be prepared by the reaction of a compound of the formula (XIV) in which $L^5$ and $L^6$ are as defined above, with a compound of the formula (XXII), to form an intermediate of the formula (XXVIII)

in which $L^{15}$ represents either of leaving groups $L^5$ or $L^6$. The intermediate of the formula (XXVIII) is reacted with a compound of the formula (XI) to provide a compound of the formula (IIIB). In a typical procedure, a solution of the compound of the formula (XIV) in a suitable solvent, such as ethanol, is treated with the compound of the formula (XXII), preferably at an elevated temperature, most preferably under reflux. When analysis by thin layer chromatography shows that a substantially complete reaction has occurred, the compound of the formula (XI) is added and the reaction mixture is preferably heated, most preferably under reflux.

Alternatively, compounds of the formula (IIIB) in which Y is CS may be prepared by the reaction of a compound of the formula (XVI), in which $L^8$ is as defined above, with a compound of the formula (XXII). In a typical procedure, a solution of the compound of the formula (XVI) in a suitable solvent, such as ethanol, is treated with the compound of the formula (XXII) and preferably heated, most preferably under reflux.

Compounds of the formula (IIIB) in which Y is $SO_2$ may be prepared by the reaction of a compound of the formula (XVII), in which $L^9$ is as defined above, with a compound of formula (XXII), optionally in the presence of an acid acceptor. In a typical procedure, a solution of the compound of the formula (XVII) in a suitable solvent, such as pyridine, is treated with the compound of the formula (XXII) and heated, typically at 90° C.

Compounds of the formula (IIIB) in which Y is C=N (CN) may be prepared by the reaction of a compound of the formula (XIX) in which $L^{10}$ and $L^{11}$ are as defined above, with a compound of the formula (XXII), to form an intermediate of the formula

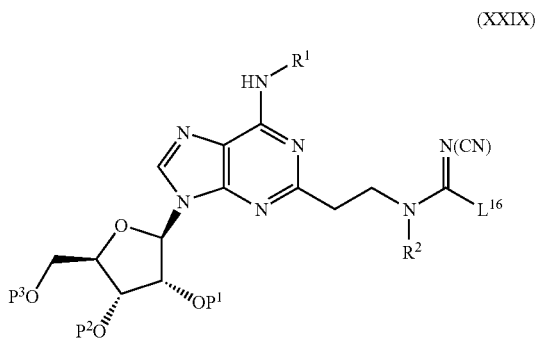

(XXIX)

in which $L^{16}$ represents either of leaving groups $L^{10}$ or $L^{11}$. The intermediate of the formula (XXIX) is reacted with a compound of the formula (XI) to provide a compound of the formula (IIIB). In a typical procedure, where $L^{10}$ and $L^{11}$ are each methylthio, a solution of a compound of the formula (XXII) in a suitable solvent, such as ethanol, is treated with dimethylcyanothioimidocarbamate, preferably at room temperature. When a substantially complete reaction is indicated by thin layer chromatography (TLC), a compound of the formula (XI) is added and the reaction mixture is preferably heated, most preferably under reflux.

Alternatively, compounds of the formula (IIIB) in which Y is C=N(CN) may be prepared by the reaction of a compound of the formula (XXI), in which $L^{13}$ is as defined above, with a compound of the formula (XXII). In a typical procedure, a solution of the compound of the formula (XXI) in a suitable solvent, such as ethanol, is treated with the compound of the formula (XXII) and preferably heated, most preferably under reflux.

Compounds of the formula (XXII) may be prepared by the reduction of a compound of the formula (XXIII) with a suitable reducing agent in the presence of a compound of the formula (XXIA). A preferred reducing agent is Raney nickel, optionally in the presence of hydrogen gas. In a typical procedure, where $R^2$=H, the compound of the formula (XXIII) is dissolved in a suitable solvent, such as ethanol, which has been saturated with ammonia gas, Raney nickel is added and the reaction mixture is shaken, preferably at room temperature.

Compounds of the formula (XXIII) may be prepared by the displacement of a leaving group 'OA', in which A is an activating group, from a compound of the formula (XXIV) with cyanide anion. In a typical example, a solution of the compound of the formula (XXIV) in a suitable solvent, such as N,N-dimethylformamide, is treated with a source of cyanide ion, such as potassium cyanide to give the compound of the formula (XXIII). Examples of suitable choices for A will be apparent to the skilled man [see for example 'Advanced Organic Chemistry (Third Edition)', Jerry March, Wiley-Interscience, 1985]. Preferably, A is ($C_1$–$C_6$) alkylsulphonyl, phenylsulphonyl or (($C_1$–$C_6$)alkylphenyl) sulphonyl. Most preferably, A is methylsulphonyl.

Compounds of the formula (XXIV) may be prepared by the activation of the free hydroxyl in a compound of the formula (XXV). In a typical example, where A is methylsulphonyl, a solution of the compound of the formula (XXV) in a suitable solvent, such as dichloromethane, is treated with methanesulfonyl chloride in the presence of a proton acceptor such as triethylamine.

Compounds of the formula (XXV) may be prepared by the reduction of an ester of the formula (XXVI) with a suitable reducing agent, such as lithium borohydride, in a suitable solvent, such as tetrahydrofuran.

Compounds of the formula (II) in which X is —$CH_2CH_2$— (i.e. compounds of the formula (IIB)) may be prepared according to the route shown in Scheme 3 wherein A represents an activating group, as defined above, and $P^1$ and $P^2$ represent suitable protecting groups. $P^1$ and $P^2$ may be the same or different and optionally form part of the same protecting group. Examples of suitable protecting groups will be apparent to the skilled person [see, for instance, 'Protecting groups in Organic Synthesis (Second Edition)', Theodora W. Green and Peter G. M. Wuts, John Wiley and Sons, 1991]. Preferred individual protecting groups are tri($C_1$–$C_6$)alkylsilyl, di($C_1$–$C_6$)alkylphenylsilyl and ($C_1$–$C_6$) alkyldiphenylsilyl. Preferred protecting groups where $P^1$ and $P^2$ form part of the same protecting group are where $P^1$ and $P^2$ taken together are $C_1$–$C_6$ alkylene. Particularly preferred individual protecting groups are tert-butyldimethylsilyl and triethylsilyl. A particularly preferred protecting group where $P^1$ and $P^2$ form part of the same protecting group is where $P^1$ and $P^2$ taken together are dimethylmethylene.

Scheme 3

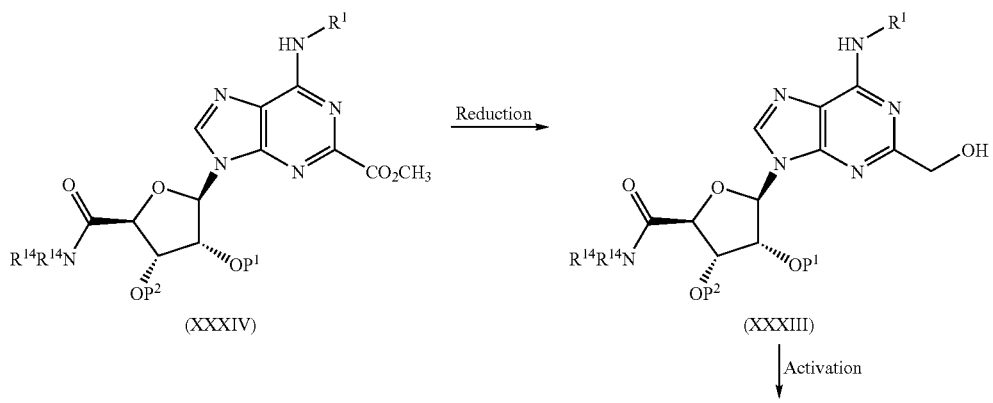

-continued

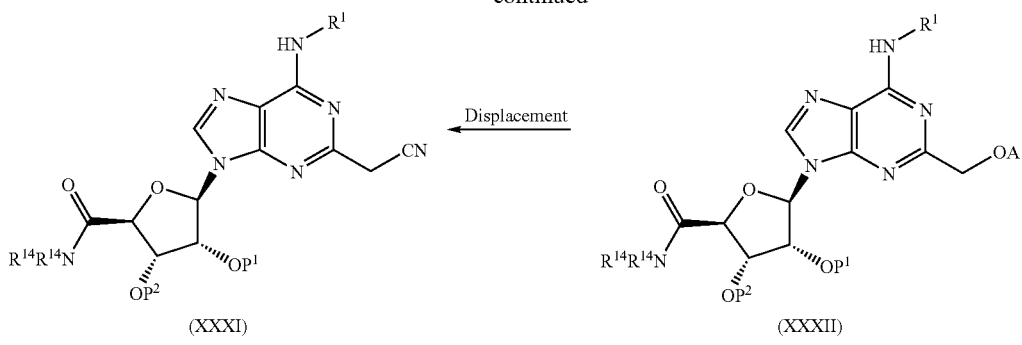

(XXXI)    (XXXII)

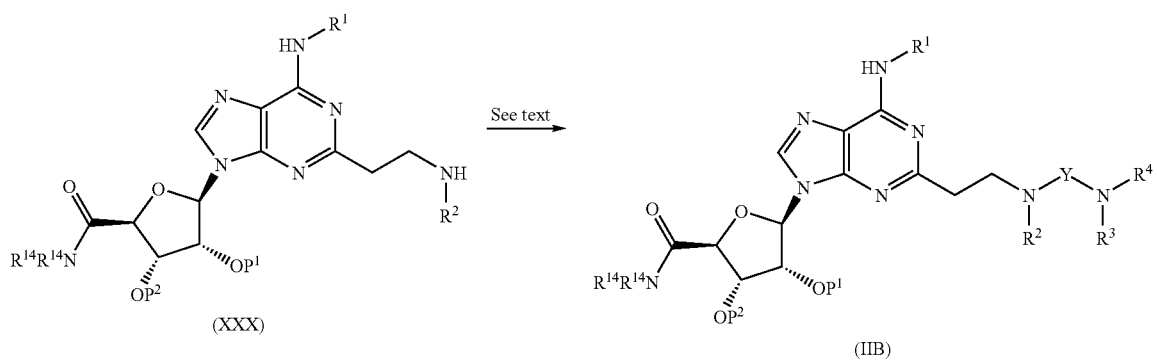

(XXX)    (IIB)

In Scheme 3, the compounds of the formula (IIB) in which Y is CO may be prepared by the reaction of a compound of the formula (X), in which $L^1$ is as defined above, with a compound of the formula (XXX) in a suitable solvent, such as a mixture of toluene and isopropanol, typically at an elevated temperature, preferably under reflux.

Alternatively, compounds of the formula (IIB) in which Y is CO may be prepared by the reaction of a compound of the formula (XXX) with a compound of the formula (XII), in which $L^2$ and $L^3$ are as defined above, to form an intermediate of the formula compound of the formula (XXX) in a suitable solvent, such as dichloromethane, is treated with the compound of the formula (XII). The reaction mixture is stirred, preferably at room temperature, until thin layer chromatography (TLC) indicates a substantially complete reaction has occurred and then a compound of the formula (XI) is added to give the compound of the formula (IIB).

Compounds of the formula (IIB) in which Y is CS may be prepared by the reaction of a compound of the formula (XIV) in which $L^5$ and $L^6$ are as defined above, with a compound of the formula (XXX), to form an intermediate of the formula

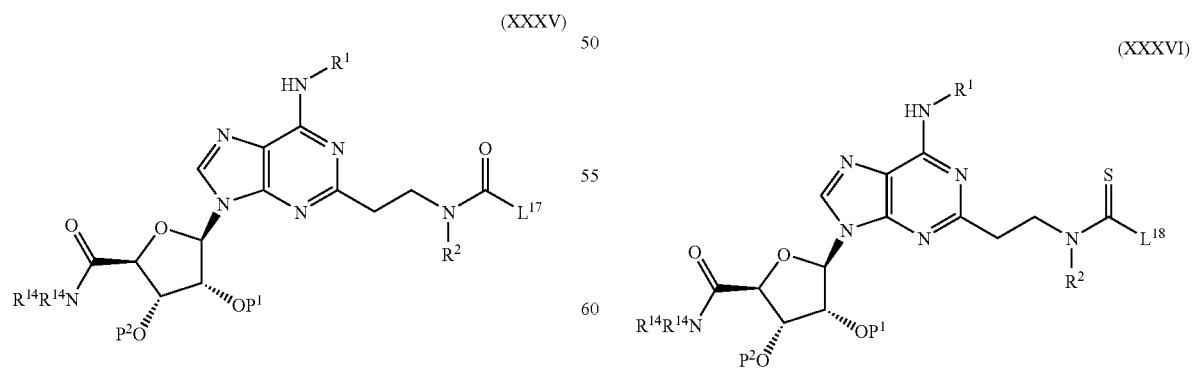

(XXXV)    (XXXVI)

in which $L^{17}$ represents either of leaving groups $L^2$ or $L^3$. The intermediate of the formula (XXXV) is reacted with a compound of the formula (XI) to form a compound of the formula (IIB). In a typical example, a solution of the in which $L^{18}$ represents either of leaving groups $L^5$ or $L^6$. The intermediate of the formula (XXXVI) is reacted with a compound of the formula (XI) to provide a compound of the formula (IIB). In a typical procedure, a solution of the compound of the formula (XIV) in a suitable solvent, such as ethanol, is treated with the compound of the formula (XXX), typically at an elevated temperature. Preferably, the reaction mixture is heated under reflux. When analysis by thin layer chromatography shows that a substantially complete reaction has occurred, the compound of the formula (XI) is added and the reaction mixture is preferably heated, most preferably under reflux.

Alternatively, compounds of the formula (IIB) in which Y is CS may be prepared by the reaction of a compound of the formula (XVI), in which $L^8$ is as defined above, with a compound of the formula (XXX). In a typical procedure, a solution of the compound of the formula (XVI) in a suitable solvent, such as ethanol, is treated with the compound of the formula (XXX), typically at an elevated temperature. Preferably, the reaction mixture is heated under reflux.

Compounds of the formula (IIB) in which Y is $SO_2$ may be prepared by the reaction of a compound of the formula (XVII) in which $L^9$ is as defined above with a compound of the formula (XXX). In a typical example, a solution of the compound of the formula (XXX) in a suitable solvent, such as pyridine, is treated with the compound of the formula (XVII) and heated, typically at 90° C.

Compounds of the formula (IIB) in which Y is C═N(CN) may be prepared by the reaction of a compound of the formula (XIX) in which $L^{10}$ and $L^{11}$ are as defined above, with a compound of the formula (XXX), to form an intermediate of the formula (XXXVII)

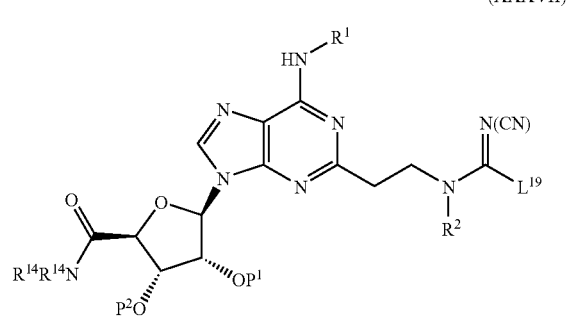

in which $L^{19}$ represents either of leaving groups $L^{10}$ or $L^{11}$. The intermediate of the formula (XXXVII) is reacted with a compound of the formula (XI) to provide a compound of the formula (IIB). In a typical procedure, where $L^{10}$ and $L^{11}$ are each methylthio, a solution of a compound of the formula (XXX) in a suitable solvent, such as ethanol, is treated with dimethylcyanothioimidocarbamate, preferably at room temperature. When a substantially complete reaction is indicated by thin layer chromatography (TLC), a compound of the formula (XI) is added and the reaction mixture is preferably heated, most preferably under reflux.

Alternatively, compounds of the formula (IIB) in which Y is C═N(CN) may be prepared by the reaction of a compound of the formula (XXI), in which $L^{13}$ is as defined above, with a compound of the formula (XXX). In a typical procedure, a solution of the compound of the formula (XXI) in a suitable solvent, such as ethanol, is treated with the compound of the formula (XXX) and preferably heated, most preferably under reflux.

Compounds of the formula (XXX) may be prepared by the reduction of a compound of the formula (XXXI) with a suitable reducing agent in the presence of a compound of theformula (XXIA). A preferred reducing agent is Raney nickel, optionally in the presence of hydrogen gas. In atypical example, where $R^2$═H, a compound of the formula (XXXI) is dissolved in a suitable solvent, such as ethanol, which has been saturated with ammonia gas, Raney nickel is added and the reaction mixture is shaken, preferably at room temperature.

Compounds of the formula (XXXI) may be prepared by the displacement of a leaving group 'OA', from a compound of the formula (XXXII) with cyanide anion. In a typical example, a solution of the compound of the formula (XXXII) in a suitable solvent, such as N,N-dimethylformamide, is treated with a source of cyanide ion, such as potassium cyanide, to give the compound of the formula (XXXI).

Compounds of the formula (XXXII) may be prepared by the activation of the free hydroxyl in a compound of the formula (XXXIII). In a typical example, where A is methylsulphonyl, a solution of the compound of the formula (XXXIII) in a suitable solvent, such as dichloromethane, is treated with methanesulphonyl chloride in the presence of a proton acceptor such as triethylamine.

Compounds of the formula (XXXIII) may be prepared by the reduction of an ester of the formula (XXXIV) with a suitable reducing agent, such as lithium borohydride, in a suitable solvent, such as tetrahydrofuran.

2. Compounds of the formula (I) may also be prepared by the derivatisation of a compound of the formula as described below.

(XXXVIII)

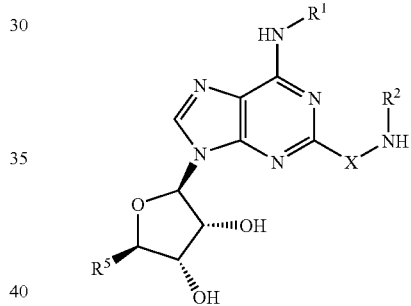

Compounds of the formula (I) in which Y is CO may be prepared by the reaction of a compound of the formula (X), in which $L^1$ is as defined above, with a compound of the formula (XXXVIII) in a suitable solvent, such as a mixture of toluene and isopropanol, preferably at an elevated temperature, most preferably under reflux.

Alternatively, compounds of the formula (I) in which Y is CO may be prepared by the reaction of a compound of the formula (XXXVIII) with a compound of the formula (XII), in which $L^2$ and $L^3$ are as defined above, to form an intermediate of the formula (XXXIX)

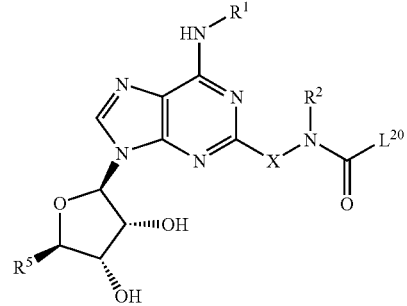

in which $L^{20}$ represents either of leaving groups $L^2$ or $L^3$.

The intermediate (XXXIX) is reacted with a compound of the formula (XI) to provide a compound of the formula (I). In a typical example, where $L^2$ and $L^3$ are each imidazol-1-yl, a solution of the compound of the formula (XXXVIII) in a suitable solvent, such as dichloromethane, is treated with 1,1'-carbonyldiimidazole. The reaction mixture is stirred, preferably at room temperature, until thin layer chromatography (TLC) indicates a substantially complete reaction has occurred and then a compound of the formula (XI) is added to give the compound of the formula (I).

Compounds of the formula (I) in which Y is CS may be prepared by the reaction of a compound of the formula (XIV) in which $L^5$ and $L^6$ are as defined above, with a compound of the formula (XXXVIII), to form an intermediate of the formula

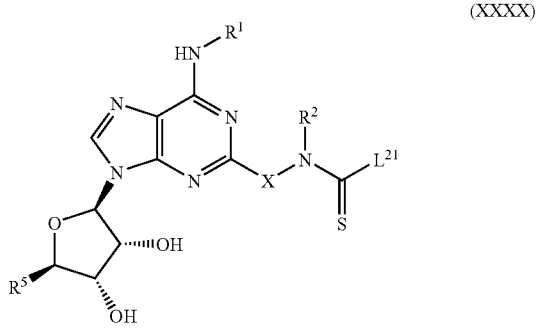

(XXXX)

in which $L^{21}$ represents either of the leaving groups $L^5$ or $L^6$. The intermediate of the formula (XXXX) is reacted with a compound of the formula (XI) to provide a compound of the formula (I). In a typical procedure, a solution of the compound of the formula (XXXVIII) in a suitable solvent, such as ethanol, is treated with the compound of the formula (XIV), preferably at an elevated temperature, most preferably under reflux. When analysis by thin layer chromatography shows that a substantially complete reaction has occurred, a compound of the formula (XI) is added and the reaction mixture is preferably heated, most preferably under reflux.

Alternatively, compound of the formula (I) in which Y is CS may be prepared by the reaction of a compound of the formula (XVI) in which $L^8$ is as defined above with a compound of the formula (XXXVIII). In a typical procedure, a solution of the compound of the formula (XVI) in a suitable solvent, such as ethanol, is treated with the compound of the formula (XXXVIII) and preferably heated, most preferably under reflux.

Compounds of the formula (I) in which Y is $SO_2$ may be prepared by the reaction of a compound of the formula (XVII), in which $L^9$ is as defined above, with a compound of the formula (XXXVIII), optionally in the presence of an acid acceptor. In a typical procedure, a solution of the compound of the formula (XXXVIII) in a suitable solvent, such as pyridine, is treated with the compound of the formula (XVII) and heated, typically at 90° C.

Compounds of the formula (I) in which Y is C=N(CN) may be prepared by the reaction of a compound of the formula (XIX) in which $L^{10}$ and $L^{11}$ are as defined above, with a compound of the formula (XXXVIII), to form an intermediate of the formula

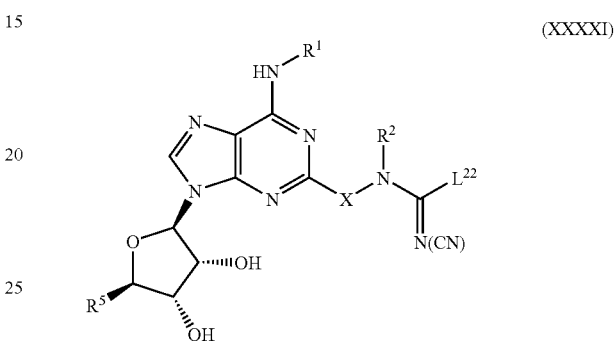

(XXXXI)

in which $L^{22}$ represents either of $L^{10}$ or $L^{11}$. The intermediate of the formula (XXXXI) is reacted with a compound of the formula (XI) to give a compound of the formula (I). In a typical procedure, where $L^{10}$ and $L^{11}$ are each methylthio, a solution of a compound of the formula (XXXVIII) in a suitable solvent, such as ethanol, is treated with dimethylcyanothioimidocarbamate, preferably at room temperature. When a substantially complete reaction is indicated by thin layer chromatography (TLC), a compound of the formula (XI) is added and the reaction mixture is preferably heated, most preferably under reflux, to give the compound of the formula (I).

Alternatively, compounds of the formula (I) in which Y is C=N(CN) may be prepared by the reaction of a compound of the formula (XXI), in which $L^{13}$ is as defined above, with a compound of the formula (XXXVIII). In a typical procedure, a solution of the compound of the formula (XXI) in a suitable solvent, such as ethanol, is treated with the compound of the formula (XXXVIII) and preferably heated, most preferably under reflux.

Compounds of the formula (XXXVIII) may be prepared according to the route shown in Scheme 4, wherein $P^1$, $P^2$ and $P^3$ are as defined above.

Scheme 4

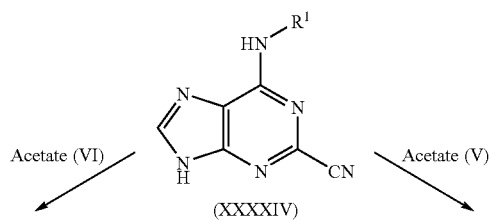

(XXXXIV)

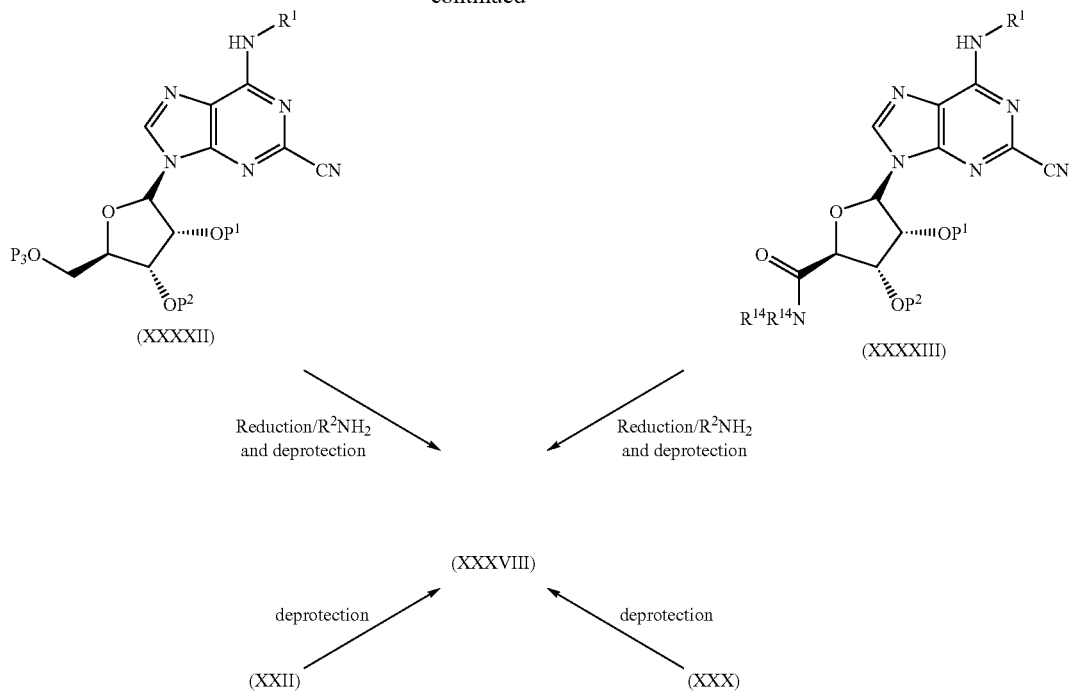

(XXXXII)

(XXXXIII)

Reduction/R²NH₂ and deprotection

Reduction/R²NH₂ and deprotection (XXXVIII)

deprotection deprotection (XXII)

(XXX)

Compounds of the formula (XXXVIII) in which $R^5$ is —CH₂OH and X is —CH₂— may be prepared by reducing a compound of the formula (XXXXII) in the presence of a compound of the formula (XXIA) to give a compound of the formula (XXXXV)

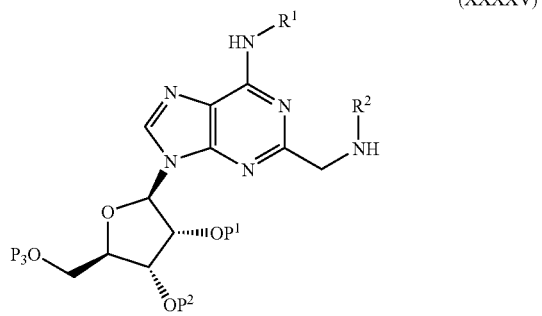

in which $P^1$, $P^2$ and $P^3$ are as defined above, and deprotecting the compound of the formula (XXXXV). Alternatively, if the protecting groups employed are readily removed by the conditions chosen for the reduction, then the reducing and deprotecting steps will usually be performed together to give a compound of the formula (XXXVIII) directly from a compound of the formula (XXXXII). The reduction is carried out using a suitable reducing agent, such as a palladium catalyst and hydrogen gas, in the presence of a compound of formula (XXIA). Suitable conditions for the deprotection are well known in the art [see, for instance, 'Protecting groups in Organic Synthesis (Second Edition)', Theodora W. Green and Peter G. M. Wuts, John Wiley and Sons, 1991]. In a typical procedure, where $R^2$ is H, $P^1$, $P^2$ and $P^3$ are each acetyl and the reducing and deprotecting steps are carried out together, a compound of the formula (XXXXII) is dissolved in a suitable solvent, such as ethanol, which has been saturated with ammonia gas, a palladium catalyst, such as 10% w/w palladium on carbon, is added and the reaction is stirred under an atmosphere of hydrogen gas, typically at a pressure of 414 kPa (60 psi).

Compounds of the formula (XXXVIII) in which $R^5$ is —CONR¹⁴R¹⁴ and X is —CH₂— may be prepared by reducing a compound of the formula (XXXXIII) in the presence of a compound of the formula (XXIA) to give a compound of the formula (XXXXVI)

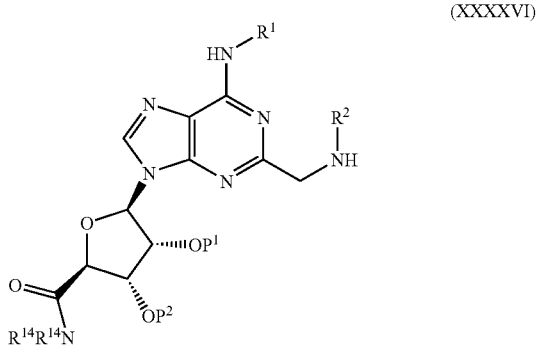

wherein $P^1$ and $P^2$ are as defined above and deprotecting the compound of the formula (XXXXVI). Alternatively, if the protecting groups employed are readily removed by the conditions chosen for the reduction, then the reducing and deprotecting steps will usually be performed together to give a compound of the formula (XXXVIII) directly from a compound of the formula (XXXXIII). The reduction is carried out using a suitable reducing agent, such as a palladium catalyst and hydrogen gas, in the presence of a compound of formula (XXIA). Suitable conditions for the deprotection are well known in the art [see, for instance, 'Protecting groups in Organic Synthesis (Second Edition)', Theodora W. Green and Peter G. M. Wuts, John Wiley and Sons, 1991]. In a typical procedure, where $R^2$ is H, $P^1$ and $P^2$ are each benzoyl and the reducing and deprotecting are carried out together, a compound of the formula (XXXXIII) is dissolved in a suitable solvent, such as ethanol, which has been saturated with ammonia gas, a palladium catalyst, such as 10% w/w palladium on carbon, is added and the reaction is stirred under an atmosphere of hydrogen gas, typically at a pressure of 414 kPa (60 psi).

Compounds of the formula (XXXXII) may be prepared by the reaction of an acetate of the formula (VI) with trimethylsilyl trifluoromethanesulfonate and a compound of the formula (XXXXIV) which has been derivatised with N,O-bis(trimethylsilyl)acetamide. In a typical procedure, a compound of the formula (XXXXIV) is heated, in the presence of a suitable solvent, such as 1,1,1-trichloroethane, with N,O-bis(trimethylsilyl)acetamide, preferably under reflux. The mixture is then allowed to cool and the solvent is removed. A solution of the residue in a suitable solvent, such as toluene, is treated with the acetate of the formula (VI) and trimethylsilyl trifluoromethanesulfonate. The mixture so formed is preferably heated, most preferably under reflux, under a nitrogen atmosphere, to give the compound of the formula (XXXXII).

Compounds of the formula (XXXXIII) may be prepared by the reaction of an acetate of the formula (V) with a compound of the formula (XXXXIV) and iodine. In a typical example, a compound of the formula (XXXXIV), a compound of the formula (V) and iodine are heated together, preferably at 150° C., under reduced pressure, preferably at 7 kPa (1 psi).

Compounds of the formula (XXXXIV) are known in the art (see, for example, WO-A-00/23457).

Compounds of the formula (XXXVIII) in which $R^5$ is —CH$_2$OH and X is —CH$_2$CH$_2$— may be prepared by the deprotection of a compound of the formula (XXII), in which protecting groups $P^1$, $P^2$ and $P^3$ are as defined above. Suitable conditions for the deprotection are well known in the art [see, for instance, 'Protecting groups in Organic Synthesis (Second Edition)', Theodora W. Green and Peter G. M. Wuts, John Wiley and Sons, 1991]. In a typical procedure, a solution of a compound of the formula (XXII), wherein $P^1$, $P^2$ and $P^3$ are each tert-butyldimethylsilyl, in a suitable solvent, such as methanol, is treated with an acid such as hydrochloric acid, typically at room temperature.

Compounds of the formula (XXXVIII) in which $R^5$ is —CONR$^{14}$R$^{14}$ and X is —CH$_2$CH$_2$— may be prepared by the deprotection of a compound of the formula (XXX) in which protecting groups $P^1$ and $P^2$ are as defined above. Suitable conditions for the deprotection are well known in the art [see, for instance, 'Protecting groups in Organic Synthesis (Second Edition)', Theodora W. Green and Peter G. M. Wuts, John Wiley and Sons, 1991]. In a typical procedure, a solution of a compound of the formula (XXX), wherein $P^1$ and $P^2$ are each tert-butyldimethylsilyl, in a suitable solvent, such as methanol, is treated with an acid such as hydrochloric acid, typically at room temperature.

Scheme 5, wherein $P^1$, $P^2$, $P^3$ and $P^4$ are as defined above, illustrates the preparation of compounds of the formula (XXVI) and compounds of the formula (XXXIV) used in Schemes 2 and 3 respectively.

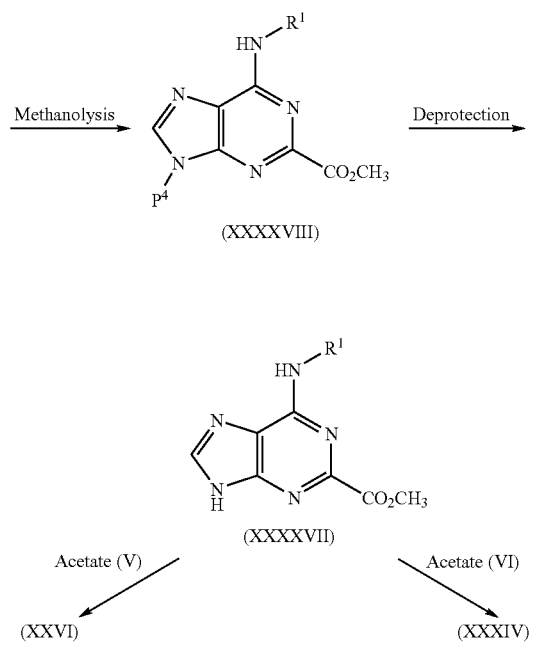

In Scheme 5, compounds of the formula (XXVI) may be prepared by the reaction of a compound of the formula (V) with trimethylsilyl trifluoromethanesulfonate and a compound of the formula (XXXXVII) which has been derivatised with N,O-bis(trimethylsilyl)acetamide. In a typical procedure, the compound of the formula (XXXXVII) is heated in the presence of a suitable solvent, such as 1,1,1-trichloroethane, with N,O-bis(trimethylsilyl)acetamide at an elevated temperature, preferably under reflux. The mixture is then allowed to cool and the solvent is removed. A solution of the residue in a suitable solvent, such as toluene, is treated with the compound of the formula (V) and trimethylsilyl trifluoromethanesulfonate and the mixture is heated, preferably under reflux, under a nitrogen atmosphere, to give the compound of the formula (XXVI).

Compounds of the formula (XXXIV) may be prepared by the reaction of a compound of the formula (VI) with trimethylsilyl trifluoromethanesulfonate and a compound of the formula (XXXXVII) which has been derivatised with N,O-bis(trimethylsilyl)acetamide. In a typical procedure, the compound of the formula (XXXXVII) is heated in the presence of a suitable solvent, such as 1,1,1-trichloroethane, with N,O-bis(trimethylsilyl)acetamide at an elevated temperature, preferably under reflux. The mixture is then allowed to cool and the solvent is removed. A solution of the residue in a suitable solvent, such as toluene, is treated with the compound of the formula (VI) and trimethylsilyl trifluoromethanesulfonate and the mixture is heated, preferably under reflux, under a nitrogen atmosphere, to give the compound of the formula (XXXIV).

It may be desirable in certain cases, having regard to the conditions used in future steps, to change the protecting groups in compounds of the formula (XXVI) or (XXXIV) prepared in this way. Suitable conditions for both the deprotecting step are well known to the skilled person [see, for instance, 'Protecting groups in Organic Synthesis (Second Edition)', Theodora W. Green and Peter G. M. Wuts, John Wiley and Sons, 1991]. In a typical procedure, where $P^1$, $P^2$ and, where appropriate, $P^3$ are each acetyl, a solution of the compound of the formula (XXVI) or the compound of the formula (XXXIV), as the case may be, in a suitable solvent, such as methanol, is treated with a nucleophile such as ammonia or a primary amine, or a base such as potassium carbonate, typically at room temperature. Suitable conditions for the subsequent protecting step are also well known to the skilled person [see, for instance, 'Protecting groups in Organic Synthesis (Second Edition)', Theodora W. Green and Peter G. M. Wuts, John Wiley and Sons, 1991]. In a typical example, where the new protecting groups are to be each tert-butyldimethylsilyl, a solution of the deprotected intermediate, in a suitable solvent such as N,N-dimethylformamide, is treated with tert-butyldimethylsilylchloride and a suitable proton acceptor such as imidazole.

Compounds of the formula (XXXXVII) may be prepared by the deprotection of a compound of the formula (XXXVIII). Suitable conditions for the deprotection are well known in the art [see, for instance, 'Protecting groups in Organic Synthesis (Second Edition)', Theodora W. Green and Peter G. M. Wuts, John Wiley and Sons, 1991]. In a typical procedure, where $P^4$ is tetrahydropyran-2-yl, the protecting group may be removed by treating a solution of the compound of the formula (XXXXVIII) in a suitable solvent, such as ethanol, with an acid such as hydrochloric acid.

Compounds of the formula (XXXXVIII) may be prepared by the methanolysis of a compound of the formula (IX). In a typical procedure, a solution of a compound of the formula (IX) in methanol is treated with an alkali metal methoxide, preferably sodium methoxide, and heated under reflux. The resulting mixture is cooled, evaporated, dissolved in a suitable solvent such as tetrahydrofuran and treated with an acid, such as hydrochloric acid, preferably 2N hydrochloric acid, to give the compound of the formula (XXXXVIII).

Compounds of the formula (V), as used in Schemes 1, 4 and 5, may be prepared as shown in Scheme 6, wherein $P^1$ and $P^2$ are as defined above.

Scheme 6

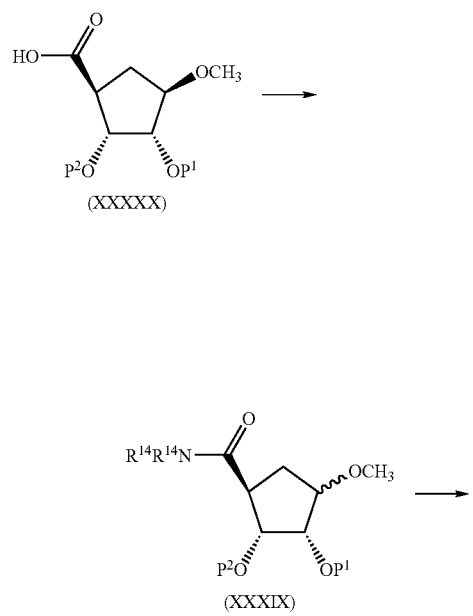

(XXXXX)

(XXXIX)

-continued

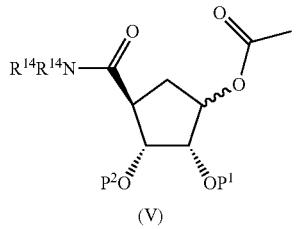

(V)

In Scheme 6, compounds of the formula (V) may be prepared by the treatment of a compound of the formula (XXXXIX) with a mixture of acetic acid, acetic anhydride and a strong acid such as hydrochloric or sulphuric acid with cooling (typically to −10° C.). A compound of formula (XXXXIX) may be prepared from an acid of the formula (XXXXX) by activation of the acid as, for example, an acid chloride and treatment of this activated intermediate with a compound of the formula $$R^{14}R^{14}NH \qquad\qquad (XXXXXI).$$

In a typical procedure, a compound of formula (XXXXX) is dissolved in a suitable inert solvent (e.g. dichloromethane) and treated with oxalyl chloride and a catalytic amount of N,N-dimethylformamide. After removal of excess solvent and reagent by evaporation under reduced pressure, the residue is dissolved in anhydrous dichloromethane and treated with a compound of the formula (XXXXXI). With regard to the conditions employed in later steps, it may be appropriate to change the protecting groups $P^1$ and $P^2$ in compounds of the formula (XXXXIX). Alternative, suitable protecting groups are well-known to the skilled person [e.g. 'Protecting Groups in Organic Synthesis (Second Edition)', Theodora W. Green and Peter G. M. Wuts, John Wiley and Sons, 1991]. In a typical case, a solution of the compound of formula (XXXXIX) wherein $P^1$ and $P^2$ taken together are dimethylmethylene in a suitable solvent such as methanol may treated with an acid such as pyridinium para-toluenesulphonate to give a compound of formula (XXXXIX) wherein $P^1$ and $P^2$ are both replaced by H which may be subsequently reprotected with other functionality. For instance, the compound of formula (XXXXIX) wherein $P^1$ and $P^2$ are both replaced by H may be dissolved in a suitable solvent such as dichloromethane and the resulting solution may be treated with an acid acceptor, such as pyridine, and benzoyl chloride to give a compound of formula (XXXXIX) wherein $P^1$ and $P^2$ are each benzoyl. Compounds of the formula (XXXXX) are known in the art (see, for example, J. Am. Chem. Soc., 1958, 80, 5168).

Compounds of the formula (XXXXXI) are either commercially available or easily prepared by methods well known to the person skilled in the art.

Compounds of the formula (VI), as used in Schemes 1, 4 and 5, are either commercially available or easily prepared by methods well known to the person skilled in the art.

3. Compounds of the formula (I) in which $R^4$ is —($C_2$–$C_6$ alkylene)—$NR^{11}R^a$, wherein $R^a$ is —$CONR^9R^9$, —$COOR^{10}$, —$COR^{10}$, —$SO_2R^{10}$ or —$SO_2NR^9R^9$, may be prepared by the derivatisation of an amine of the formula

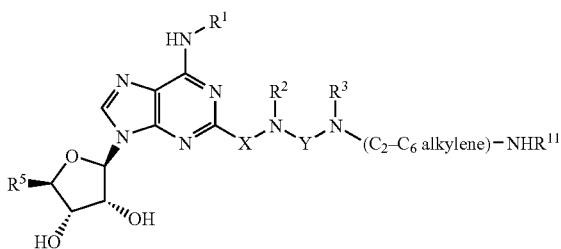

(XXXXXII)

with a suitable acylating or sulphonylating agent. For example, compounds of the formula (I) in which $R^4$ is —($C_2$–$C_6$ alkylene)—$NR^{11}COR^{10}$ may be prepared by the reaction of a compound of the formula (XXXXXII) with an acid chloride of the formula

$R^{10}COCl$ (XXXXXIII).

In a typical procedure, a solution of the compound of the formula (XXXXXII) in a suitable solvent, such as a mixture of ethyl acetate and N-methylpyrrolidinone, is treated with a suitable base, preferably a trialkylamine base such as triethylamine, and the compound of the formula (XXXXXIII). As a further example, compounds of the formula (I) in which $R^4$ is —($C_2$–$C_6$ alkylene)—$NR^{11}SO_2R^{10}$ may be prepared by the reaction of a compound of the formula (XXXXXII) with a compound of the formula

$R^{10}SO_2Cl$ (XXXXXIV).

In a typical procedure, a solution of the compound of the formula (XXXXXII) in a suitable solvent, such as a mixture of ethyl acetate and N-methylpyrrolidinone, is treated with a suitable base, preferably a trialkylamine base such as triethylamine, and the compound of the formula (XXXXXIV).

Compounds of the formula (XXXXXII) may be prepared by analogy with the methods presented above for the preparation of compounds of the formula (I). Compounds of the formula (XXXXXIII) or (XXXXXIV) are either commercially available or are easily prepared by methods well known to the skilled man.

A pharmaceutically acceptable salt of a compound of the formula (I) may be readily prepared by mixing together solutions of a compound of the formula (I) and the desired acid or base, as appropriate. The salt may precipitate from solution and be collected by filtration or may be recovered by evaporation of the solvent.

The anti-inflammatory properties of the compounds of the formula (I) are demonstrated by their ability to inhibit neutrophil function which indicates A2a receptor agonist activity. This was evaluated by determining the compound profile in an assay where superoxide production was measured from neutrophils activated by fMLP. Neutrophils were isolated from human peripheral blood using dextran sedimentation followed by centrifugation through Ficoll-Hypaque solution. Any contaminating erythrocytes in the granulocyte pellet were removed by lysis with ice-cold distilled water. Superoxide production from the neutrophils was induced by fMLP in the presence of a priming concentration of cytochalasin B. Adenosine deaminase was included in the assay to remove any endogenously produced adenosine that might suppress superoxide production. The effect of the compound on the fMLP-induced response was monitored colorometrically from the reduction of cytochrome C within the assay buffer. The potency of the compounds was assessed by the concentration giving 50% inhibition ($IC_{50}$) compared to the control response to fMLP.

The compounds of the formula (I) can be administered alone but will generally be administered in admixture with a suitable pharmaceutical excipient, diluent or carrier selected with regard to the intended route of administration and standard pharmaceutical practice.

For example, the compounds of the formula (I) can be administered orally, buccally or sublingually in the form of tablets, capsules, multi-particulates, gels, films, ovules, elixirs, solutions or suspensions, which may contain flavouring or colouring agents, for immediate-, delayed-, modified-, sustained-, pulsed- or controlled-release applications. The compounds of the formula (I) may also be administered as fast-dispersing or fast-dissolving dosage forms or in the form of a high energy dispersion or as coated particles. Suitable formulations of the compounds of the formula (I) may be in coated or uncoated form, as desired.

Such solid pharmaceutical compositions, for example, tablets, may contain excipients such as microcrystalline cellulose, lactose, sodium citrate, calcium carbonate, dibasic calcium phosphate, glycine and starch (preferably corn, potato or tapioca starch), disintegrants such as sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

GENERAL EXAMPLE

A formulation of the tablet could typically contain between about 0.01 mg and 500 mg of active compound whilst tablet fill weights may range from 50 mg to 1000 mg. An example of a formulation for a 10 mg tablet is illustrated below:

| Ingredient | % w/w |
| --- | --- |
| Compound of the formula (I) or salt | 10.000* |
| Lactose | 64.125 |
| Starch | 21.375 |
| Croscarmellose sodium | 3.000 |
| Magnesium Stearate | 1.500 |

*Quantity adjusted in accordance with drug activity.

The tablets are manufactured by a standard process, for example, direct compression or a wet or dry granulation process. The tablet cores may be coated with appropriate overcoats.

Solid compositions of a similar type may also be employed as fillers in gelatin or HPMC capsules. Preferred excipients in this regard include lactose, starch, a cellulose, milk sugar or high molecular weight polyethylene glycols. For aqueous suspensions and/or elixirs, the compounds of the formula (I) may be combined with various sweetening or flavouring agents, colouring matter or dyes, with emulsifying and/or suspending agents and with diluents such as water, ethanol, propylene glycol and glycerin, and combinations thereof.

The compounds of the formula (I) can also be administered parenterally, for example, intravenously, intra-arterially, intraperitoneally, intrathecally, intraventricularly, intraurethrally, intrasternally, intracranially, intramuscularly or subcutaneously, or they may be administered by infusion or needleless injection techniques. For such parenteral administration they are best used in the form of a sterile aqueous solution which may contain other substances, for example, a co-solvent and/or enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

For oral and parenteral administration to human patients, the daily dosage level of the compounds of the formula (I) will usually be from 0.00001 to 100 mg/kg, preferably from 0.0001 to 100 mg/kg (in single or divided doses).

Thus tablets or capsules of the compound of the formula (I) may contain from 0.01 to 500 mg of active compound for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention.

The compounds of formula (I) can also be administered intranasally or by inhalation and are conveniently delivered in the form of a dry powder inhaler or an aerosol spray presentation from a pressurised container, pump, spray, atomiser (preferably an atomiser using electrohydrodynamics to produce a fine mist) or nebuliser, with or without the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A [trade mark]) or 1,1,1,2,3,3,3-heptafluoropropane (HFA 227EA [trade mark]), carbon dioxide, a further perfluorinated hydrocarbon such as Perflubron (trade mark) or other suitable gas. In the case of a pressurised aerosol, the dosage unit may be determined by providing a valve to deliver a metered amount. The pressurised container, pump, spray, atomiser or nebuliser may contain a solution or suspension of the active compound, e.g. using a mixture of ethanol (optionally aqueous ethanol) or a suitable agent for dispersing, solubilising or extending release and the propellant as the solvent, which may additionally contain a lubricant, e.g. sorbitan trioleate. Capsules, blisters and cartridges (made, for example, from gelatin or HPMC) for use in an inhaler or insufflator may be formulated to contain a powder mix of a compound of the formula (I) and a suitable powder base such as lactose or starch and a performance modifier such as L-leucine, manitol or magnesium stearate.

A suitable solution formulation for use in an atomiser using electrohydrodynamics to produce a fine mist may contain from 1 gg to 10 mg of a compound of the formula (I), or a salt thereof, and the actuation volume may vary from 1 to 100 μl. A typical formulation may comprise a compound of the formula (I) or salt thereof, propylene glycol, sterile water, ethanol and sodium chloride.

Aerosol or dry powder formulations are preferably arranged so that each metered dose or "puff" contains from 1 to 4000 μg of a compound of the formula (I) for delivery to the patient. The overall daily dose with an aerosol will be in the range of from 1 μg to 20 mg which may be administered in a single dose or, more usually, in divided doses throughout the day.

Alternatively, the compounds of the formula (I) can be administered in the form of a suppository or pessary, or they may be applied topically in the form of a lotion, solution, cream, ointment or dusting powder. The compounds of the formula (I) may also be dermally or transdermally administered, for example, by the use of a skin patch. They may also be administered by the pulmonary, vaginal or rectal routes.

For application topically to the skin, the compounds of the formula (I) can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

The compounds of the formula (I) may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser. Alpha-, beta- and gamma-cyclodextrins are most commonly used and suitable examples are described in WO-A-91/11172, WO-A-94/02518 and WO-A-98/55148.

It is to be appreciated that all references herein to treatment include curative, palliative and prophylactic treatment.

Thus the invention provides:

(i) a compound of the formula (I) or a pharmaceutically acceptable salt or solvate thereof;

(ii) a process for the preparation of a compound of the formula (I) or a pharmaceutically acceptable salt or solvate thereof;

(iii) a pharmaceutical composition including a compound of the formula (I) or a pharmaceutically acceptable salt or solvate thereof, together with a pharmaceutically acceptable excipient, diluent or carrier;

(iv) a compound of the formula (I) or a pharmaceutically acceptable salt, solvate or composition thereof, for use as a medicament;

(v) the use of a compound of the formula (I) or of a pharmaceutically acceptable salt, solvate or composition thereof, for the manufacture of a medicament having A2a receptor agonist activity;

(vi) the use of a compound of the formula (I) or of a pharmaceutically acceptable salt, solvate or composition thereof, for the manufacture of an anti-inflammatory agent;

(vii) the use of a compound of the formula (I) or of a pharmaceutically acceptable salt, solvate or composition thereof, for the manufacture of a medicament for the treatment of a respiratory disease;

(viii) use as in (vii) where the disease is selected from the group consisting of adult respiratory distress syndrome (ARDS), bronchitis, chronic bronchitis, chronic obstructive pulmonary disease, cystic fibrosis, asthma, emphysema, bronchiectasis, chronic sinusitis and rhinitis;

(ix) the use of a compound of the formula (I) or of a pharmaceutically acceptable salt, solvate or composition thereof, for the manufacture of a medicament for the treatment of septic shock, male erectile dysfunction, hypertension, stroke, epilepsy, cerebral ischaemia, peripheral vascular disease, post-ischaemic reperfusion injury, diabetes, rheumatoid arthritis, multiple sclerosis, psoriasis, dermatitis, allergic dermatitis, eczema, ulcerative colitis, Crohns disease, inflammatory bowel disease, Heliobacter pylori gastritis, non-Heliobacter pylor gastritis, non-steroidal anti-inflammatory drug-induced damage to the gastro-intestinal tract or a psychotic disorder, or for wound healing;

(x) a method of treatment of a mammal, including a human being, with a A2a receptor agonist including treating said mammal with an effective amount of a compound of the formula (I) or with a pharmaceutically acceptable salt, solvate or composition thereof;

(xi) a method of treatment of a mammal, including a human being, to treat an inflammatory disease including treating said mammal with an effective amount of a compound of the formula (I) or with a pharmaceutically acceptable salt, solvate or composition thereof;

(xii) a method of treatment of a mammal, including a human being, to treat a respiratory disease including treating said mammal with an effective amount of a compound of the formula (I) or with a pharmaceutically acceptable salt, solvate or composition thereof;

(xiii) a method as in (xii) where the disease is selected from the group consisting of adult respiratory distress syndrome (ARDS), bronchitis, chronic bronchitis, chronic obstructive pulmonary disease, cystic fibrosis, asthma, emphysema, bronchiectasis, chronic sinusitis and rhinitis;

(xiv) a method of treatment of a mammal, including a human being, to treat septic shock, male erectile dysfunction, hypertension, stroke, epilepsy, cerebral ischaemia, peripheral vascular disease, post-ischaemic reperfusion injury, diabetes, rheumatoid arthritis, multiple sclerosis, psoriasis, dermatitis, allergic dermatitis, eczema, ulcerative colitis, Crohns disease, inflammatory bowel disease, *Heliobacter pylori* gastritis, non-*Heliobacter pylori* gastritis, non-steroidal anti-inflammatory drug-induced damage to the gastrointestinal tract or a psychotic disorder, or for wound healing, including treating said mammal with an effective amount of a compound of the formula (I) or with a pharmaceutically acceptable salt, solvate or composition thereof; and (xv) certain novel intermediates disclosed herein.

The following Examples illustrate the preparation of the compounds of the formula (I).

$^1$H Nuclear magnetic resonance (NMR) spectra were in all cases consistent with the proposed structures. Characteristic chemical shifts ($\delta$) are given in parts-per-million downfield from tetramethylsilane using conventional abbreviations for designation of major peaks: e.g. s, singlet; d, doublet; t, triplet; q, quartet; m, multiplet; br, broad. The mass spectra (m/z) were recorded in either thermospray or electrospray ionisation mode. The following abbreviations have been used for common solvents: CDCl$_3$, deuterochloroform; D$_6$DMSO, deuterodimethylsulphoxide; CD$_3$OD, deuteromethanol; THF, tetrahydrofuran. The reagent '0.88 concentrated aqueous ammonia' is a concentrated solutionof ammonia in water possessing a specific gravity of 0.88.Where thin layer chromatography (TLC) has been used it refers to silica gel TLC using silica gel 60 F$_{254}$ plates, R$_f$ is the distance travelled by a compound divided by the distance travelled by the solvent front on a TLC plate.

Example 1

N-({9-[(2R,3R,4S,5R)-3,4-Dihydroxy-5-(hydroxymethyl)tetrahydro-2-furanyl]-6-[(2,2-diphenylethyl)amino]-9H-purin-2-yl}methyl)-N'-[2-(diisopropylamino)ethyl]urea

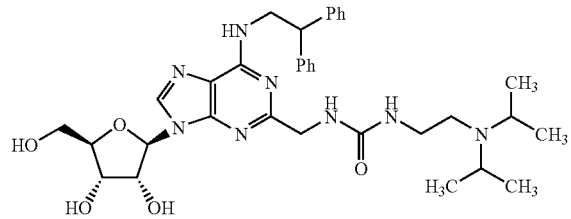

N-[2-(Diisopropylamino)ethyl]-1H-imidazole-1-carboxamide (84 mg, 0.35mmol) (Preparation 27) was added to a stirred solution of (2R,3R,4S,5R)-2-{2-(aminomethyl)-6-[(2,2-diphenylethyl)amino]-9H-purin-9-yl}-5-(hydroxymethyl)tetrahydro-3,4-furandiol (150 mg, 0.35mmol) (Preparation 2) in dichloromethane (5 ml) at room temperature. The reaction was heated under reflux for 1 hour and then toluene (5 ml) and isopropanol (2 ml) were added. The dichloromethane was boiled off and the reaction was then heated under reflux for 1 hour. The reaction mixture was allowed to cool to room temperature and the solvent was removed under reduced pressure. The residue was purified by column chromatography on silica gel eluting with dichloromethane:methanol:0.88 concentrated aqueous ammonia (95:5:0.5 by volume increasing to 80:20:2 by volume). This gave the title compound as a foam (60 mg).

$\delta_H$ (400MHz; CD$_3$OD): 8.05 (1H, s), 7.35–7.20 (8H, m), 7.15–7.10 (2H, m), 5.90–5.85 (1H, m), 4.75–4.70 (1H, m), 4.50–4.45 (1H, m), 4.40–4.20 (5H, m), 4.15–4.10 (1H, m), 3.90–3.80 (1H, m), 3.70–3.65 (1H, m), 3.10–3.00 (2H, m), 3.00–2.90 (2H, m), 2.50–2.40 (2H, m), 1.00–0.90 (12H, m).

Example 2

N-({9-[(2R,3R,4S,5R)-3,4-Dihydroxy-5-(hydroxymethyl)tetrahydro-2-furanyl]-6-[(2,2-diphenylethyl)amino]-9H-purin-2-yl}methyl)-N'-[2-(1-piperidinyl)ethyl]urea

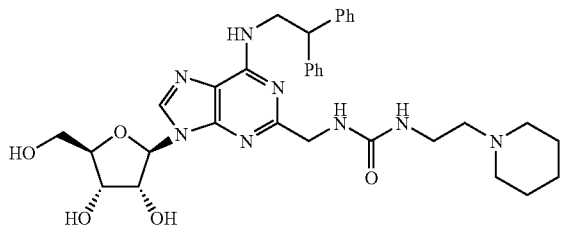

A solution of (2R,3R,4R,5R)-4-(acetyloxy)-2-[(acetyloxy)methyl]-5-(6-[(2,2-diphenylethyl)amino]-2-{[({[2-(1-piperidinyl)ethyl]amino}carbonyl)amino]methyl}-9H-purin-9-yl)tetrahydro-3-furanyl acetate (100 mg, 0.13mmol) (Preparation 6) in methanol (50 ml) was saturated with ammonia gas and then left to stand for 3 hours. The solvent was removed under reduced pressure to give a residue that was purified by elution through a plug of silica gel with dichloromethane: methanol:0.88 concentrated aqueous ammonia (90:10:1 by volume) to give the title compound as a foam (45 mg).

m/z: MH$^+$ 631. $\delta_H$ 400 MHz; CD$_3$OD): 8.15 (1H, s), 7.40–7.15 (10H, m), 6.00–5.90 (1H, m), 4.90–4.70 (signal obscured by HOD in CD$_3$OD), 4.60–4.10 (7H, m), 3.90–3.80 (1H, m), 3.80–3.70 (1H, m), 3.30–3.20 (2H, m), 2.55–2.35 (6H, m), 1.65–1.40 (6H, m).

Example 3

(2S,3S,4R,5R)-5-{2-{[({[2-(Diisopropylamino)ethyl]amino}carbonyl)amino]methyl}-6-[(2,2-diphenylethyl)amino]-9H-purin-9-yl}-N-ethyl-3,4-dihydroxytetrahydro-2-furancarboxamide

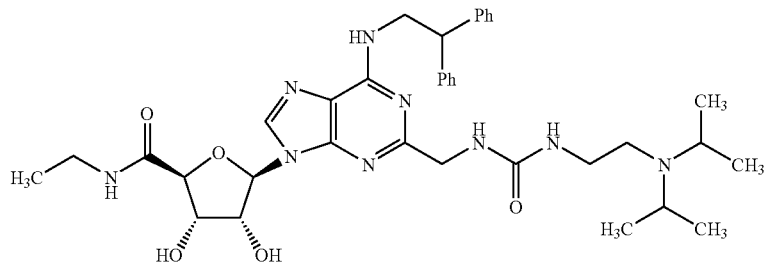

N-[2-(Diisopropylamino)ethyl]-1H-imidazole-1-carboxamide (84 mg, 0.35 mmol) (Preparation 27) was added to a stirred suspension of (2S,3S,4R,5R)-5-{2-(aminomethyl)-6-[(2,2-diphenylethyl)amino]-9H-purin-9-yl}-N-ethyl-3,4-dihydroxytetrahydro-2-furancarboxamide (100 mg, 0.23mmol) (Preparation 11) in dichloromethane (5 ml) at room temperature. The reaction was then heated to reflux and a drop of isopropanol was added to help dissolve the reagents. The reaction mixture was heated under reflux for 20 minutes and then toluene (5 ml) was added. The dichloromethane was boiled off and the reaction was then heated under reflux for 30 minutes. The reaction mixture was allowed to cool to room temperature and the solvent was removed under reduced pressure. The residue was purified by column chromatography on silica gel eluting with dichloromethane:methanol:0.88 concentrated aqueous ammonia (95:5:0.5 by volume increasing to 80:20:2 by volume). The solvent was removed under reduced pressure to give a yellow oil. The oil was dissolved in dichloromethane (2 ml) and diethylether was added to induce crystallisation. Filtration gave the title compound as a white solid (70 mg).

$\delta_H$(400 MHz; CD$_3$OD): 8.20 (1H, s), 7.40–7.10 (10H, m), 6.10–6.00 (1H, m), 4.90–4.80 (1H obscured by HOD in MeOH), 4.55–4.20 (7H, m), 3.40–3.10 (6H, m), 2.75–2.60 (2H, m), 1.20–1.00 (15H, m).

Example 4

(2S,3S,4R,5R)-5-(6-[(2,2-Diphenylethyl)amino]-2-{[({[2-(1-Piperidinyl)ethyl]amino}carbonyl)amino]methyl}-9H-purin-9-yl)-N-ethyl-3,4-dihydroxytetrahydro-2-furancarboxamide

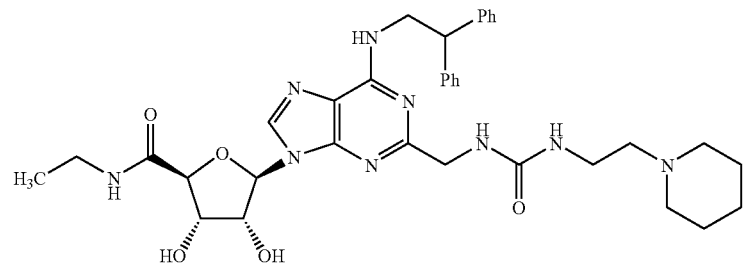

Potassium carbonate (20 mg, 0.14 mmol) was added to a solution of (2S,3S,4R,5R)-4-(benzoyloxy)-5-(6-[(2,2-diphenylethyl)amino]-2-{[({[2-(1-piperidinyl)ethyl]amino}carbonyl)amino]methyl}-9H-purin-9-yl)-2-[(ethylamino) carbonyl]tetrahydro-3-furanyl benzoate (100 mg, 0.13 mmol) (Preparation 14) in methanol (10 ml). The reaction mixture was stirred at room temperature for 2 hours. More potassium carbonate (20 mg, 0.14 mmol) was then added and the reaction mixture was heated to 60° C. for 2 hours. The solvent was removed under reduced pressure to give a residue that was slurried with acetone and filtered. The filtrate was evaporated under reduced pressure and the residue was partially purified by column chromatography on silica gel eluting with dichloromethane:methanol:0.88 concentrated aqueous ammonia (90:10:1 by volume). The residue after solvent evaporation under reduced pressure was repurified by more column chromatography on silica gel eluting with dichloromethane:methanol:0.88 concentrated aqueous ammonia (90:10:1 by volume). The solvent was removed by evaporation under reduced pressure to give the title compound as a foam (17 mg).

m/z: MH$^+$ 673. $\delta_H$ 400 MHz; CD$_3$OD): 8.20 (1H, s), 7.40–7.15 (10H, m), 6.05–6.00 (1H, m), 4.90–4.80 (1H obscured by HOD in MeOH), 4.55–4.20 (7H, m), 3.40–3.20 (4H, m), 2.55–2.40 (6H, m), 1.70–1.50 (4H, m), 1.50–1.40 (2H, m), 1.15–1.05 (3H, m).

Example 5

(2S,3S,4R,5R)-5-{2-{[((E)-(Cyanoimino){[2-(1-piperidinyl)ethyl]amino}methyl)amino]methyl}-6-[(2,2-diphenylethyl)amino]-9H-purin-9-yl}-N-ethyl-3,4-dihydroxytetrahydro-2-furancarboxamide

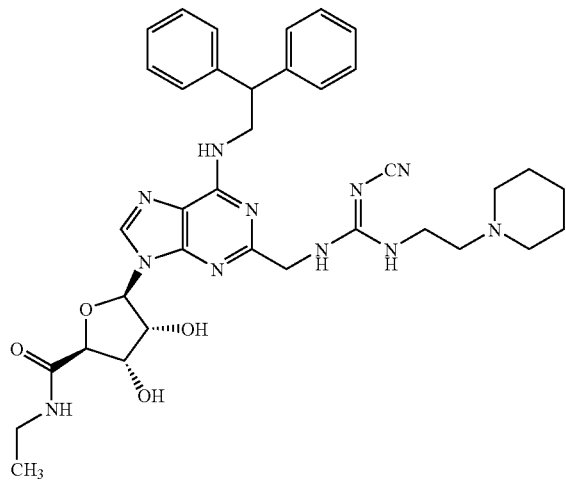

Dimethyl cyanodithioimidocarbonate (77 mg, 0.48 mmol) was added to a solution of (2S,3S,4R,5R)-5-{2-(aminomethyl)-6-[(2,2-diphenylethyl)amino]-9H-purin-9-yl}-N-ethyl-3,4-dihydroxytetrahydro-2-furancarboxamide (250 mg, 0.48 mmol) (Preparation 11) in ethanol (10 ml). The reaction mixture was stirred for 3 hours at room temperature and then 2-aminoethylpiperidine (88μl, 0.68 mmol) was added. The reaction mixture was heated under reflux for 2 hours, more 2-aminoethylpiperidine (0.17 ml, 1.2 mmol) was added and then the reaction mixture was heated under reflux for a further 4 hours. The reaction was cooled and evaporated to dryness and the residue was purified by flash chromatography on silica gel eluting with dichloromethane:methanol (98:2 by volume) increasing in polarity to dichloromethane methanol:0.88 concentrated aqueous ammonia (90:10:1 by volume) to give the title compound (64 mg) a foam.

m/z MH$^+$ 696. $\delta_H$(400 MHz; CDCl$_3$): 8.30 (1H, s), 8.20 (1H, s), 7.85 (1H, s), 7.35–7.05 (10H, m), 6.95 (1H, bs), 5.95–5.85 (1H, m), 5.60–5.55 (1H, m), 5.45–5.40 (1H, m), 4.60–4.45 (2H, m), 4.40–4.35 (1H, m), 4.25–4.20 (1H, m), 4.15–4.00 (3H, m), 3.35–3.05 (4H, m signal partially obscured by HOD in DMSO), 2.40–2.15 (6H, m), 1.40–1.20 (6H, m).

Example 6

(2S,3S,4R,5R)-5-{2-({[(Benzylamino)carbonyl]amino}methyl)-6-[(2,2-diphenylethyl)amino]-9H-purin-9-yl}-N-ethyl-3,4-dihydroxytetrahydro-2-furancarboxamide

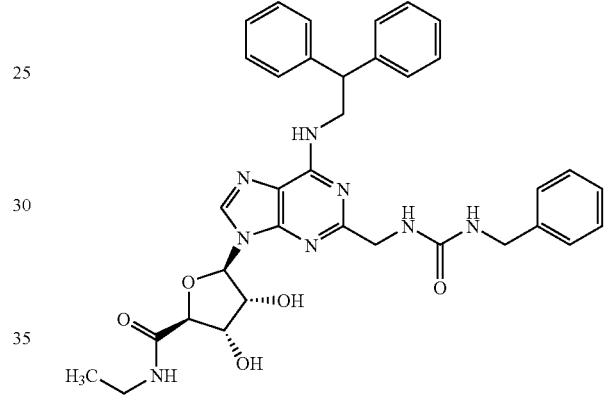

Benzylisocyanate (26 mg, 0.30 mmol) was added to a solution of (2S,3S,4R,5R)-5-{2-(aminomethyl)-6-[(2,2-diphenylethyl)amino]-9H-purin-9-yl}-N-ethyl-3,4-dihydroxytetrahydro-2-furancarboxamide (Preparation 11) in dichloromethane (2 ml). The reaction mixture was stirred for 16 hours at room temperature and allowed to evaporate. Ethanol (2 ml) was added and then aqueous hydrochloric acid (1M, 1 ml) was added. The reaction mixture was stirred at 60° C. for 6 hours, then allowed to cool to room temperature and left for a further 16 h. More aqueous hydrochloric acid (1 M, 0.5 ml) was added and the reaction mixture was stirred at room temperature for a further 4 h. The solvent was removed under reduced pressure and the residue was purified by column chromatography on silica gel eluting with dichloromethane: methanol (95:5 by volume) increasing in polarity to dichloromethane:methanol (90:10 by volume). The material obtained was impure and hence was repurified by column chromatography on silica gel eluting with dichloromethane:methanol (95:5 by volume) increasing in polarity to dichloromethane:methanol (90:10 by volume) to give the title compound as a solid (85 mg).

$\delta_H$ (300 MHz; D$_6$DMSO): 8.35–8.25 (2H, m), 7.80–7.75 (1H, m), 7.40–7.10 (15H, m), 6.80–6.70 (1H, m), 6.40–6.30 (1H, m), 6.00–5.90 (1H, m), 5.65–5.60 (1H, m), 5.50–5.40 (1H, m), 4.65–4.55 (2H, m), 4.35–4.05 (8H, m), 3.25–3.05 (2H, m), 1.05–0.95 (3H, m).

Example 7

(2S,3S,4R,5R)-5-{2-({[(Cyclohexylamino)carbonyl]amino}methyl)-6-[(2,2-diphenylethyl)amino]-9H-purin-9-yl}-N-ethyl-3,4-dihydroxytetrahydro-2-furancarboxamide

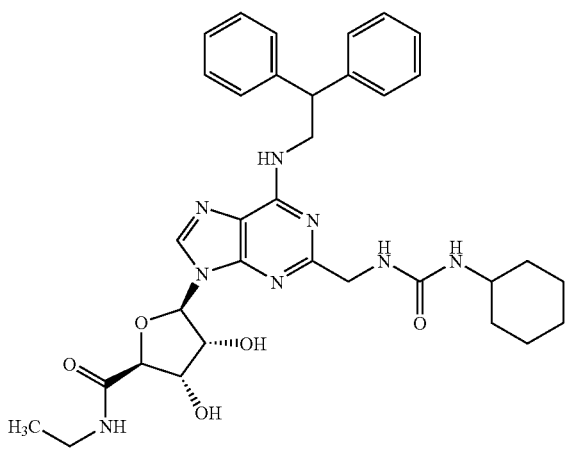

The compound was prepared from cyclohexylisocyanate and (2S,3S,4R,5R)-5-{2-(aminomethyl)-6-[(2,2-diphenylethyl)amino]-9H-purin-9-yl}-N-ethyl-3,4-dihydroxytetrahydro-2-furancarboxamide (Preparation 11) according to the procedure used in Example 6.

m/z MH$^+$ 644. $\delta_H$ (300 MHz; d$_6$DMSO): 8.40–8.20 (2H, m), 7.80–7.70 (1H, m), 7.40–7.05 (10H, m), 6.25–5.85 (3H, m), 5.65–5.55 (1H, m), 5.55–5.40 (1H, m), 4.70–4.45 (2H, m), 4.35–4.00 (5H, m), 3.50–3.00 (3H, m), 1.85–1.40 (5H, m), 1.30–1.00 (8H, m).

Example 8

(2S,3S,4R,5R)-5-{2-({[({2-[Benzoyl(isopropyl)amino]ethyl}amino)carbonyl]amino}methyl)-6-[(2,2-diphenylethyl)amino]-9H-purin-9-yl}-N-ethyl-3,4-dihydroxytetrahydro-2-furancarboxamide

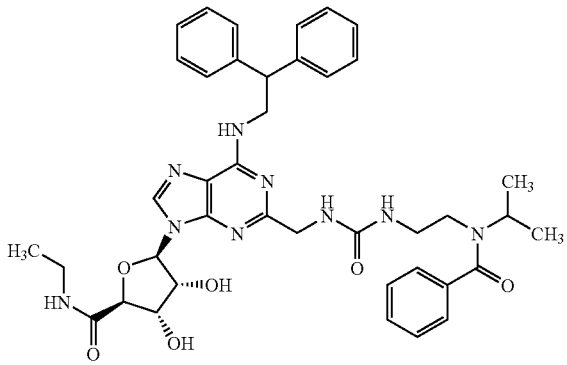

Benzoyl chloride (19 mg, 0.14 mmol) was added to a stirred solution of (2S,3S,4R,5R)-5-(6-[(2,2-diphenylethyl)amino]-2-{[({[2-(isopropylamino) ethyl]amino}carbonyl)amino]methyl}-9H-purin-9-yl)-N-ethyl-3,4-dihydroxytetrahydro-2-furancarboxamide (80 mg, 0.12 mmol) (Preparation 12) and triethylamine (0.034 ml, 0.25 mmol) in ethyl acetate (5 ml) and N'-methylpyrrolidinone (0.2 ml) at room temperature. The reaction mixture was stirred for 96 hours, washed with water (2 ml) and evaporated under reduced pressure. The residue was purified by column chromatography on silica gel eluting with dichloromethane:methanol:0.88 concentrated aqueous ammonia (90:10:1 by volume) increasing in polarity to dichloromethane:methanol:0.88 concentrated aqueous ammonia (80:20:3 by volume) to give the title compound as a foam (35 mg).

m/z MH$^+$ 787. $\delta_H$ (400 MHz; CD$_3$OD): 8.20 (1H, s), 7.50–7.15 (15H, m), 6.05–6.00 (1H, m), 4.90–4.80 (1H, m), 4.55–4.20 (7H, m), 3.95–3.85 (1H, m), 3.50–3.20 (6H, m), 1.20–1.00 (9H, m).

Example 9

(2S,3S,4R,5R)-5-[6-[(2,2-Diphenylethyl)amino]-2-({[({2-[isopropyl(phenylsulfonyl)amino]ethyl}amino)carbonyl]amino}methyl)-9H-purin-9-yl]-N-ethyl-3,4-dihydroxytetrahydro-2-furancarboxamide

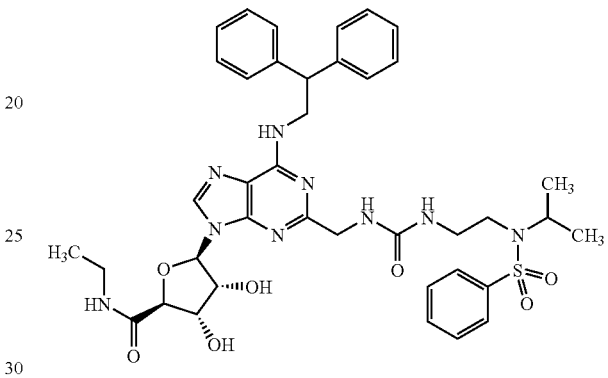

The title compound was prepared from (2S,3S,4R,5R)-5-(6-[(2,2-diphenylethyl)amino]-2-{[({[2-(isopropylamino)ethyl]amino}carbonyl)amino]methyl}-9H-purin-9-yl)-N-ethyl-3,4-dihydroxytetrahydro-2-furancarboxamide (80 mg, 0.12 mmol) (Preparation 12) and benzenesulphonyl chloride (0.0017 ml, 0.14 mmol) by a similar method to that of Example 8.

m/z MH$^+$ 787. $\delta_H$ (400 MHz; CD$_3$OD): 8.15 (1H, s), 7.80–7.75 (2H, m), 7.60–7.50 (1H, m), 7.50–7.40 (2H, m), 7.30–7.15 (8H, m), 7.15–7.05 (2H, m), 6.05–5.95 (1H, m), 4.50–4.30 (5H, m), 4.30–4.20 (2H, m), 4.05–3.95 (1H, m), 3.40–3.20 (4H, m), 3.0–3.10 (2H, m), 1.10–1.00 (3H, m), 1.00–0.90 (6H, m).

Example 10

NA-({9-[(2R,3R,4S,5R)-3,4-Dihydroxy-5-(hydroxymethyl)tetrahydro-2-furanyl]-6-[(2,2-diphenylethyl) amino]-9H-purin-2-yl}methyl)-N-methyl-N-[2-(2-pyridinyl)ethyl]urea

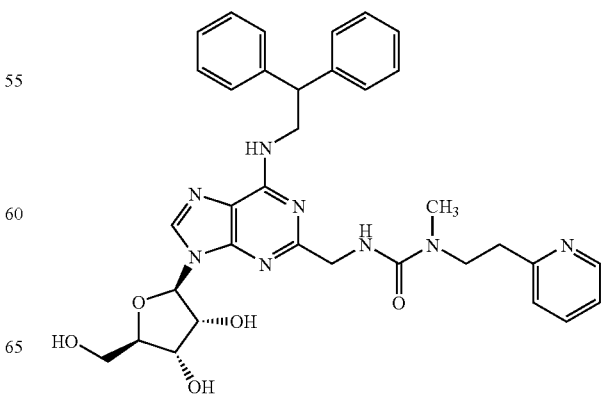

N,O-Bistrimethylsilylacetamide (0.5 ml, 2.02 mmol) was added to a suspension of N'-({6-[(2,2-diphenylethyl)amino]-9H-purin-2-yl}methyl)-N-methyl-N-[2-(2-pyridinyl) ethyl] urea (0.16 g, 0.31 mol) (Preparation 26) in 1,1,1-trichloroethane (15 ml). The suspension was heated to reflux. When all suspended solid had dissolved the reaction mixture was allowed to cool to room temperature and the solvent was removed under reduced pressure. The residue was twice dissolved in toluene (50 ml) and the solvent was removed under reduced pressure. The residue was then dissolved in toluene (15 ml) and (2R,3R,4R,5S)-4,5-bis(acetyloxy)-2-[(acetyloxy)methyl]tetrahydro-3-furanyl acetate (0.112 g, 0.36 mol) was added. The solution was stirred at room temperature and trimethylsilyltrifluoromethanesulphonate (0.17 ml, 0.94 mmol) was added. The resulting solution was heated under reflux for 2 hours and then allowed to cool to room temperature. The reaction mixture was diluted by the addition of ethyl acetate (75 ml) and then washed with saturated aqueous sodium hydrogen carbonate solution (two portions of 30 ml) and saturated aqueous sodium chloride solution (30 ml). The organic layer was dried over anhydrous magnesium sulphate. The solvent was removed under reduced pressure to give a solid that was purified by column chromatography on silica gel eluting with dichloromethane:methanol:0.88 concentrated aqueous ammonia (97:3:0.5 by volume). This material was dissolved in methanol (50 ml) and a stream of ammonia gas was passed through the solution until it was saturated. The solution was allowed to stand at room temperature for 4 hours. The solvent was removed under reduced pressure to give a residue that was purified by flash chromatography on silica gel eluting with dichloromethane:methanol:0.88 concentrated aqueous ammonia (90:10:1 by volume) to give the title compound (0.05 g) as a white solid.

m/z MH$^+$ 639. $\delta_H$ (300 MHz; CD$_3$OD): 8.45–8.40 (1H, m), 8.10 (1H, s), 7.75–7.65 (1H, m), 7.35–7.10 (11H, m), 5.95–5.90 (1H, m), 4.80–4.75 (1H, m), 4.50–4.40 (3H, m), 4.40–4.20 (3H, m), 4.20–4.15 (1H, m), 3.90–3.85 (1H, m), 3.75–3.70 (1H, m), 3.60–3.45 (2H, m), 3.00–2.90 (2H, m), 2.80 (3H, s).

Examples 11–28

The following Examples were prepared by a similar method to that of Example 3 using the stated starting materials.

| Example Number | Structure (starting materials) | $^1$H-NMR (400 MHz) | LRMS (electrospray): m/z |
|---|---|---|---|
| 11 | 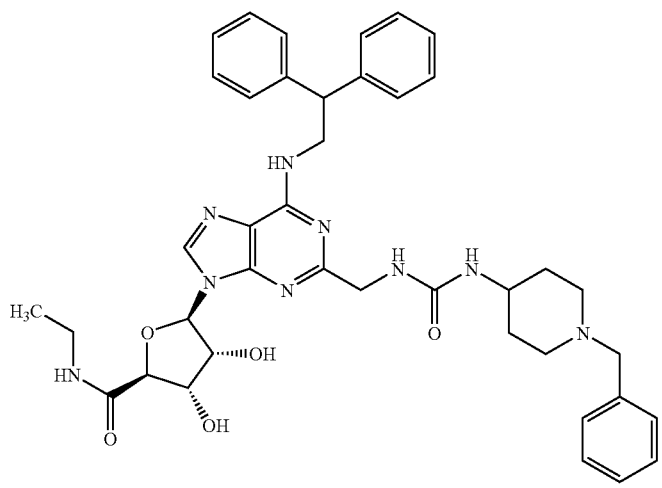<br>(Preparations 11 and 34) | $\delta_H$ (300MHz; CD$_3$OD): 8.20 (1H, s), 7.40–7.20 (15H, m), 7.20–7.10 (2H, m), 6.10–6.00 (1H, m), 4.55–4.20 (7H, m), 3.60–3.05 (3H, m), 2.90–2.80 (2H, m), 2.20–2.10 (2H, m), 1.90–1.80 (2H, m), 1.55–1.40 (2H, m), 1.15–1.05 (3H, m). | |

| Example Number | Structure (starting materials) | $^1$H-NMR (400 MHz) | LRMS (electrospray): m/z |
|---|---|---|---|
| 12 | 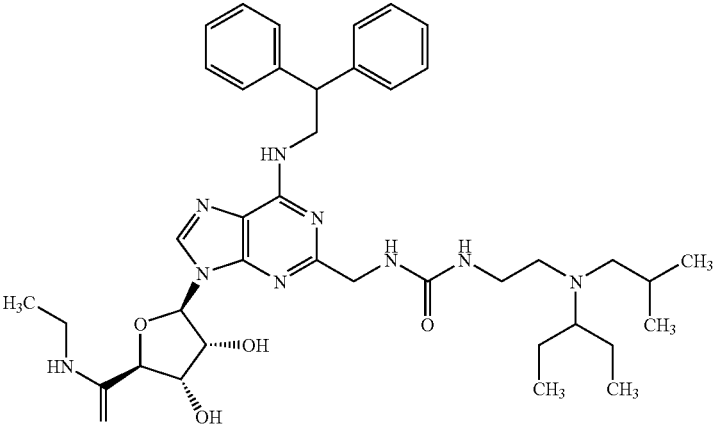<br>(Preparations 11 and 48) | $\delta_H$ (300MHz; CD$_3$OD): 8.20 (1H, s), 7.40–7.25 (8H, m), 7.25–7.15 (2H, m), 6.05–6.00 (1H, m), 4.60–4.25 (7H, m), 3.40–3.20 (2H, m), 3.20–3.05 (2H, m), 2.65–2.40 (4H, m), 2.40–2.20 (1H, m), 1.70–1.55 (1H, m), 1.55–1.25 (6H, m), 1.15–1.05 (3H, m), 1.00–0.80 (12H, m). | |
| 13 | 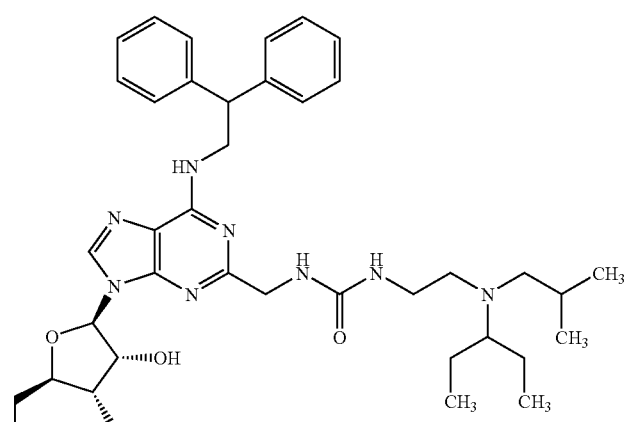<br>(Preparations 2 and 48) | $\delta_H$ (400MHz; CD$_3$OD): 8.05 (1H, s), 7.35–7.20 (8H, m), 7.20–7.10 (2H, m), 5.90–5.85 (1H, m), 4.75–4.70 (1H, m), 4.50–4.45 (1H, m), 4.40–4.20 (5H, m), 4.10 (1H, s), 3.90–3.80 (1H, m), 3.70–3.65 (1H, m), 3.10–3.00 (2H, m), 2.50–2.35 (4H, m), 2.25–2.20 (1H, m), 1.60–1.50 (1H, m), 1.50–1.30 (2H, m), 1.30–1.20 (4H, m), 0.90–0.80 (12H, m). | [MH$^+$] 703 |
| 14 | 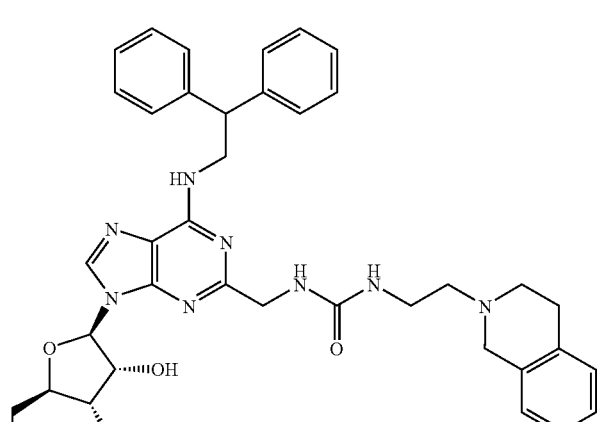<br>(Preparations 2 and 36) | $\delta_H$ (400MHz; CD$_3$OD): 8.10 (1H, s), 7.40–6.90 (14H, m), 5.95–5.85 (1H, m), 4.80–4.70 (1H, m), 4.50–4.10 (7H, m), 3.90–3.80 (1H, m), 3.75–3.70 (1H, m), 3.70–3.60 (2H, m), 3.40–3.25 (2H, m), 2.90–2.80 (2H, m), 2.90–2.65 (2H, m), 2.65–2.55 (2H, m). | [MH$^+$] 679 |

| Example Number | Structure (starting materials) | $^1$H-NMR (400 MHz) | LRMS (electrospray): m/z |
|---|---|---|---|
| 15 | 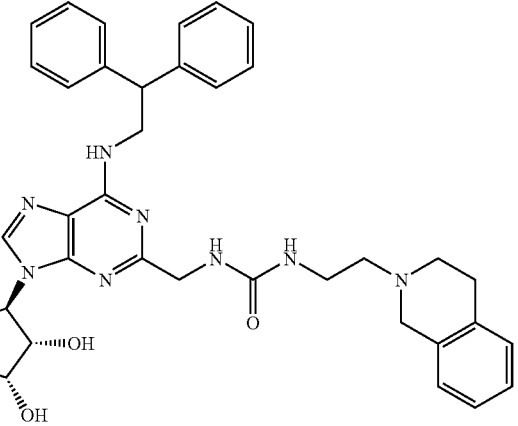<br>(Preparations 11 and 36) | δ$_H$ (400MHz; CD$_3$OD): 8.10 (1H, s), 7.40–6.90 (14H, m), 5.95–5.85 (1H, m), 4.80–4.70 (1H, m), 4.50–4.10 (7H, m), 3.90–3.80 (1H, m), 3.75–3.70 (1H, m), 3.70–3.60 (2H, m), 3.40–3.25 (2H, m), 2.90–2.80 (2H, m), 2.80–2.65 (2H, m), 2.65–2.55 (2H, m). | [MH$^+$] 720 |
| 16 | 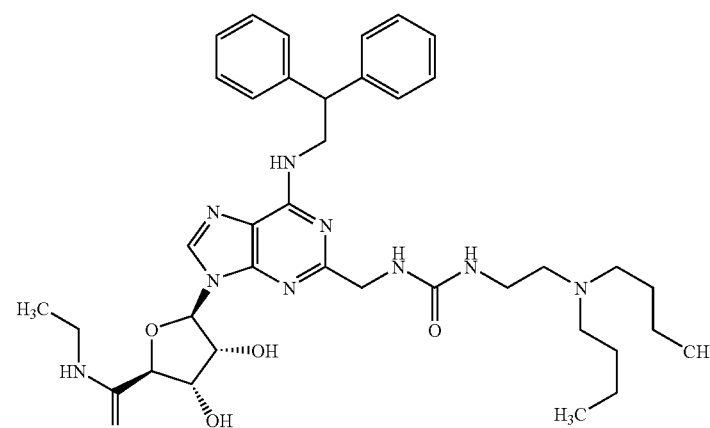<br>(Preparations 11 and 33) | δ$_H$ (400MHz; CD$_3$OD): 8.20 (1H, s), 7.35–7.25 (8H, m), 7.20–7.10 (2H, m), 6.05–6.00 (1H, m), 4.55–4.30 (5H, m), 4.30–4.20 (2H, m), 3.40–3.20 (4H, m), 2.70–2.60 (2H, m), 2.60–2.50 (4H, m), 1.50–1.40 (4H, m), 1.40–1.25 (4H, m), 1.10–1.05 (3H, m), 0.95–0.85 (6H, m). | [MH$^+$] 716 |
| 17 | 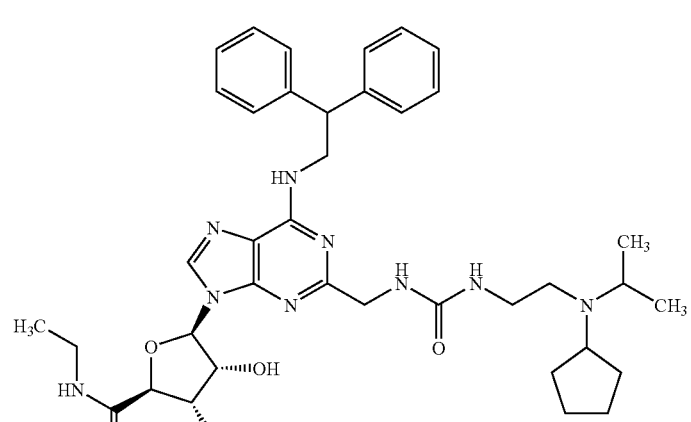<br>(Preparations 11 and 29) | δ$_H$ (300MHz; CD$_3$OD): 8.20 (1H, s), 7.40–7.25 (8H, m), 7.20–7.15 (2H, m), 6.05–6.00 (1H, m), 4.55–4.35 (7H, m), 4.35–4.20 (2H, m), 3.45–3.25 (2H, m), 3.25–3.00 (4H, m), 2.60–2.50 (2H, m), 1.85–1.75 (2H, m), 1.70–1.30 (6H, m), 1.20–1.10 (3H, m), 1.05–1.00 (6H, m). | [MH$^+$] 714 |

| Example Number | Structure (starting materials) | $^1$H-NMR (400 MHz) | LRMS (electrospray): m/z |
|---|---|---|---|
| 18 | 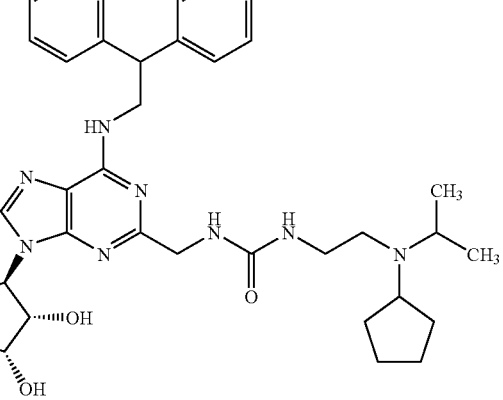<br>(Preparations 2 and 29) | $\delta_H$ (400MHz; CDCl$_3$): D$_2$O exchange. 7.60 (1H, s), 7.35–7.15 (10H, m), 5.70–5.65 (1H, m), 4.90–4.80 (1H, m), 4.50–4.10 (6H, m), 3.90–3.85 (1H, m), 3.75–3.65 (1H, m), 3.10–3.05 (2H, m), 3.05–2.95 (2H, m), 2.55–2.45 (2H, m), 1.80–1.65 (2H, m), 1.65–1.50 (2H, m), 1.50–1.40 (2H, m), 1.40–1.25 (2H, m), 1.00–0.90 (6H, m). | [MH$^+$] 673 |
| 19 | 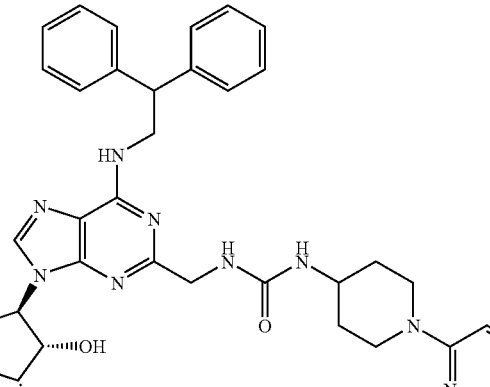<br>(Preparations 11 and 31) | $\delta_H$ (400MHz; CD$_3$OD): 8.15–8.10 (1H, m), 8.05–8.00 (1H, m), 7.50–7.40 (1H, m), 7.30–7.15 (8H, m), 7.15–7.05 (2H, m), 6.75–6.70 (1H, m), 6.60–6.50 (1H, m), 6.00–5.95 (1H, m), 4.45–3.95 (8H, m), 3.75–3.65 (1H, m), 3.35–3.20 (2H, m), 2.95–2.85 (2H, m), 1.90–1.80 (2H, m), 1.40–1.30 (2H, m), 1.10–1.00 (3H, m). | [MH$^+$] 721 |
| 20 | 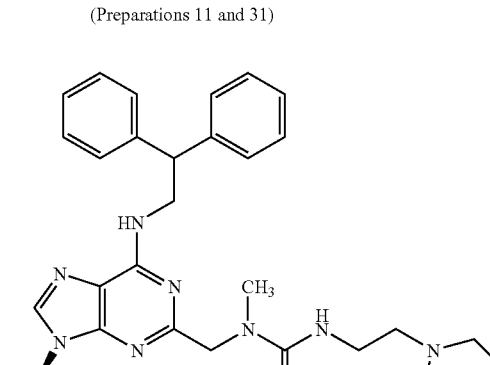<br>(Preparations 72 and 73) | $\delta_H$ (400MHz; CD$_3$OD): 8.20–810 (1H, m), 7.35–7.20 (8H, m), 7.20–7.10 (2H, m), 6.05–5.95 (1H, m), 4.80–4.70 (1H, m), 4.60–4.40 (3H, m), 4.40–4.30 (2H, m), 4.30–4.15 (2H, m), 3.40–3.20 (5H, m), 3.10–3.00 (2H, m), 2.40–2.25 (6H, m), 1.60–1.45 (4H, m), 1,45–1.35 (2H, m), 1.15–1.00 (3H, m). | [MH$^+$] 686 |

| Example Number | Structure (starting materials) | ¹H-NMR (400 MHz) | LRMS (electrospray): m/z |
|---|---|---|---|
| 21 | 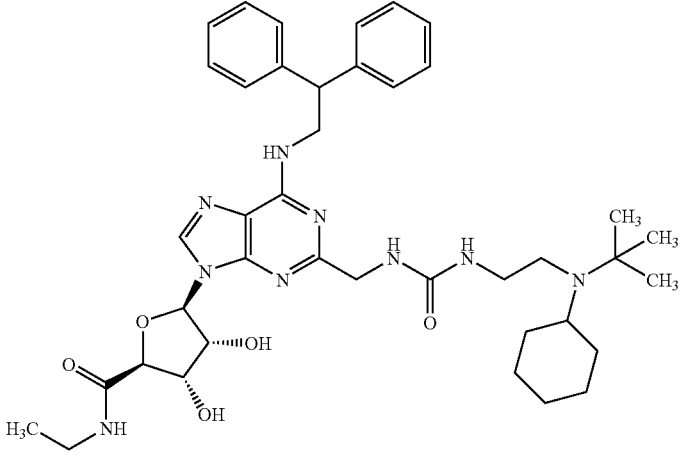<br>(Preparations 11 and 32) | δ_H (400MHz; CD₃OD): 8.20–8.15 (1H, m), 7.35–7.20 (8H, m), 7.20–7.10 (2H, m), 6.05–6.00 (1H, m), 4.55–4.30 (5H, m), 4.30–4.20 (2H, m), 3.40–3.20 (2H, m), 3.10–3.05 (2H, m), 2.90–2.80 (1H, m), 2.70–2.65 (2H, m), 1.75–1.60 (4H, m), 1.60–1.50 (1H, m), 1.40–1.20 (4H, m), 1.20–1.00 (13H, m). | [MH⁺] 742 |
| 22 | 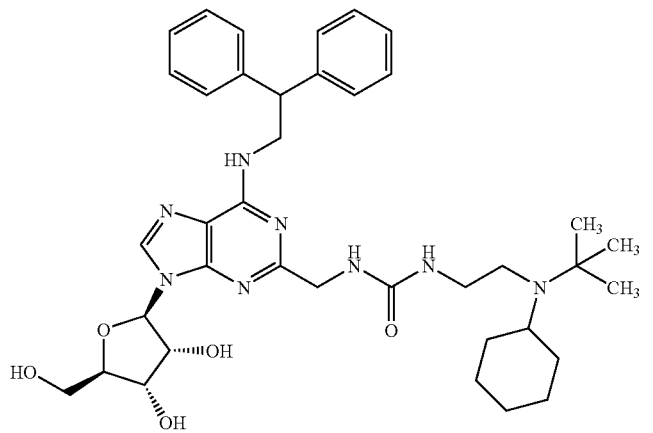<br>(Preparations 2 and 32) | δ_H (400MHz; CD₃OD): 8.10–8.05 (1H, m), 7.35–7.20 (8H, m), 7.20–7.10 (2H, m), 5.95–5.90 (1H, m), 4.80–4.70 (1H, m), 4.55–4.10 (7H, m), 3.90–3.80 (1H, m), 3.75–3.70 (1H, m), 3.10–3.05 (2H, m), 2.90–2.80 (1H, m), 2.70–2.65 (1H, m), 1.75–1.60 (4H, m), 1.60–1.50 (1H, m), 1.40–1.20 (4H, m), 1.10 (9H, s), 1.10–0.95 (1H, m). | |
| 23 | 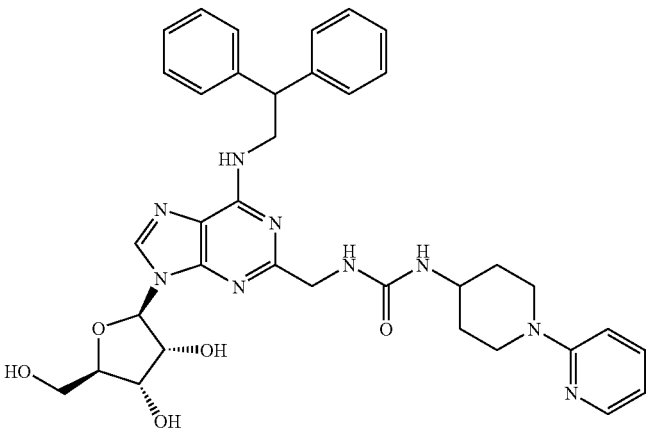<br>(Preparations 2 and 31) | δ_H (400MHz; CD₃OD): 8.05–8.00 (2H, m), 7.50–7.40 (1H, m), 7.30–7.25 (4H, m), 7.25–7.15 (4H, m), 7.10–7.05 (2H, m), 6.75–6.70 (1H, m), 6.60–6.55 (1H, m), 5.90–5.85 (1H, m), 4.75–4.70 (1H, m), 4.50–4.40 (1H, m), 4.40–4.35 (1H, m), 4.30–4.25 (1H, m), 4.25–4.20 (1H, m), 4.10 (1H, s), 4.05–4.00 (2H, m), 3.85–3.80 (1H, m), 3.70–3.65 (2H, m), 2.90–2.85 (2H, m), 1.90–1.80 (2H, m), 1.40–1.25 (2H, m). | [MH⁺] 680 |

| Example Number | Structure (starting materials) | ¹H-NMR (400 MHz) | LRMS (electrospray): m/z |
|---|---|---|---|
| 24 | (Preparations 2 and 35) | δ_H (400MHz; CD₃OD): 8.10 (1H, s), 7.30–7.20 (13H, m), 7.20–7.10 (2H, m), 5.95–5.90 (1H, m), 4.75–4.70 (1H, m), 4.50–4.45 (1H, m), 4.40–4.20 (6H, m), 4.10 (1H, s), 3.90–3.80 (1H, m), 3.75–3.70 (1H, m), 3.45 (2H, m), 3.00–2.95 (2H, m), 2.85–2.80 (2H, m), 1.95–1.90 (2H, m), 1.65–1.60 (2H, m), 1.45–1.35 (1H, m), 1.25–1.10 (2H, m). | [MH⁺] 707 |
| 25 | (Preparations 11 and 35) | δ_H (400MHz; CDCl₃): D₂O exchanged 7.80 (1H, s), 7.20–7.05 (13H, m), 7.05–7.00 (2H, m), 5.80–5.75 (1H, m), 4.70–4.65 (1H, m), 4.50–4.45 (1H, m), 4.35–4.20 (4H, m), 4.20–4.05 (2H, m), 3.40–3.45 (2H, m), 3.25–3.15 (1H, m), 3.10–3.00 (1H, m), 2.95–2.80 (2H, m), 2.80–2.70 (2H, m), 1.90–1.80 (2H, m), 1.55–1.45 (2H, m), 1.35–1.25 (1H, m), 1.20–1.05 (2H, m), 0.95–0.90 (3H, m). | [MH⁺] 748 |
| 26 | (Preparations 11 and 30) | δ_H (400MHz; CD₃OD): 8.10–8.05 (1H, m), 7.50–7.40 (2H, m), 7.30–7.15 (7H, m), 7.15–7.05 (3H, m), 6.05–5.95 (1H, m), 4.85–4.80 (1H, m), 4.50–4.30 (5H, m), 4.30–4.20 (2H, m), 3.35–3.20 (2H, m), 3.20–3.10 (2H, m), 2.80–2.60 (3H, m), 1.35–1.30 (6H, m), 1.10–1.00 (3H, m), 0.90–0.80 (6H, m). | [MH⁺] 765 |

| Example Number | Structure (starting materials) | $^1$H-NMR (400 MHz) | LRMS (electrospray): m/z |
|---|---|---|---|
| 27 | 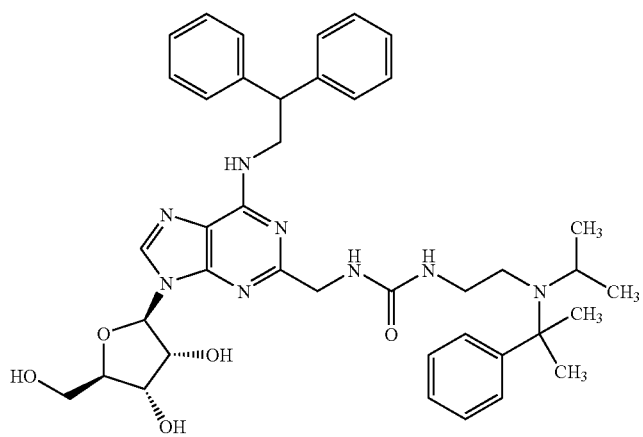<br>(Preparations 2 and 30) | $\delta_H$ (400MHz; CD$_3$OD): 8.05 (1H, s), 7.35–7.20 (12H, m), 7.20–7.10 (3H, m), 6.10–6.05 (1H, m), 4.75–4.70 (1H, m), 4.50–4.40 (1H, m), 4.35–4.20 (5H, m), 4.10–4.05 (1H, m), 3.90–3.75 (2H, m), 3.70–3.60 (3H, m), 0.95–0.90 (3H, m), 0.85–0.80 (3H, m). | |
| 28 | 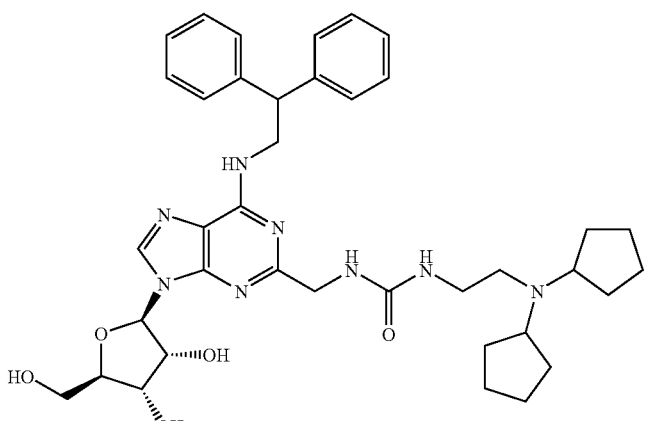<br>(Preparations 2 and 37) | $\delta_H$ (400MHz; CDCl$_3$): 7.50 (1H, s), 7.30–7.10 (10H, m), 5.70–5.60 (1H, m), 4.45–4.35 (1H, m), 4.35–4.20 (3H, m), 4.20–4.15 (1H, m), 4.15–4.00 (1H, m), 3.90–3.80 (1H, m), 3.70–3.60 (1H, m), 3.15–2.95 (3H, m), 2.50–2.40 (2H, m), 1.70–1.60 (4H, m), 1.60–1.45 (4H, m), 1.45–1.35 (4H, m), 1.35–1.20 (4H, m). | [MH$^+$] 699 |

Example 29

N-({9-[(2R,3R,4S,5R)-3,4-Dihydroxy-5-(hydroxymethyl)tetrahydro-2-furanyl]-6-[(9H-fluoren-9-ylmethyl)amino]-9H-purin-2-yl}methyl)-N'-[2-(diisopropylamino)ethyl]urea

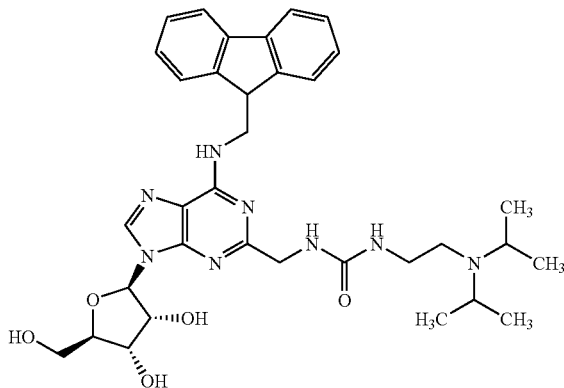

The title compound was prepared from (2R,3R,4S,5R)-2-{2-(aminomethyl)-6-[(9H-fluoren-9-ylmethyl)amino]-9H-purin-9-yl}-5-(hydroxymethyl)tetrahydro-3,4-furandiol (Preparation 13) and N-[2-(diisopropylamino)ethyl]-1H-imidazole-1-carboxamide (Preparation 27) in a similar procedure to Example 3.

m/z MH$^+$ 645. $\delta_H$ (400 MHz; CD$_3$OD): 8.20 (1H, m), 7.85–7.75 (2H, m), 7.70–7.60 (2H, m), 7.40–7.20 (4H, m), 6.00–5.90 (1H, m), 4.40–4.35 (1H, m), 4.35–4.30 (1H, m), 4.20–4.00 (3H, m), 3.90–3.70 (4H, m).

Example 30

N-({9-[(2R,3R,4S,5R)-3,4-Dihydroxy-5-(hydroxymethyl)tetrahydro-2-furanyl]-6-[(2,2-diphenylethyl)amino]-9H-purin-2-yl}methyl)-N'-[2-(2,2,6,6-tetramethyl-1-piperidinyl)ethyl]urea

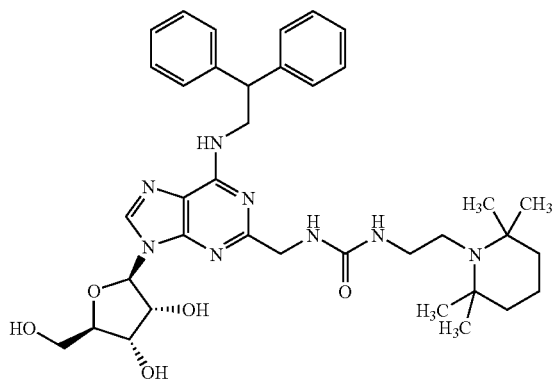

2-(2,2,6,6-Tetramethyl-1-piperidinyl)ethanamine (0.11 g, 0.6 mmol) (Preparation 43) was added to a stirred solution of N'N'-carbonyldiimidazole in tetrahydrofuran (5 ml) at room temperature. The reaction mixture was stirred for 16 hours at room temperature. The solvent was evaporated and the residue was dissolved in ethyl acetate (30 ml). The resulting solution was washed with water (20 ml) and dried over anhydrous sodium sulphate. The solvent was evaporated to give impure N-[2-(2,2,6,6-tetramethyl-1-piperidinyl)ethyl]-1H-imidazole-1-carboxamide as a gum. This crude material (83 mg, 0.3 mmol) was added to a stirred solution of (2R,3R,4S,5R)-2-{2-(aminomethyl)-6-[(2,2-diphenylethyl)amino]-9H-purin-9-yl}-5-(hydroxymethyl)tetrahydro-3,4-furandiol (100 mg, 0.21 mmol) (Preparation 2) in toluene (5 ml) and isopropanol (1 ml) at room temperature. The reaction mixture was heated under reflux for 3 hours and then allowed to cool to room temperature. The solvent was evaporated under reduced pressure to give a residue that was purified by column chromatography on silica gel eluting with dichloromethane:methanol 0.88 concentrated aqueous ammonia (95:5:0.5 by volume) increasing in polarity to dichloromethane:methanol:0.88 concentrated aqueous ammonia (90:10:1 by volume). The solvent was evaporated under reduced pressure to give a residue that was found to still be impure. The residue was repurified by column chromatography on silica gel eluting with dichloromethane:methanol:0.88 concentrated aqueous ammonia (95:5:0.5 by volume) increasing in polarity to dichloromethane:methanol:0.88 concentrated aqueous ammonia (90:10:1 by volume). The solvent was removed under reduced pressure to give the title compound (22 mg) as a gum.

m/z MH$^+$ 686. $\delta_H$ (400 MHz; CD$_3$OD): 8.10 (1H, s), 7.35–7.20 (8H, m), 7.20–7.10 (2H, m), 5 5.95–5.90 (1H, m), 4.75–4.70 (1H, m), 4.55–4.45 (1H, m), 4.45–4.20 (5H, m), 4.20–4.10 (1H, m), 3.90–3.85 (1H, m), 3.75–3.70 (1H, m), 3.15–3.05 (2H, m), 2.60–2.55 (2H, m), 1.60–1.50 (2H, m), 1.45–1.40 (4H, m), 1.05 (12H, s).

Example 31

(2S,3S,4R,5R)-5-(6-[(2,2-Diphenylethyl)amino]-2-{[({[2-(4-isopropyl-1-piperidinyl)ethyl]amino}carbonyl)amino]methyl}-9H-purin-9-yl)-N-ethyl-3,4-dihydroxytetrahydro-2-furancarboxamide

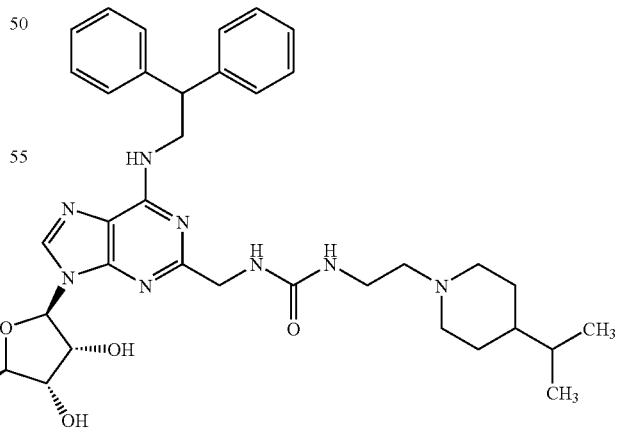

2-(4-Isopropyl-1-piperidinyl)ethylamine (0.3 g, 1.76 mmol) (Preparation 57) was added to a stirred solution of N'N'-carbonyldiimidazole (0.295 g, 1.82 mmol) in tetrahydrofuran (15 ml). The reaction mixture was stirred for two hours. The solvent was removed under reduced pressure and the residue was partitioned between ethyl acetate (40 ml) and water (20 ml). The organic layer was dried over anhydrous sodium sulphate and the solvent was removed to give impure N-[2-(4-isopropyl-1-piperidinyl)ethyl]-1H-imidazole-1-carboxamide (Preparation 28). This crude material was added to a solution of (2S,3S,4R,5R)-5-{2-(aminomethyl)-6-[(2,2-diphenylethyl)amino]-9H-purin-9-yl}-N-ethyl-3,4-dihydroxytetrahydro-2-furancarboxamide (130 mg, 0.25 mmol) (Preparation 11) in toluene (3 ml) and isopropyl alcohol (1 ml) at room temperature. The reaction mixture was heated under reflux for 3 hours. The solvent was removed under reduced pressure and the residue was purified by column chromatography eluting with dichloromethane:methanol:0.88 concentrated aqueous ammonia (95:5:0.5 by volume) increasing in polarity to dichloromethane:methanol:0.88 concentrated aqueous ammonia (80:20:3 by volume). The solvent was removed under reduced pressure to give a residue that was impure. The material was triturated with diethylether (5 ml) three times. The insoluble solid was repurified by column chromatography eluting with dichloromethane:methanol:0.88 concentrated aqueous ammonia (95:5:0.5 by volume) increasing in polarity to dichloromethane:methanol:0.88 concentrated aqueous ammonia (90:10:1 by volume). The solvent was removed under reduced pressure to give the title compound (37 mg) as a foam.

m/z MH$^+$ 714. $\delta_H$ (400 MHz; CD$_3$OD): 8.20 (1H, s), 7.40–7.20 (8H, m), 7.20–7.10 (2H, m), 6.05–6.00 (1H, m), 4.55–4.20 (7H, m), 3.40–3.20 (4H, m), 3.05–2.85 (2H, m), 2.50–2.35 (2H, m), 2.00–1.85 (2H, m), 1.70–1.60 (2H, m), 1.45–1.20 (3H, m), 1.10–0.95 (4H, m), 0.95–0.80 (6H, m).

Example 32

(2S,3S,4R,5R)-5-(6-[(2,2-Diphenylethyl)amino]-2-{[({[2-(2,2,6,6-tetramethyl-1-piperidinyl)ethyl]amino}carbonyl)amino]methyl}-9H-purin-9-yl)-N-ethyl-3,4-dihydroxytetrahydro-2-furancarboxamide The title compound was prepared by a similar procedure to that used in Example 30 using (2S,3S,4R,5R)-5-{2-(aminomethyl)-6-[(2,2-diphenylethyl)amino]-9H-purin-9-yl}-N-ethyl-3,4-dihydroxytetrahydro-2-furancarboxamide (Preparation 11) and 2-(2,2,6,6-tetramethyl-1-piperidinyl)ethanamine (Preparation 43).

m/z MH$^+$ 728. $\delta_H$ (400 MHz; CD$_3$OD): 8.20 (1H, s), 7.15–7.10 (4H, m), 7.10–7.05 (4H, m), 7.20–7.15 (2H, m), 6.05–6.00 (1H, m), 4.55–4.40 (5H, m), 4.35–4.20 (2H, m), 3.40–3.20 (2H, m), 3.15–3.05 (2H, m), 2.65–2.55 (2H, m), 1.60–1.50 (2H, m), 1.45–1.40 (4H, m), 1.15–1.05 (3H, m), 1.05–1.00 (12H, m).

Example 33

N-[(3R)-1-Benzylpyrrolidinyl]-N'-({9-[(2R,3R,4S,5R)-3,4-dihydroxy-5-(hydroxymethyl)tetrahydro-2-furanyl]-6-[(2,2-diphenylethyl)amino]-9H-purin-2-yl}methyl)urea (3R)-1-Benzyl-3-pyrrolidinamine (0.64 ml, 3.4 mmol) was added to a stirred solution of N'N'-carbonyldiimidazole (0.6 g, 3.7 mmol) in dichloromethane (150 ml) at room temperature. The reaction mixture was stirred at room temperature for 1 hour. Dichloromethane (100 ml) was added and the solution then washed three times with water (50 ml). The organic phase was washed twice with saturated aqueous sodium chloride solution and then dried over anhydrous magnesium sulphate. The solvent was removed under reduced pressure to give N-[(3R)-1-benzylpyrrolidinyl]-1H-imidazole-1-carboxamide (1.23 g) as an impure oil. This material (115 mg, 0.43 mmol) was added to a stirred solution of (2R,3R,4S,5R)-2-{2-(aminomethyl)-6-[(2,2-diphenylethyl)amino]-9H-purin-9-yl}-5-(hydroxymethyl)tetrahydro-3,4-furandiol (Preparation 2) (100 mg, 0.21 mmol) in toluene (10 ml) and isopropanol (2.5 ml) at room temperature. The reaction mixture was heated under reflux for 40 minutes and then allowed to cool to room temperature. The solvent was removed under reduced pressure and the residue was purified by column chromatography eluting with dichloromethane:methanol:0.88 concentrated aqueous ammonia (95:5:0.5 by volume) increasing in polarity to dichloromethane:methanol:0.88 concentrated aqueous ammonia (90:10:1 by volume). The solvent was removed under reduced pressure to give the title compound (138 mg).

$\delta_H$ (400 MHz; CD$_3$OD): 8.10 (1H, s), 7.30–7.20 (13H, m), 7.20–7.10 (2H, m), 5.90–5.85 (1H, m), 4.80–4.75 (1H, m), 4.50–4.45 (1H, m), 4.45–4.10 (7H, m), 3.90–3.85 (1H, m), 3.75–3.70 (1H, m), 3.60–3.50 (2H, m), 2.75–2.65 (2H, m), 2.50–2.40 (2H, m), 2.20–2.10 (1H, m), 1.60–1.50 (1H, m).

Example 34

(2S,3S,4R,5R)-5-{2-{[({[(3R)-1-Benzylpyrrolidinyl]amino}carbonyl)amino]methyl}-6-[(2,2-diphenylethyl)amino]-9H-purin-9-yl}-N-ethyl-3,4-dihydroxytetrahydro-2-furancarboxamide

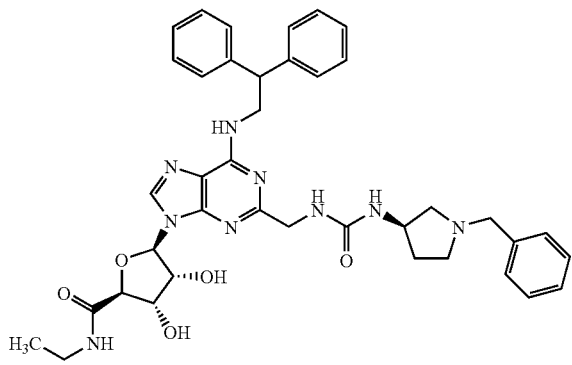

The title compound was prepared by a similar method to that of Example 33 using (2S,3S,4R,5R)-5-{2-(aminomethyl)-6-[(2,2-diphenylethyl)amino]-9H-purin-9-yl}-N-ethyl-3,4-dihydroxytetrahydro-2-furancarboxamide (Preparation 11) and (3R)-1-benzyl-3-pyrrolidinamine.

$\delta_H$ (400 MHz; CD$_3$OD): 8.15 (1H, s), 7.35–7.20 (13H, m), 7.20–7.10 (2H, m), 6.05–6.00 (1H, m), 4.85–4.80 (1H, m), 4.55–4.10 (7H, m), 3.60–3.50 (2H, m), 3.40–3.20 (2H, m), 2.80–2.60 (2H, m), 2.50–2.35 (2H, m), 2.20–2.10 (1H, m), 1.65–1.45 (1H, m), 1.15–1.00 (3H, m).

Example 35

(2S,3S,4R,5R)-5-(6-{[2,2-Bis(4-chlorophenyl)ethyl]amino}-2-{[({[2-(diisopropylamino)ethyl]amino}carbonyl)amino]methyl}-9H-purin-9-yl)-N-ethyl-3,4-dihydroxytetrahydro-2-furancarboxamide

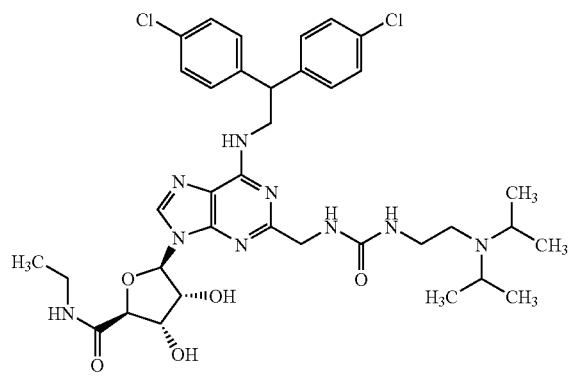

(2R,3R,4S,5S)-4-(Benzoyloxy)-2-(6-{[2,2-bis(4-chlorophenyl)ethyl]amino}-2-cyano-9H-purin-9-yl)-5-[(ethylamino)carbonyl]tetrahydro-3-furanyl benzoate (220 mg, 0.28 mmol) (Preparation 68) was added to a saturated solution of ammonia in ethanol (15 ml). 10% Palladium on carbon (40 mg) was added and the suspension was stirred under an atmosphere of hydrogen gas (413.7 kPa, 60 psi) at room temperature for 16 hours. The reaction temperature was then stirred at 60° C. under an atmosphere of hydrogen gas (413.7 kPa, 60 psi) for a further 48 hours. The reaction mixture was filtered through Arbocel (Trade Mark) and the solvent was removed under reduced pressure. The crude residue was dissolved in toluene (8 ml) and isopropyl alcohol (2 ml) and N-[2-(diisopropylamino)ethyl]-1H-imidazole-1-carboxamide (50 mg, 0.21 mmol) (Preparation 27) were added. The solution was heated under reflux for 3 hours. The solvent was removed under reduced pressure and the residue was purified by column chromatography on silica gel eluting with dichloromethane methanol:0.88 concentrated aqueous ammonia (90:10:2 by volume). The solvent was removed under reduced pressure give a product that was contaminated with imidazole. The product was dissolved in dichloromethane (60 ml) and the resulting solution was washed three times with water (10 ml) and dried over anhydrous magnesium sulphate. The solvent was removed under reduced pressure to give the title compound (53 mg) as a foam.

m/z MH$^+$ 756. $\delta_H$ (400 MHz; CD$_3$OD): 8.20 (1H, s), 7.40–7.20 (8H, m), 6.05–6.00 (1H, m), 4.55–4.20 (7H, m), 3.40–3.25 (2H, m), 3.20–3.05 (4H, m), 1.15–1.00 (15H, m).

Example 36

N-({6-{[2,2-Bis(4-chlorophenyl)ethyl]amino}-9-[(2R,3R,4S,5R)-3,4-dihydroxy-5-(hydroxymethyl)tetrahydro-2-furanyl]-9H-purin-2-yl}methyl)-N'-[2-(diisopropylamino)ethyl]urea

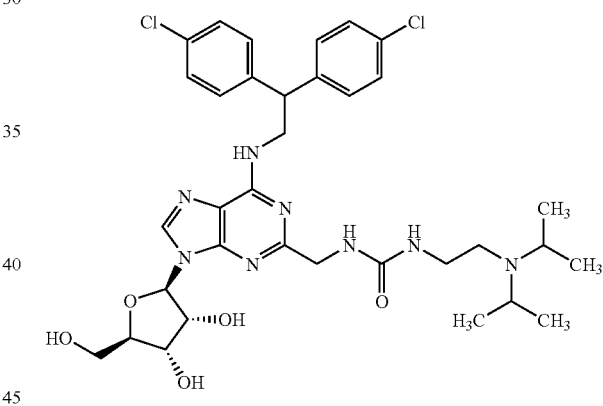

(2R,3R,4S,5R)-2-(2-(Aminomethyl)-6-{[2,2-bis(4-chlorophenyl)ethyl]amino}-9H-purin-9-yl)-5-(hydroxymethyl)tetrahydro-3,4-furandiol (0.1 g, 0.18 mmol) (Preparation 63) was dissolved in a mixture of isopropanol (0.5 ml) and Genklene (Trade Mark) (5 ml). N-[2-(Diisopropylamino)ethyl]-1H-imidazole-1-carboxamide (48 mg, 0.20 mmol) (Preparation 27) was added and the reaction mixture was heated under reflux for 2 hours. More N-[2-(diisopropylamino)ethyl]-1H-imidazole-1-carboxamide (35 mg, 0.15 mmol) (Preparation 27) was then added and the reaction mixture was heated under reflux for a further 2 hours. The reaction mixture was then allowed to cool and the solvent was removed under reduced pressure. The residue was purified by flash chromatography on silica gel eluting with dichloromethane:methanol:0.88 concentrated aqueous ammonia (95:5:0.5 by volume) increasing in polarity to dichloromethane:methanol:0.88 concentrated aqueous ammonia (90:10:2 by volume) to give the title compound (0.09 g) as a gum.

m/z MH$^+$ 715. $\delta_H$ (400 MHz; CD$_3$OD): 8.10 (1H, s), 7.35–7.20 (8H, m), 7.20–7.15 (1H, m), 5.90–5.85 (1H, m), 4.75–4.70 (1H, m), 4.55–4.45 (1H, m), 4.40–4.35 (2H, m), 4.35–4.15 (3H, m), 4.15–4.10 (1H, m), 3.90–3.80 (1H, m), 3.70–3.65 (1H, m), 3.25–3.10 (2H, m), 1.20–1.00 (12H, m).

Example 37

N-({6-{[2,2-Bis(4-methylphenyl)ethyl]amino}-9-[(2R,3R,4S,5R)-3,4-dihydroxy-5-(hydroxymethyl)tetrahydro-2-furanyl]-9H-purin-2-yl}methyl)-N'-[2-(diisopropylamino)ethyl]urea

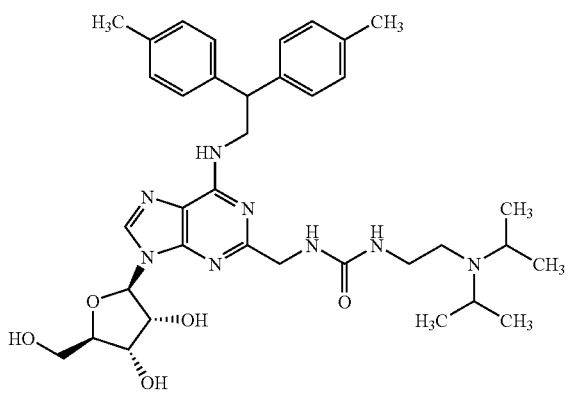

The title compound was prepared from (2R,3R,4S,5R)-2-(2-(aminomethyl)-6-{[2,2-bis(4-methyl phenyl)ethyl]amino}-9H-purin-9-yl )-5-(hydroxymethyl)tetrahydro-3,4-furandiol (Preparation 60) and N-[2-(diisopropylamino)ethyl]-1H-imidazole-1-carboxamide (Preparation 27) using a similar procedure to that used in Example 36.

m/z MH$^+$ 673. $\delta_H$ (400 MHz; CD$_3$OD): 8.05 (1H, s), 7.20–7.15 (4H, m), 7.05–7.00 (4H, m), 5.90–5.85 (1H, m), 4.75–4.70 (1H, m), 4.40–4.30 (3H, m), 4.30–4.25 (1H, m), 4.15-4.10 (1H, m), 3.90–3.80 (1H, m), 3.75–3.70 (1H, m), 3.10–3.05 (2H, m), 3.05–2.90 (2H, m), 2.50–2.45 (2H, m), 2.05 (6H, m), 1.00–0.95 (12H, m).

Example 38

N-({6-{[2,2-Bis(3-chlorophenyl)ethyl]amino}-9-[(2R,3R,4S,5R)-3,4-dihydroxy-5-(hydroxymethyl)tetrahydro-2-furanyl]-9H-purin-2-yl}methyl)-N'-[2-(diisopropylamino)ethyl]urea

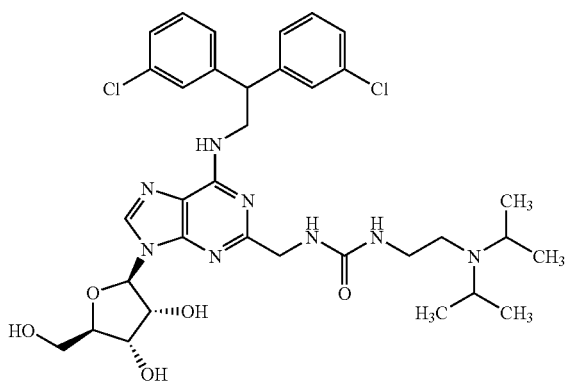

The title compound was prepared from (2R,3R,4S,5R)-2-(2-(aminomethyl)-6-{[2,2-bis(4-methyl phenyl)ethyl]amino}-9H-purin-9-yl )-5-(hydroxymethyl)tetrahydro-3,4-furandiol (Preparation 62) and N-[2-(diisopropylamino)ethyl]-1H-imidazole-1carboxamide (Preparation 27) in a similar procedure to that used in Example 36.

m/z MH$^+$ 715. $\delta_H$ (400 MHz; CD$_3$OD): 8.10–8.05 (1H, m), 7.35–7.10 (8H, m), 5.90–5.85 (1H, m), 4.75–4.70 (1H, m), 4.60–4.45 (1H, m), 4.40–4.15 (5H, m), 4.10–4.05 (1H, m), 3.85–3.80 (1H, m), 3.70–3.65 (1H, m), 3.15–3.00 (4H, m), 2.65–2.50 (2H, m), 1.05–0.90 (1 2H, m).

Example 39

N-({6-{[2,2-Bis(3-chlorophenyl)ethyl]amino}-9-[(2R,3R,4S,5R)-3,4-dihydroxy-5-(hydroxymethyl)tetrahydro-2-furanyl]-9H-purin-2-yl}methyl)-N'-[2-(diisopropylamino)ethyl]urea

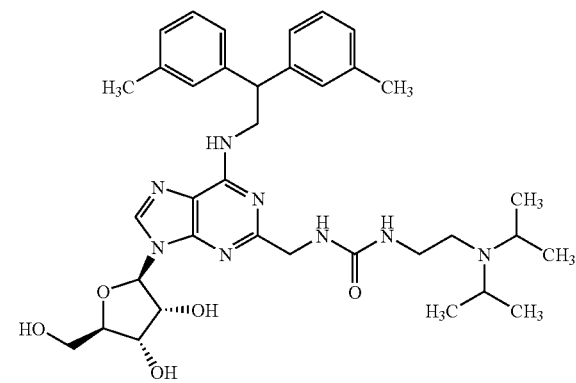

The title compound was prepared from (2R,3R,4S,5R)-2-(2-(aminomethyl)-6-{[2,2-bis(3-methylphenyl)ethyl]amino}-9H-purin-9-yl)-5-(hydroxymethyl)tetrahydro-3,4-furandiol (Preparation 65) and N-[2-(diisopropylamino)ethyl]-1H-imidazole-1-carboxamide (Preparation 27) using a similar procedure to that used in Example 36.

m/z MH$^+$ 673. $\delta_H$ (400 MHz; CD$_3$OD): 8.10 (1H, s), 7.20–7.05 (6H, m), 5.90–5.85 (1H, m), 4.75–4.70 (1H, m), 4.40–4.25 (5H, m), 4.25–4.15 (2H, m), 4.15–4.10 (1H, m), 3.90–3.80 (1H, m), 3.70–3.65 (1H, m), 3.15–3.00 (4H, m), 2.60–2.45 (2H, m), 2.05 (6H, s), 1.10–0.95 (12H, m).

Example 40

(2S,3S,4R,5R)-5-{2-{[({[2-(Diisopropylamino)ethyl]amino}carbonyl)amino]methyl}-6-[(1-naphthylmethyl)amino]-9H-purin-9-yl}-N-ethyl-3,4-dihydroxytetrahydro-2-furancarboxamide

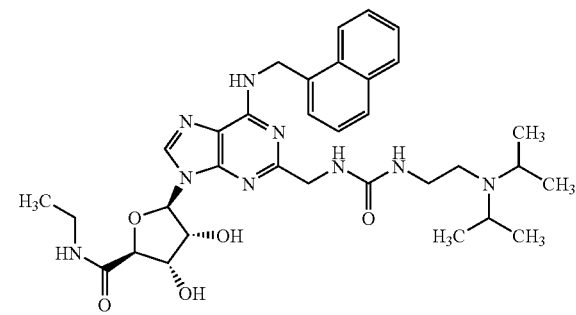

The title compound was prepared from (2S,3S,4R,5R)-5-{2-(aminomethyl)-6-[(1-naphthylmethyl)amino]-9H-purin-9-yl}-N-ethyl-3,4-dihydroxytetrahydro-2-furancarboxamide (Preparation 69) and N-[2-(diisopropylamino)ethyl]-1H-imidazole-1-carboxamide (Preparation 27) by similar procedure to that used in Example 3.

m/z MH[30] 648. $\delta_H$ (400 MHz; CD$_3$OD): 8.20 (1H, s), 8.15–8.10 (1H, m), 7.90–7.85 (1H, m), 7.80–7.75 (1H, m), 7.55–7.50 (1H, m), 7.50–7.45 (1H, m), 7.45–7.40 (1H, m), 6.05–6.00 (1H, m), 5.35–5.25 (2H, m), 4.45–4.35 (4H, m), 3.35–3.20 (2H, m), 3.10–3.00 (2H, m), 3.00–2.90 (2H, m), 2.50–2.40 (2H, m), 1.10–1.05 (3H, m).

The following Preparations describe the preparation of certain intermediates used in the preceding Examples.

Preparation 1

(2R,3R,4R,5R)-4-(Acetyloxy)-2-[(acetyloxy)methyl]-5-{2-cyano-6-[(2,2-diphenylethyl)amino]-9H-purin-9-yl}tetrahydro-3-furanyl acetate

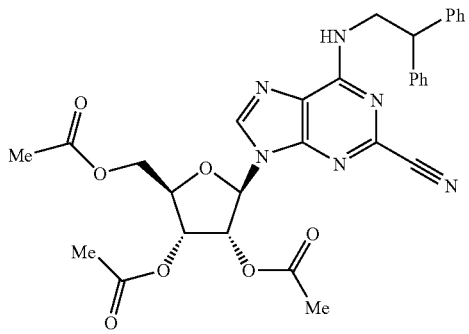

N,O-Bistrimethylsilylacetamide (44 ml, 0.18 mol) was added to a suspension of 6-[(2,2-diphenylethyl)amino]-9H-purine-2-carbonitrile (10.0 g, 0.03 mol) (Preparation 24) in 1,1,1-trichloroethane (250 ml). The suspension was heated under reflux. When all suspended solid had dissolved the reaction mixture was allowed to cool to room temperature and the solvent was removed under reduced pressure. The residue was twice dissolved in toluene (50 ml) and the solvent was removed under reduced pressure. The residue was then dissolved in toluene (100 ml) and (2R,3R,4R,5S)-4,5-bis(acetyloxy)-2-[(acetyloxy)methyl]tetrahydro-3-furanyl acetate (10.3 g, 0.032 mol) was added. The solution was stirred at room temperature and trimethylsilyltrifluoromethanesulphonate (16 ml, 0.088 mol) was carefully added. The resulting solution was heated under reflux for 2 hours and then allowed to cool to room temperature. The reaction mixture was diluted by the addition of ethyl acetate (100 ml) and then washed with saturated aqueous sodium hydrogen carbonate solution (ten portions of 100 ml) and saturated aqueous sodium chloride solution (100 ml). The aqueous extracts were combined and washed with ethyl acetate (three portions of 100 ml). The combined organic layers were dried (anhydrous magnesium sulphate) and the solvent was removed under reduced pressure to give a solid that was purified by column chromatography on silica gel eluting with dichloromethane:methanol:0.88 concentrated aqueous ammonia (97:3:0.5 by volume increasing to 80:20:3 by volume). This gave the title compound as a foam (8.5 g).

$\delta_H$ (4 MHz; CDCl$_3$): 7.95 (1H, s), 7.35–7.20 (10H, m), 6.15–6.10 (1H, m), 5.95–5.90 (1H, m), 5.80–5.75 (1H, m), 5.60–5.55 (1H, m), 4.45–4.35 (4H, m), 4.35–4.25 (2H, m), 2.15 (3H, s), 2.10 (3H, s), 2.05 (3H, s).

Preparation 2

(2R,3R,4S,5R)-2-{2-(Aminomethyl)-6-[(2,2-diphenylethyl)amino]-9H-purin-9-yl}-5-(hydroxymethyl)tetrahydro-3,4-furandiol

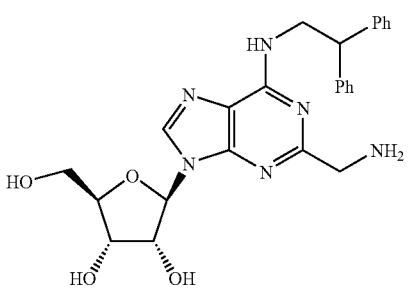

10% Palladium on carbon (200 mg) was added to a solution of (2R,3R,4R,5R)-4-(acetyloxy)-2-[(acetyloxy)methyl]-5-{2-cyano-6-[(2,2-diphenylethyl)amino]-9H-purin-9-yl}tetrahydro-3-furanyl acetate (Preparation 1) (1.9 g, 3.2 mmol) in a saturated solution of ammonia in ethanol (100 ml). The reaction mixture was stirred under an atmosphere of hydrogen (414 kPa, 60 psi) for 16 hours at room temperature. The solids were removed by filtration through Arbocel (Trade Mark) and the solvent was removed under reduced pressure. The residue was purified by column chromatography on silica gel eluting with dichloromethane:methanol 0.88 concentrated aqueous ammonia (90:10:1 by volume increasing to 80:20:2 by volume). This gave the title compound as a solid (770 mg).

m/z: MH$^+$477. $\delta_H$ (4MHz; CDCl$_3$): 8.10 (1H, s), 7.35–7.20 (8H, m), 5.90–5.85 (1H, m), 4.75–4.70 (1H, m), 4.50–4.40 (1H, m), 4.30–4.20 (2H, m), 4.10 (1H, m), 3.90–3.80 (2H, m), 3.70–3.65 (1H, m).

Preparation 3

2-(Aminomethyl)-N-(2,2-diphenylethyl)-9-tetrahydro-2H-pyran-2-yl-9H-purin-6-amine

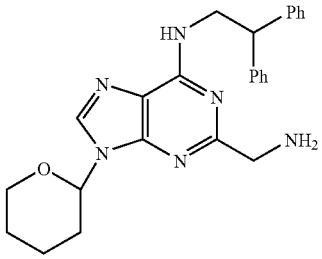

6-[(2,2-Diphenylethyl)amino]-9-(tetrahydro-2H-pyran-2-yl)-9H-purine-2-carbonitrile (19.7 g, 0.046 mol) (Preparation 23) was dissolved in a saturated solution of ammonia in ethanol (500 ml). 10% Palladium on carbon (2 g) was added and the suspension was stirred under an atmosphere of hydrogen (414 kPa, 60 psi) for 36 hours. The suspension was filtered through Arbocel (Trade Mark) and the solvent was removed under reduced pressure. This gave the title compound as a foam (17.7 g).

δ$_H$ (4MHz; CDCl$_3$): 7.84 (1H, s), 7.36–7.14 (10H, m), 5.70 (1H, d), 5.60 (1H, br s), 4.42–4.20 (3H, m), 4.14 (1H, d), 3.95 (2H, s), 3.78 (1H, t), 2.20–1.90 (5H, m), 1.88–1.50 (3H, m).

Preparation 4

N-({6-[(2,2-Diphenylethyl)amino]-9-tetrahydro-2H-pyran-2-yl-9H-purin-2-yl}methyl)-N'-[2-(1-piperidinyl)ethyl]urea

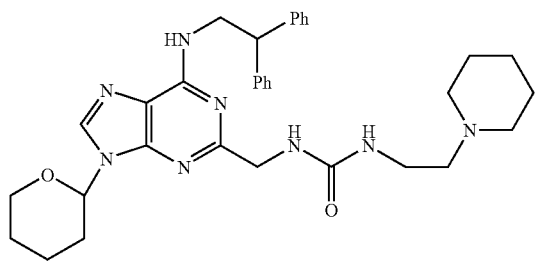

2-(1-Piperidinyl)ethanamine (0.35mi, 2.46 mmol) was added to a solution of N,N'-carbonyldiimidazole (420 mg, 2.6 mmol) in dichloromethane (100 ml). The reaction mixture was stirred for ten minutes at room temperature and then 2-(aminomethyl)-N-(2,2-diphenylethyl)-9-tetrahydro-2H-pyran-2-yl-9H-purin-6-amine (1.0 g, 2.33 mmol) (Preparation 3) was added. The reaction mixture was then stirred for 3 hours at room temperature. Dichloromethane (50 ml) was then added and the resulting solution was washed with water (50 ml) and saturated aqueous sodium chloride solution (50 ml). The organic layer was dried with anhydrous magnesium sulphate and the solvent was removed under reduced pressure. The residue was purified by column chromatography on silica gel eluting with dichloromethane:methanol:0.88 concentrated aqueous ammonia (93:7:1 by volume). This gave the title compound as an oil (300 mg).

m/z: MH$^+$ 583. δ$_H$ (400 MHz; CDCl$_3$): 7.85 (1H, s), 7.55 (1H, s), 7.30–7.05 (10H, m), 5.70–5.60 (1H, m), 4.50–4.00 (6H, m), 3.75–3.60 (1H, m), 3.30–3.10 (2H, m), 2.45–2.20 (6H, m), 2.05–1.85 (2H, m), 1.85–1.25 (10H, m).

Preparation 5

N-({6-[(2,2-Diphenylethyl)amino]-9H-purin-2-yl}methyl)-N'-[2-(1-piperidinyl)ethyl]urea

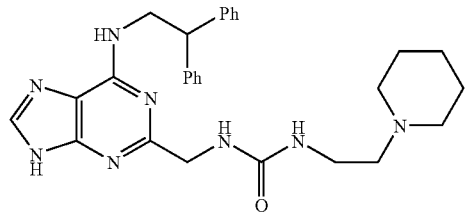

A solution of N-({6-[(2,2-diphenylethyl)amino]-9-tetrahydro-2H-pyran-2-yl-9H-purin-2-yl}methyl)-N'-[2-(1-piperidinyl)ethyl]urea (300 mg, 0.51 mmol) (Preparation 4) in methanol (150 ml) was treated with aqueous hydrochloric acid (2M, 100 ml). The reaction mixture was stirred at room temperature for 2 hours. The solvent volume was then reduced to 100 ml by evaporation under reduced pressure. Saturated aqueous sodium hydrogen carbonate solution (50 ml) and ethyl acetate (200 ml) were added. The two phases were separated. The organic layer was washed with saturated aqueous sodium chloride solution (100 ml), dried (anhydrous magnesium sulphate) and evaporated to give the title compound as a solid (255 mg).

m/z: MH$^+$ 499. δ$_H$ (400 MHz; CDCl$_3$): 7.80 (1H, s), 7.35–7.10 (10H, m), 4.55–4.10 (5H, m), 3.40–3.20 (2H, m), 2.60–2.30 (6H, m), 1.60–1.25 (6H, m).

Preparation 6

(2R,3R,4R,5R)-4-(Acetyloxy)-2-[(acetyloxy)methyl]-5-(6-[(2,2-diphenylethyl) amino]-2-{[({[2-(1-piperidinyl)ethyl]amino}carbonyl)amino]methyl}-9H-purin-9-yl)tetrahydro-3-furanyl acetate

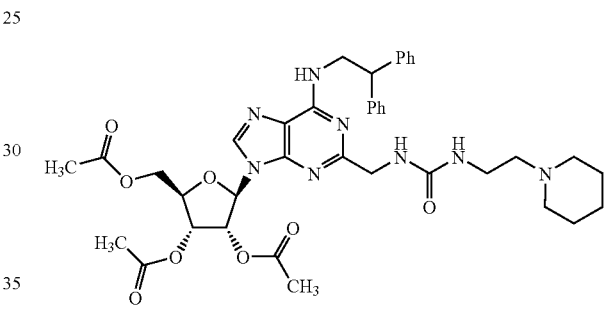

N,O-Bistrimethylsilylacetamide (0.34 ml, 1.4 mmol) was added to a stirred suspension of N-({6-[(2,2-diphenylethyl) amino]-9H-purin-2-yl}methyl)-N'-[2-(1-piperidinyl) ethyl] urea (100 mg, 0.2 mmol) (Preparation 5) in 1,1,1-trichloroethane (20 ml) at 50° C. The reaction mixture was stirred at this temperature for 30 minutes, allowed to cool to room temperature and then evaporated under reduced pressure. Toluene (5 ml) was added and the solvent was removed under reduced pressure. The residue was redissolved in toluene (20 ml) and (2R,3R,4R,5S)-4,5-bis(acetyloxy)-2-[(acetyloxy)methyl]tetrahydro-3-furanyl acetate (0.064 g, 0.2 mmol) and then trimethylsilyltrifluoromethanesulphonate (0.1 ml, 0.35 mmol) were added. The reaction mixture was then heated under reflux for 2 hours. The reaction was allowed to cool to room temperature and diluted with ethyl acetate (100 ml). The solution was washed with saturated aqueous sodium hydrogen carbonate solution (50 ml) and saturated aqueous sodium chloride solution (50 ml) and then dried over anhydrous magnesium sulphate. The solvent was removed to give a residue that was purified by column chromatography on silica gel eluting with dichloromethane:methanol:0.88 concentrated aqueous ammonia (90:10:1 by volume) to give the title compound as an oil (100 mg).

m/z: MH$^+$ 757. δ$_H$ (400 MHz; CDCl$_3$): 7.65 (1H, s), 7.35–7.15 (1 OH, m), 6.05–6.00 (1H, m), 6.00–5.90 (2H, m), 5.85–5.75 (1H, m), 5.45–5.40 (1H, m), 4.60–4.15 (7H, m), 3.35–3.25 (2H, m), 2.50–2.35 (6H, m), 2.15 (3H, s), 2.10 (3H, s), 1.90 (3H, s), 1.60–1.35 (6H, m).

Preparation 7

(2S,3S,4R,5R)-4-(Benzoyloxy)-5-{2-cyano-6-[(2,2-diphenylethyl)amino]-9H-purin-9-yl}-2-[(ethylamino)carbonyl]tetrahydro-3-furanyl benzoate

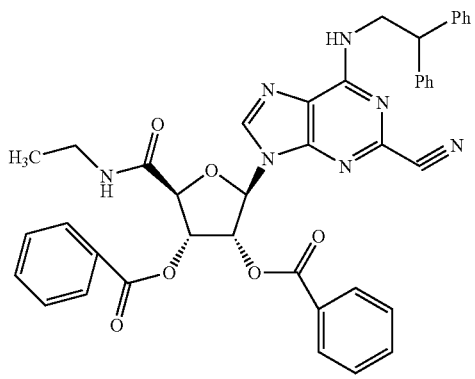

A mixture of 6-[(2,2-diphenylethyl)amino]-9H-purine-2-carbonitrile (Preparation 24) (5.00 g, 14.7 mmol), (2S,3S,4R,5R)-5-(acetyloxy)-4-(benzoyloxy)-2-[(ethylamino)carbonyl]tetrahydro-3-furanyl benzoate and (2S,3S,4R,5S)-5-(acetyloxy)-4-(benzoyloxy)-2-[(ethylamino)carbonyl]tetrahydro-3-furanyl benzoate (Preparation 18) (6.50 g, 14.7 mmol) and iodine (0.38 g, 15.0 mmol) were heated together at 150° C. under reduced pressure (7 kPa, 1 psi) for 2.5 hours. The reaction was then allowed to stand at room temperature for 18 hours. The residue was purified by column chromatography on silica gel eluting with a gradient system of ethyl acetate: pentane (40:60 by volume) increasing in polarity to neat ethyl acetate to afford the title compound as a foam (4.95 g).

$\delta_H$ (400 MHz; CDCl$_3$): 8.12 (3H, m), 7.79 (3H, m), 7.63 (1H, m), 7.50 (3H, m), 7.38–7.16 (11H, m), 6.35 (2H, m), 6.10 (1H, t), 6.03 (1H, d), 4.94 (1H, m), 4.35 (3H, m), 3.57 (2H, m), 1.30 (3H, t).

Preparation 8

(2S,3S,4R,5R)-5-{2{Cyano-6-[(2,2-diphenylethyl)amino]-9H-purin-9-yl}-N-ethyl-3,4-dihydroxytetrahydro-2-furancarboxamide

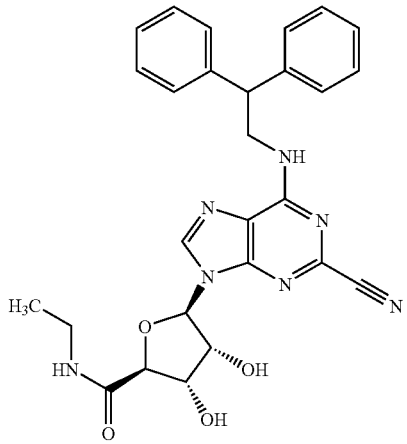

A solution of (2S,3S,4R,5R)-4-(benzoyloxy)-5-{2-cyano-6-[(2,2-diphenylethyl) amino]-9H-purin-9-yl}-2-[(ethylamino)carbonyl]tetrahydro-3-furanyl benzoate (Preparation 7) (4.75 g, 6.59 mmol) in ethanol (200 ml) was saturated with ammonia gas and stirred at room temperature for 18 hours. The solvent was removed under reduced pressure and the residue was purified by column chromatography on silica gel eluting with a gradient system of dichloromethane:methanol (95:5 by volume) gradually changing to dichloromethane:methanol (90:10 by volume) to afford the title compound as a solid (2.80 g).

$\delta_H$ (400 MHz; d$_6$DMSO): 8.65 (1H, s), 8.54 (1H, br t), 8.18 (1H, br m), 7.13–7.42 (10H, m), 5.98 (1H, m), 5.65 (1H, m), 5.57 (1H, m), 4.59 (2H, m), 4.32 (1H, m), 4.08–4.28 (3H, m), 3.20 (2H, m), 1.05 (3H, t).

Preparation 9
2-Chloro-N-(1-naphthylmethyl)-9-tetrahydro-2H-pyran-2-yl-9H-purin-6-amine

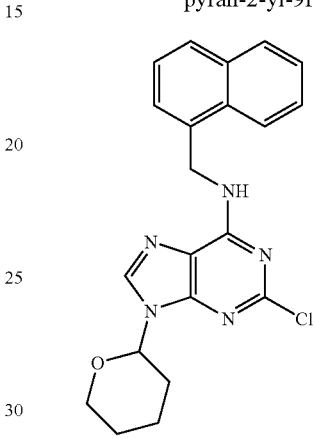

1-Naphthylmethanamine (5.4 g, 19.7 mmol) was added to a stirred solution of 2,6-dichloro-9-(tetrahydro-2H-pyran-2-yl)-9H-purine (3.5 g, 22.3 mmol) (Preparation 19) and triethylamine (4 g, 39.6 mmol) in acetonitrile (150 ml) at room temperature. The reaction mixture was stirred at room temperature for 64 hours. The solvent was removed under reduced pressure, ethyl acetate (100 ml) was added and then the solvent was removed under reduced pressure again. The residue was purified by column chromatography on silica gel eluting with pentane: ethyl acetate (1:1 by volume) increasing in polarity to neat ethyl acetate. The solvent was removed under reduced pressure to give the title compound (7.56 g) as a solid.

$\delta_H$ (400 MHz; CDCl$_3$): 8.10–8.00 (1H, m), 7.90–7.80 (3H, m), 7.55–7.45 (3H, m), 7.45–7.40 (1H, m), 6.15 (1H, s), 5.70–5.60 (1H, m), 5.25 (1H, bs), 4.20–4.10 (1H, m), 3.80–3.70 (1H, m), 2.15–2.00 (2H, m), 2.00–1.80 (1H, m), 1.80–1.60 (3H, m).

Preparation 10
6-[(1-Naphthylmethyl)amino]-9H-purine-2-carbonitrile

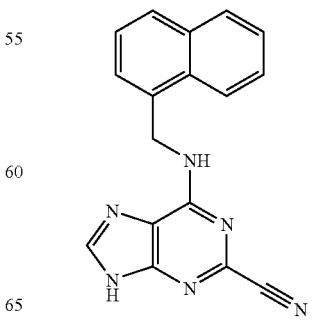

Tetrakistriphenylphosphine palladium (1.1 g, 0.95 mmol) was added to a solution of 2-chloro-N-(1-naphthylmethyl)-9-tetrahydro-2H-pyran-2-yl-9H-purin-6-amine (7.5 g, 19 mmol) (Preparation 9), zinc cyanide (1.4 g, 11.9 mmol) and N-ethyl-N-isopropyl-2-propanamine (4 ml, 23 mmol) in N'N'-dimethylformamide (80 ml). The reaction mixture was heated to 100° C. for 16 hours. The reaction mixture was allowed to cool to room temperature and ethyl acetate (250 ml) was added. The resulting mixture was extracted with aqueous sodium hydroxide solution (2M, 100 ml). The sodium hydroxide layer was extracted with more ethyl acetate (50 ml). The ethyl acetate layers were combined and washed with water (50 ml) and then dried over anhydrous magnesium sulphate. The solvent was removed under reduced pressure, the residue was dissolved in dichloromethane (100 ml) and the solvent was removed under reduced pressure again. The residue was purified by column chromatography on silica gel eluting with dichloromethane:methanol (99:2 by volume) increasing in polarity to dichloromethane:methanol (90:10 by volume). The solvent was removed under reduced pressure to give the title compound (1.8 g) as a foam. The major product of this reaction was actually 6-[(1-naphthylmethyl)amino]-9-tetrahydro-2H-pyran-2-yl-9H-purine-2-carbonitrile (2.7 g).

$\delta_H$ (400 MHz; d$_6$DMSO): 8.35–8.25 (1H, m), 8.25–8.15 (1H, m), 7.95–7.90 (1H, m), 7.90–7.80 (1H, m), 7.60–7.40 (4H, m), 5.20–5.10 (2H, m).

Preparation 11

(2S,3S,4R,5R)-5-{2-(Aminomethyl)-6-[(2,2-diphenylethyl)amino]-9H-purin-9-yl}-N-ethyl-3,4-dihydroxytetrahydro-2-furancarboxamide

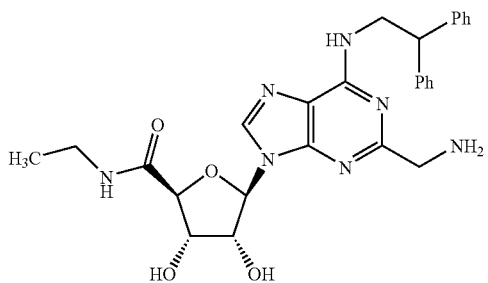

10% Palladium on carbon (400 mg) was added to a solution of (2S,3S,4R,5R)-4-(benzoyloxy)-5-{2-cyano-6-[(2,2-diphenylethyl)amino]-9H-purin-9-yl}-2-[(ethylamino)carbonyl]tetrahydro-3-furanyl benzoate (Preparation 7) (2.0 g, 2.70 mmol) in a saturated solution of ammonia in ethanol (40 ml). The reaction mixture was stirred under an atmosphere of hydrogen (414 kPa, 60 psi) for 16 hours at room temperature. The suspension was filtered through Arbocel (Trade Mark) and the solvent was removed under reduced pressure. The residue was purified by column chromatography on silica gel eluting with dichloromethane:methanol: 0.88 concentrated aqueous ammonia (95:5:0.5 by volume) increasing to (90:10:1 by volume). This gave the title compound as a solid (1.2 g).

$\delta_H$ (400 MHz; d$_6$DMSO): 8.55 (1H, s), 8.45–8.30 (1H, br s), 7.45–7.10 (10H, m), 6.10–6.00 (1H, m), 4.70–4.50 (2H, m), 4.35–4.10 (6H, m), 3.20–3.05 (2H, m), 1.10–0.95 (3H, m).

Preparation 12

(2S,3S,4R,5R)-5-(6-[(2,2-Diphenylethyl)amino]-2-{[({[2-(isopropylamino)ethyl]amino}carbonyl)amino]methyl}-9H-purin-9-yl)-N-ethyl-3,4-dihydroxytetrahydro-2-furancarboxamide

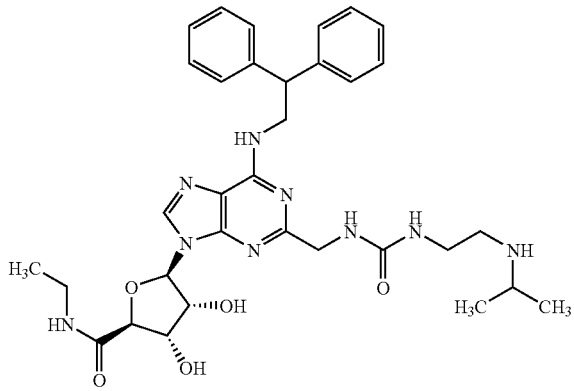

NN'-Carbonyldiimidazole (0.47 g, 2.9 mmol) was added to a stirred solution of (2S,3S,4R,5R)-5-{2-(aminomethyl)-6-[(2,2-diphenylethyl)amino]-9H-purin-9-yl}-N-ethyl-3,4-dihydroxytetrahydro-2-furancarboxamide (1.5 g, 2.9 mmol) (Preparation 11) in NN'-dimethylformamide (10 ml) at room temperature. The reaction mixture was stirred at room temperature for 4 hours. N'-Isopropylethylene diamine was then added and the reaction mixture was stirred for 16 hours at room temperature. The solvent was then removed under reduced pressure. The residue was purified by column chromatography on silica gel eluting with dichloromethane:methanol:0.88 concentrated aqueous ammonia (95:5:0.5 by volume) increasing in polarity to dichloromethane:methanol:0.88 concentrated aqueous ammonia (80:20:3 by volume). This gave the title compound as a foam (0.66 g).

m/z MH$^+$ 647. $\delta_H$ (400 MHz; CD$_3$OD): 8.20 (1H, m), 7.35–7.20 (8H, m), 7.20–7.10 (2H, m), 6.05–6.00 (1H, m), 4.55–4.40 (5H, m), 4.30–4.20 (2H, m), 3.35–3.20 (4H, m), 2.90–2.80 (1H, m), 2.70–2.65 (2H, m), 1.15–1.05 (6H, m).

Preparation 13

(2R,3R,4S,5R)-2-{2-(Aminomethyl)-6-[(9H-fluoren-9-ylmethyl)amino]-9H-purin-9-yl}-5-(hydroxymethyl)tetrahydro-3,4-furandiol

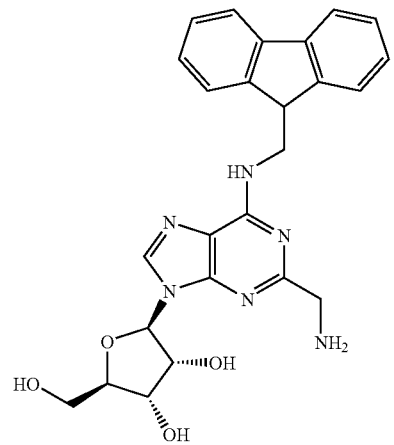

Ammonia gas was passed through an ice cold solution of (2R,3R,4R,5R)-4-(acetyloxy)-2-[(acetyloxy)methyl]-5-{2-cyano-6-[(9H-fluoren-9-ylmethyl)amino]-9H-purin-9-yl}tetrahydro-3-furanyl acetate (1.2 g, 2 mmol) (Preparation 71) in ethanol (40 ml) until the solution was saturated. 10% Palladium on carbon (120 mg) was added and the reaction mixture was stirred under an atmosphere of hydrogen gas (413.7 kPa, 60 psi) at room temperature for 40 hours. The suspension was filtered through Arbocel (Trade Mark) and the solvent was removed from the filtrate under reduced pressure. The residue was purified by column chromatography on silica gel eluting with dichloromethane:methanol: 0.88 concentrated aqueous ammonia (96:4:0.4 by volume) increasing in polarity to dichloromethane:methanol:0.88 concentrated aqueous ammonia (94:6:0.5 by volume). The solvent was removed under reduced pressure to give the title compound (358 mg) as a foam.

m/z MH$^+$ 475. $\delta_H$ (400 MHz; CD$_3$OD): 8.20 (1H, m), 7.85–7.75 (2H, m), 7.70–7.60 (2H, m), 7.40–7.20 (4H, m), 6.00–5.90 (1H, m), 4.40–4.35 (1H, m), 4.35–4.30 (1H, m), 4.20–4.00 (3H, m), 3.90–3.70 (4H, m).

Preparation 14

(2S,3S,4R,5R)-4-(Benzoyloxy)-5-(6-[(2,2-diphenyl-ethyl)amino]-2-{[({[2-(1-piperidinyl) ethyl] amino}carbonyl)amino]methyl}-9H-Purin-9-yl)-2-[(ethylamino)carbonyl]tetrahydro-3-furanyl benzoate

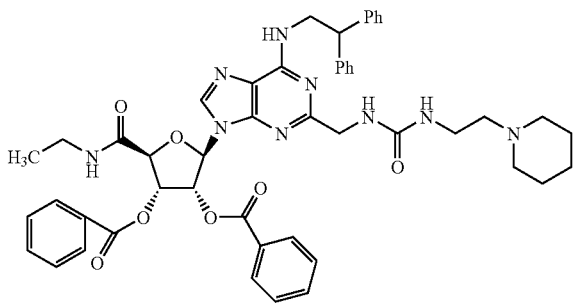

N,O-Bistrimethylsilylacetamide (0.34 ml, 1.4 mmol) was added to a stirred suspension of N-({6-[(2,2-diphenylethyl)amino]-9H-purin-2-yl}methyl)-N'-[2-(1-piperidinyl) ethyl] urea (100 mg, 0.2 mmol) (Preparation 5) in 1,1,1-trichloroethane (20 ml) at 50° C. The reaction mixture was stirred at this temperature for 30 minutes, allowed to cool to room temperature and then evaporated under reduced pressure. Toluene (5 ml) was added and the solvent was removed under reduced pressure. The residue was redissolved in toluene (20 ml). (2S,3S,4R,5R)-5-(Acetyloxy)-4-(benzoyloxy)-2-[(ethylamino)carbonyl]tetrahydro-3-furanyl benzoate and (2S,3S,4R,5S)-5-(acetyloxy)-4-(benzoyloxy)-2-[(ethylamino)carbonyl]tetrahydro-3-furanyl benzoate (Preparation 18) and then trimethylsilyltrifluoromethanesulphonate (0.1 ml, 0.35 mmol) were added and the reaction mixture was heated under reflux for 2 hours. The reaction was then allowed to cool to room temperature and diluted with ethyl acetate (100 ml). The solution was washed with saturated aqueous sodium hydrogen carbonate solution (2×50 ml) and saturated aqueous sodium chloride solution (50 ml) and then dried (anhydrous magnesium sulphate). The solvent was removed to give a residue that was purified by column chromatography on silica gel eluting with dichloromethane:methanol:0.88 concentrated aqueous ammonia (95:5:0.5 by volume). This gave an impure oil (100 mg) which was used without further purification in subsequent experiments.

Preparation 15

(3aR,4S,6R,6aR)-N-Ethyl-6-methoxy-2,2-dimethyltetrahydrofuro[3,4-d][1,3]dioxole-4-carboxamide

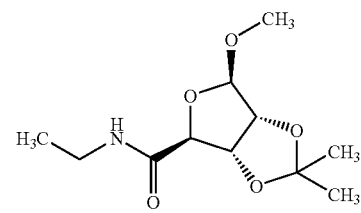

Oxalyl chloride (14.0 ml, 160 mmol) was added dropwise to a stirred solution of (3aR,4S,6R,6aR)-6-methoxy-2,2-dimethyltetrahydrofuro[3,4-d][1,3]dioxole-4-carboxy acid (J. Am. Chem. Soc., 80, 1958, 5168–5173) (23.30 g, 107 mmol) in anhydrous dichloromethane (120 ml) and N,N'-dimethylformamide (2 drops) and the mixture was stirred at room temperature for 3 hours until gas evolution had ceased. TLC analysis showed that some starting material still remained and so more N,N-dimethylformamide (2 drops) was added and stirring was continued for 1 hour. The solvent was removed under reduced pressure and the residue was azeotroped twice with anhydrous dichloromethane. The residue was then dissolved in anhydrous dichloromethane (200 ml) and the solution was treated dropwise with a solution of ethylamine in tetrahydrofuran (2M, 140 ml, 280 mmol). This solution was left to stand at room temperature for 48 hours. Diethyl ether (250 ml) was added and the mixture was stirred for 15 minutes. The mixture was filtered and the solvent was removed from the filtrate under reduced pressure. The residue was purified by column chromatography on silica gel eluting with a gradient system of dichloromethane ethyl acetate (100:0 by volume) gradually changing to dichloromethane:ethyl acetate (44: 66 by volume) to afford the title compound as a yellow solid (24.70 g).

$\delta_H$ (400 MHz; CDCl$_3$): 6.53 (1H, br m), 5.12 (1H, dd), 5.07 (1H, d), 4.60 (1H, d), 4.54 (1H, dd), 3.46 (3H, s), 3.32 (2H, m), 1.51 (3H, s), 1.34 (3H, s), 1.15 (3H, t). m/z MH$^+$ 246.

Preparation 16

(2S,3S,4R,5R)-N-Ethyl-3,4-dihydroxy-5-methoxytetrahydro-2-furancarboxamide and (2S,3S,4R,5S)-N-ethyl-3,4-dihydroxy-5-methoxytetrahydro-2-furancarboxamide

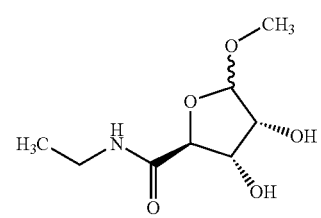

A solution of (3aR,4S,6R,6aR)-N-ethyl-6-methoxy-2,2-dimethyltetrahydrofuro[3,4-d][1,3]dioxole-4-carboxamide (Preparation 15) (24.60 g, 100 mmol) and pyridinium p-toluenesulphonate (2.50 g, 10 mmol) in methanol (500 ml) was heated under reflux for 18 hours. NMR analysis showed that some starting material still remained and therefore the solvent was removed under reduced pressure. The residue was dissolved in methanol (500 ml) and heated under reflux for 8 hours. NMR analysis showed that some starting material still remained therefore the solvent was removed under reduced pressure once more, the residue was dissolved in methanol (500 ml) and the resulting solution was heated under reflux for 24 hours. The solvent was then removed under reduced pressure and the residue was azeotroped three times with dichloromethane to afford the title compound as an oil and as a mixture of α and β anomers (20.50 g).

$\delta_H$ (400 MHz; CDCl$_3$): 6.58 (1H, br m), 4.99 (0.25H, d), 4.94 (0.75H, d), 4.46 (0.25H, d), 4.37 (1H, m), 4.24 (0.25H, dd), 4.05 (1H, m), 3.52 (0.75H, s), 3.47 (2.25H, s), 3.30 (2H, m), 1.16 (3H, m).

Preparation 17

(2S,3S,4R,5R)-4-(Benzoyloxy)-2-[(ethylamino)carbonyl]-5-methoxytetrahydro-3-furanyl benzoate and (2S,3S,4R,5S)-4-(benzoyloxy)-2-[(ethylamino)carbonyl]-5-methoxytetrahydro-3-furanyl benzoate

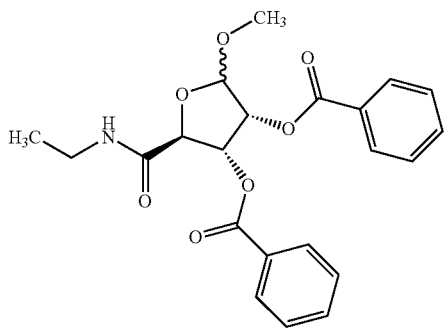

A solution of benzoyl chloride (30.0 ml, 259 mmol) in dichloromethane (100 ml) was added slowly to a solution of (2S,3S,4R,5R)-N-ethyl-3,4-dihydroxy-5-methoxytetrahydro-2-furancarboxamide and (2S,3S,4R,5S)-N-ethyl-3,4-dihydroxy-5-methoxytetrahydro-2-furancarboxamide (Preparation 16) (20.50 g, 100 mmol) and pyridine (33.0 ml, 409 mmol) in dichloromethane (400 ml) and the resulting mixture was stirred at room temperature for 18 hours. The solvent was removed under reduced pressure and the residue was partitioned between diethyl ether and aqueous hydrochloric acid (1 M, 300 ml). The layers were separated and the aqueous layer was re-extracted with diethyl ether. The organic layers were combined, washed sequentially with water and brine, dried over anhydrous magnesium sulphate, filtered and evaporated under reduced pressure. The residue was purified by column chromatography on silica gel eluting with a gradient system of dichloromethane:diethyl ether (95:5 by volume) gradually changing to dichloromethane:diethyl ether (80:20 by volume) to afford the title compound as an oil and as a mixture of α and β anomers (37.0 g).

$\delta_H$ (400 MHz; CDCl$_3$): 8.16 (0.5H, d), 7.95 (1.5H, d), 7.88 (1.5H, d), 7.81 (0.5H, d), 7.25–7.66 (6H, m), 6.65 (1H, br m), 5.88 (1H, m), 5.60 (0.75H, dd), 5.46 (0.25H, d), 5.23 (0.75H, d), 5.17 (0.25H, t), 4.80 (1H, m), 3.59 (2.25H, s), 3.49 (0.75H, s), 3.39 (2H, m), 1.23 (3H, t).

Preparation 18

(2S,3S,4R,5R)-5-(Acetyloxy)-4-(benzoyloxy)-2-[(ethylamino)carbonyl]tetrahydro-3-furanyl benzoate and (2S,3S,4R,5S)-5-(acetyloxy)-4-(benzoyloxy)-2-[(ethylamino)carbonyl]tetrahydro-3-furanyl benzoate

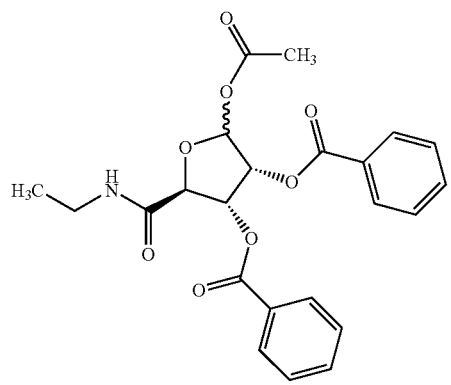

A solution of (2S,3S,4R,5R)-4-(benzoyloxy)-2-[(ethylamino)carbonyl]-5-methoxytetrahydro-3-furanyl benzoate and (2S,3S,4R,5S)-4-(benzoyloxy)-2-[(ethylamino)carbonyl]-5-methoxytetrahydro-3-furanyl benzoate (Preparation 17) (37.0 g, 89.6 mmol) in a mixture of acetic acid (330 ml, 5.77 mol) and acetic anhydride (67 ml, 709 mmol) was cooled to −10° C. and treated dropwise with hydrochloric acid (12 N, 7.0 ml, 132 mmol). The mixture was stirred for 18 hours, during which time it was allowed to warm to room temperature. After cooling the mixture to 0° C., water (1000 ml) was added slowly. The mixture was then extracted three times with ethyl acetate (3 portions of 500 ml). The organic layers were combined, washed sequentially with water, a saturated aqueous solution of sodium hydrogen carbonate and brine, dried over anhydrous magnesium sulphate, filtered and evaporated under reduced pressure. The residue was purified by column chromatography on silica gel eluting with a gradient system of diethyl ether:pentane (66:44 by volume) gradually changing to diethyl ether:pentane (100:0 by volume). The residue was further purified by column chromatography on silica gel eluting with a gradient system of dichloromethane:diethyl ether (95:5 by volume) gradually changing to dichloromethane:diethyl ether (90:10 by volume) to afford the title compound as a mixture of α- and β-anomers (15.40 g).

$\delta_H$ (400 MHz; CDCl$_3$): 8.12 (0.8H, d), 7.97 (1.2H, d), 7.92 (1.2H, d), 7.79 (0.8H, d), 7.24–7.65 (6H, m), 6.73 (0.4H, d), 6.62 (0.4H, br m), 6.46 (0.6H, br m), 6.42 (0.6H, d), 6.07 (0.4H, dd), 5.95 (0.6H, t), 5.72 (0.6H, d), 5.44 (0.4H, t), 4.94 (0.4H, d), 4.86 (0.6H, d), 3.36 (2H, m), 2.17 (1.8H, s), 2.10 (1.2H, s), 1.20 (3H, m).

Preparation 19

2,6-Dichloro-9-(tetrahydro-2H-pyran-2-yl)-9H-purine

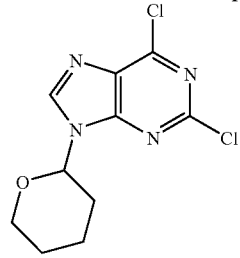

2,6-Dichloro-9H-purine (20 g, 0.11 mol) and 4-toluene-sulphonic acid monohydrate (0.2 g) were dissolved in ethyl acetate (300 ml), the mixture was heated to 50° C. and a solution of 3,4-dihydro-2H-pyran (12.6 ml, 0.14 mol) in ethyl acetate (50 ml) was added slowly over 30 minutes. The reaction mixture was cooled to room temperature, water (100 ml) was added and the pH of the solution was adjusted to 7 by addition of a saturated aqueous solution of sodium hydrogen carbonate. The organic layer was separated, washed sequentially with water and brine, dried over anhydrous magnesium sulphate, filtered and evaporated under reduced pressure. The residue was azeotroped with pentane (100 ml) to afford the title compound as a slightly impure white solid (30.9 g).

$\delta_H$ (400 MHz; CDCl$_3$): 8.30 (1H, s), 5.75 (1H, dd), 4.25–4.15 (1H, m), 3.85–3.70 (1H, m), 2.20–1.60 (6H, m).

Preparation 20

2–Chloro-N-(2,2-diphenylethyl)-9-(tetrahydro-2H-pyran-2-yl)-9H-purin-6-amine

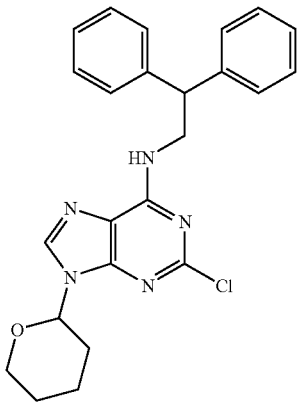

A solution of 2,6-dichloro-9-(tetrahydro-2H-pyran-2-yl)-9H-purine (Preparation 19) (30.9 g, 0.11 mol) in isopropyl alcohol (600 ml) was treated with N-ethyl-N-isopropyl-2-propanamine (47.5 ml, 0.27 mol) and 2,2-diphenylethylamine (24.8 g, 0.13 mol) and the resulting mixture was heated under reflux for 3 hours. The solvent was removed under reduced pressure and the residue was azeotroped with ethyl acetate. The residue was purified by column chromatography on silica gel eluting with a gradient system of ethyl acetate: hexane (40:60, by volume) gradually changing to ethyl acetate:hexane (60:40, by volume) to afford the title compound as a foam (49.7 g).

$\delta_H$ (400 MHz; CDCl$_3$): 7.95–7.75 (1H, br s), 7.35–7.15 (10H, m), 5.80–5.70 (1H, br s), 5.65(1H, d), 4.35(1H, m), 4.30–4.18(1H, br s), 4.10(1H, d), 3.70(1H, t), 2.05–1.95 (2H, m), 1.95–1.80 (1H, m), 1.80–1.55 (3H, m).

Preparation 21

N-(2,2-Diphenylethyl)-2-(methylsulfanyl)-9-(tetrahydro-2H-pyran-2-yl)-9H-purin-6-amine

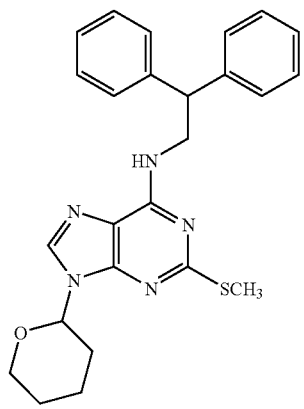

A solution of 2-chloro-N-(2,2-diphenylethyl)-9-(tetrahydro-2H-pyran-2-yl)-9H-purin-6-amine (Preparation 20) (49.7 g, 0.11 mol) in dry N,N-dimethylformamide (200 ml) was treated with sodium thiomethoxide (10 g, 0.14 mol) and the resulting mixture was heated under an atmosphere of nitrogen at 100° C. for 90 minutes. The mixture was stirred at room temperature for 72 hours and then reheated at 100° C. for a further 2 hours. The reaction mixture was cooled and diluted with water (1000 ml). A suspension was formed which was extracted twice with diethyl ether (500 ml). The combined organic layers were washed sequentially with water and brine, dried over anhydrous magnesium sulphate, filtered and evaporated under reduced pressure. The residue was azeotroped sequentially with diethyl ether and pentane to afford the title compound as a foam (48.9 g).

$\delta_H$ (400 MHz; CDCl$_3$): 7.80 (1H, s), 7.20–7.10 (10H, m), 5.70–5.55 (2H, d), 4.40–4.20 (3H, m), 4.20–4.05 (1H, m), 3.80–3.65 (1H, m), 2.60 (3H, s), 2.15–1.90 (3H, m), 1.90–1.60 (3H, m).

Preparation 22

N-(2,2-Diphenylethyl)-2-(methylsulfonyl)-9-(tetrahydro-2H-pyran-2-yl)-9H-purin-6-amine

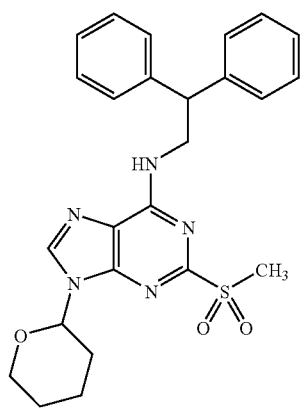

A solution of Oxone (Trade Mark) (potassium peroxymonosulphate) (44 g, 71.7 mmol) in water (200 ml) was added dropwise over 2 hours to a solution of N-(2,2-diphenylethyl)-2-(methylsulfanyl)-9-(tetrahydro-2H-pyran-2-yl)-9H-purin-6-amine (Preparation 21) (25 g, 56.2 mmol) and sodium hydrogencarbonate (20 g, 238 mmol) in a mixture of acetone (1000 ml) and water (250 ml). The resultant mixture was stirred at room temperature for 24 hours and filtered and the residue was washed with acetone. The acetone was removed from the filtrate under reduced pressure and the resulting aqueous residue was extracted with ethyl acetate and then dichloromethane. The combined organic layers were washed with brine, dried over anhydrous magnesium sulphate, filtered and evaporated under reduced pressure. The residue was triturated with diethyl ether, filtered, washed with diethyl ether and pentane and then dried to afford the title compound as a white solid (20.32 g).

$\delta_H$ (400 MHz; CDCl$_3$): 8.00 (1H, s), 7.35–7.15 (10H, m), 6.05–5.95 (1H, br s), 5.75 (1H, d), 4.40–4.35 (1H, m), 4.35–4.20 (2H, br s), 4.15–4.05 (1H, m), 3.75 (1H, t), 3.30 (3H, s), 2.18–2.05 (1H, m), 2.05–1.98 (1H, m), 1.98–1.80 (1H, m), 1.80–1.60 (3H, m).

Preparation 23

6-[(2,2-Diphenylethyl)amino]-9-(tetrahydro-2H-pyran-2-yl)-9H-purine-2-carbonitrile

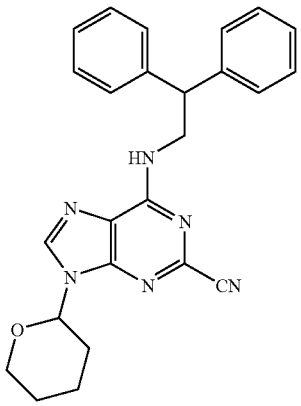

A solution of N-(2,2-diphenylethyl)-2-(methylsulfonyl)-9-(tetrahydro-2H-pyran-2-yl)-9H-purin-6-amine (Preparation 22) (20.1 g, 42.1 mmol) in dry N,N-dimethylformamide (100 ml) was treated with potassium cyanide (5.5 g, 84.6 mmol) and the mixture was heated at 120° C. for 24 hours under a nitrogen atmosphere. The mixture was cooled to room temperature and diluted with water (1000 ml) and stirring was continued for a further 1 hour. The resultant solid was filtered off and washed several times with water. The solid was then dissolved in dichloromethane and the solution was washed with water, dried over anhydrous magnesium sulphate, filtered and evaporated under reduced pressure. The residue was azeotroped with diethyl ether (twice) to afford the title compound as an oil (17 g).

$\delta_H$ (400 MHz; CDCl$_3$): 8.00 (1H, s), 7.40–7.20 (1 OH, m), 6.00–5.75 (1H, br s), 5.70 (1H, d), 4.40–4.20 (3H, m), 4.20–4.10 (1H, m), 3.80–3.70 (1H, m), 2.20–1.90 (3H, m), 1.90–1.60 (3H, m).

Preparation 24

6-[(2,2-Diphenylethyl)amino]-9H-purine-2-carbonitrile

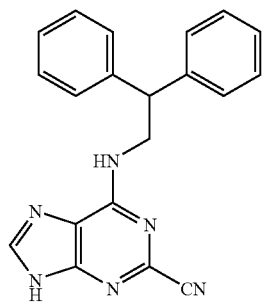

A solution of 6-[(2,2-diphenylethyl)amino]-9-(tetrahydro-2H-pyran-2-yl)-9H-purine-2-carbonitrile (Preparation 23) (17 g, 40.1 mmol) in ethanol (850 ml) was treated with 2 N aqueous hydrochloric acid (50 ml) and the mixture was stirred at room temperature for 24 hours. The solvent was removed under reduced pressure, the residue was dissolved in ethanol and the solvent was again removed under reduced pressure. The residue was triturated with diethyl ether, filtered, washed with diethyl ether and pentane and dried to afford the title compound as a solid (13.6 g).

$\delta_H$ (400 MHz; d$_6$DMSO): 8.30 (1H, s), 8.20–8.05 (1H, br s), 7.40–7.10 (10H, m), 4.60–4.40 (1.4H, m), 4.20–4.00 (1.6H, m).

m/z [MH$^+$] 341.

Preparation 25

N'-({6-[(2,2-diphenylethyl)amino]-9-tetrahydro-2H-pyran-2-yl-9H-purin-2-yl}methyl)-N-methyl-N-[2-(2-pyridinyl)ethyl]urea

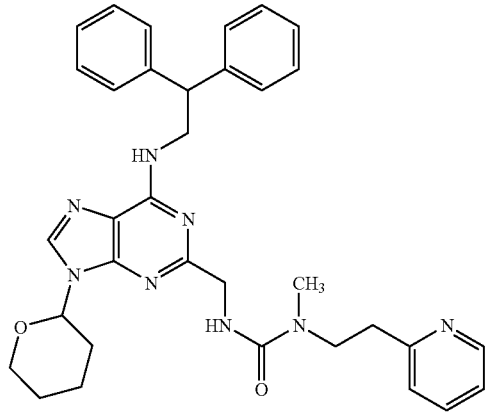

N'N'-Carbonyldiimidazole (0.42 g, 2.6 mmol) was added to a solution of 2-(aminomethyl)-N-(2,2-diphenylethyl)-9-tetrahydro-2H-pyran-2-yl-9H-purin-6-amine (1.0 g, 2.3 mmol) (Preparation 3) in dichloromethane (100 ml). The reaction mixture was stirred for 16 hours at room temperature. Dichloromethane (100 ml) was added and the solution was washed with water (50 ml) and saturated aqueous sodium chloride solution (50 ml). The organic layer was dried over anhydrous magnesium sulphate and the solvent was removed under reduced pressure. A portion of this residue (200 mg) was dissolved in tetrahydrofuran (50 ml) and N-methyl-2-(2-pyridinyl)ethanamine (200 mg, 1.5 mmol) and triethylamine (0.14 ml, 1.0 mmol) were added. The reaction mixture was heated under reflux for 2.5 hours. The reaction mixture was allowed to cool to room temperature and the solvent was removed under reduced pressure. The residue was redissolved in ethylacetate (100 ml) and Washed with water (100 ml) and saturated aqueous sodium chloride solution (100 ml). The organic phase was dried over anhydrous magnesium sulphate and the solvent was removed under reduced pressure. The residue was purified by column chromatography on silica gel eluting with dichloromethane:methanol:0.88 concentrated aqueous ammonia (97:3:0.5 by volume). The solvent was removed under reduced pressure to give the title compound as a foam (100 mg).

$\delta_H$ (400 MHz; CDCl$_3$): 8.50–8.40 (1H, m), 7.85–7.75 (1H, m), 7.60–7.50 (1H, m), 7.30–7.10 (11H, m), 7.10–7.00 (1H, m), 6.20–6.10 (1H, m), 6.10–6.00 (1H, m), 5.70–5.60 (1H, m), 4.55–4.45 (2H, m), 4.35–4.15 (3H, m), 4.15–4.05 (1H, m), 3.75–3.60 (3H, m), 3.05–2.95 (2H, m), 2.75 (3H, s), 2.10–1.90 (3H, m), 1.80–1.50 (3H, m).

Preparation 26

N'-({6-[(2,2-Diphenylethyl)amino]-9H-purin-2-yl}methyl)-N-methyl-N-[2-(2-pyridinyl)ethyl]urea

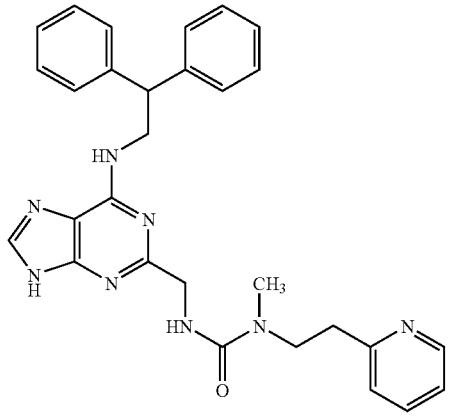

Aqueous hydrochloric acid (2M, 5 ml) was added to a solution of N'-({6-[(2,2-diphenylethyl)amino]-9-tetrahydro-2H-pyran-2-yl-9H-purin-2-yl}methyl)-N-methyl-N-[2-(2-pyridinyl)ethyl]urea (Preparation 25) in methanol (50 ml). The solution was stirred for 16 hours at room temperature. The solvent was removed under reduced pressure. The residue was dissolved in ethyl acetate (100 ml) and the solution was washed with saturated aqueous sodium hydrogen carbonate solution (50 ml) and then dried over anhydrous magnesium sulphate. The solvent was removed under reduced pressure to give the title compound (0.161 g) as a gum.

$\delta_H$ (400 MHz; CD$_3$OD): 8.45–8.40 (1H, m), 7.90 (1H, m), 7.70–7.65 (1H, m), 7.30–7.20 (10H, m), 7.15–7.10 (2H, m), 4.45–4.35 (3H, m), 4.30–4.20 (2H, m), 3.55–3.45 (2H, m), 2.95–2.90 (2H, m), 2.75 (3H, m).

Preparation 27

N-[2-(Diisopropylamino)ethyl]-1H-imidazole-1-carboxamide

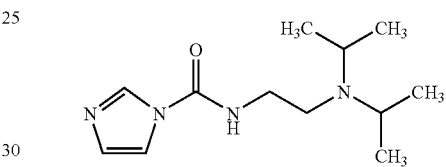

$N^1,N^1$-Diisopropyl-1,2-ethanediamine (1 g, 6.94 mmol) was added to a stirred solution of N,N'-carbonyldiimidazole (1.12 g, 6.94 mmol) in dichloromethane (50 ml) at room temperature. The reaction mixture was stirred for 1 hour and then diluted with more dichloromethane (50 ml), washed with water (60 ml), dried with anhydrous magnesium sulphate and evaporated under reduced pressure. This gave the title compound as a solid (600 mg).

$\delta_H$ (400 MHz; CDCl$_3$): 8.05 (1H, s), 7.25 (1H, s), 7.05 (1H, s), 6.65 (1H, br s), 3.40–3.35 (2H, m), 3.10–3.00 (2H, m), 2.75–2.70 (2H, m), 1.05–1.00 (6H, m).

Preparations 28–37

The following compounds were prepared by the method of Preparation 27 using the appropriate amine.

| Preparation Number | Structure (starting materials) | $^1$H-NMR (400 MHz) |
|---|---|---|
| 28 | 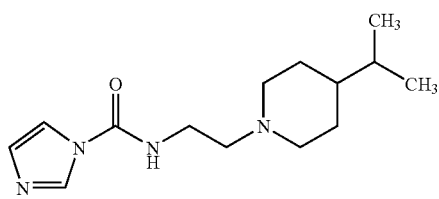<br>(Preparation 57) | $\delta_H$ (400MHz; CDCl$_3$): 8.10 (1H, s), 7.35 (1H, s), 7.10 (1H, s), 6.80 (1H, br s), 3.45 (2H, m), 2.55 (2H, m), 2.50–2.30 (4H, m), 1.60–1.40 (6H, m). |

| Preparation Number | Structure (starting materials) | ¹H-NMR (400 MHz) |
|---|---|---|
| 29 | (Preparation 42) | δ$_H$ (400MHz; CDCl$_3$): 8.10 (1H, s), 7.35 (1H, s), 7.10 (1H, s), 6.80 (1H, br s), 3.45 (2H, m), 2.55 (2H, m), 2.50–2.30 (4H, m), 1.60–1.40 (6H, m). |
| 30 | (Preparation 44) | δ$_H$ (400MHz; CDCl$_3$): 8.05 (1H, s), 7.50–7.45 (2H, m), 7.40 (1H, s), 7.30–7.20 (3H, m), 7.15–7.10 (1H, m), 6.95 (1H, s), 3.30–3.25 (2H, m), 2.90–2.85 (1H, m), 2.80–2.75 (2H, m), 1.35 (6H, m), 0.95–0.90 (6H, m). |
| 31 | (See EP-21973) | δ$_H$ (400MHz; CDCl$_3$): 8.15 (1H, m), 8.05 (1H, s), 7.45 (1H, m), 7.20 (1H, s), 7.00 (1H, s), 6.65 (1H, m), 6.55 (1H, m), 5.90 (1H, d), 4.25 (2H, d), 4.05 (1H, m), 2.95 (2H, t), 2.10 (2H, d), 1.55 (2H, t). |
| 32 | (Preparation 58) | δ$_H$ (400MHz; CDCl$_3$): 8.05 (1H, s), 7.50–7.45 (2H, m), 7.40 (1H, s), 7.30–7.20 (3H, m), 7.15–7.10 (1H, m), 6.95 (1H, s), 3.30–3.25 (2H, m), 2.90–2.85 (1H, m), 2.80–2.75 (2H, m), 1.35 (6H, s), 0.95–0.90 (6H, m). |
| 33 |  | δ$_H$ (400MHz; CDCl$_3$): 8.05 (1H, s), 7.25 (1H, s), 7.05 (1H, s), 6.75 (1H, br s), 3.40 (2H, m), 2.60 (2H, m), 2.50–2.30 (4H, m), 1.40–1.20 (8H, m), 0.85 (6H, t). |
| 34 |  | δ$_H$ (400MHz; CDCl$_3$): 7.85 (1H, s), 7.30–7.15 (5H, m), 7.10 (1H, s), 7.05 (1H, s), 6.00 (1H, br s), 3.50 (2H, s), 3.25 (2H, m), 3.00 (1H, m), 2.65 (2H, m), 1.10 (6H, d). |

-continued

| Preparation Number | Structure (starting materials) | $^1$H-NMR (400 MHz) |
|---|---|---|
| 35 | 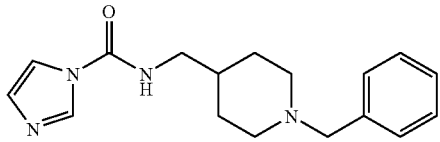<br>(See J. Med. Chem., 1999, 42(4), 730) | $\delta_H$ (400MHz; CDCl$_3$): 8.10 (1H, s), 7.30–7.20 (6H, m), 7.10 (1H, s), 5.90 (1H, m), 3.50 (2H, s), 3.35 (2H, m), 2.90 (2H, m), 2.00 (2H, m), 1.75–1.60 (3H, m), 1.40–1.30 (2H, m). |
| 36 | 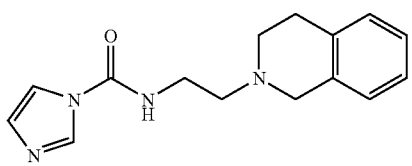<br>(See J. Med. Chem., 1996, 39(5), 1125) | $\delta_H$ (400MHz; CDCl$_3$): 8.05 (1H, s), 7.25 (1H, s), 7.15–6.95 (5H, m), 6.65 (1H, br s), 3.70 (2H, s), 3.60 (2H, m), 2.90 (2H, m), 2.75 (4H, m). |
| 37 | 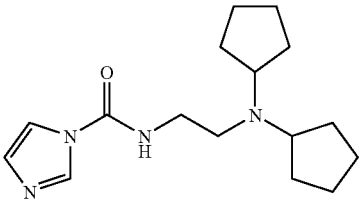<br>(Preparation 51) | $\delta_H$ (400MHz; CDCl$_3$): 8.25 (1H, s), 7.55 (1H, s), 7.00 (1H, s), 3.45–3.35 (2H, m), 3.20–3.10 (2H, m), 2.70–2.65 (2H, m), 1.80–1.65 (4H, m), 1.65–1.30 (12H, m). |

Preparation 38

N-Isopropylcyclopentanamine

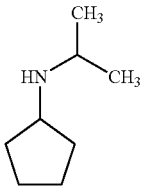

Pearlman's catalyst (20% w/w palladium hydroxide-on-carbon) (1.5 g) was added to a solution of cyclopentylamine (15 ml, 0.21 mol) in acetone (200 ml). The reaction mixture was stirred under an atmosphere of hydrogen gas at 414 kPa (60 psi). After stirring for 16 hours the reaction mixture was filtered through Arbocel (Trade Mark) and the solvent was removed under reduced pressure to give the title compound (15 ml) as a thin oil.

$\delta_H$ (400 MHz; CDCl$_3$): 3.20–3.10 (1H, m), 2.90–2.80 (1H, m), 1.95–1.85 (2H, m), 1.75–1.45 (4H, m), 1.35–1.20 (2H, m), 1.10–1.00 (6H, m).

Preparation 39

[Cyclopentyl(isopropyl)amino]acetonitrile

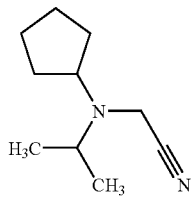

Hydroxyacetonitrile (8.2 ml of a 70% w/w solution in water, 0.1 mol) was added to a solution of N-isopropylcyclopentanamine (11.43 g, 0.09 mol) (Preparation 38) in ethanol (60 ml). The reaction mixture was heated under reflux for 3 hours, allowed to cool and evaporated under reduced pressure. The residue was purified by chromatography on silica gel eluting with dichloromethane:methanol (98:2 by volume) to give the title compound (14.1 g) as a clear oil.

$\delta_H$ (400 MHz; CDCl$_3$): 3.60–3.50 (2H, s), 3.30–3.20 (2H, m), 2.00–1.85 (2H, m), 1.80–1.55 (4H, m), 1.45–1.30 (2H, m), 1.15–1.05 (6H, m).

Preparation 40

[Isopropyl(1-methyl-1-phenylethyl)amino]acetonitrile

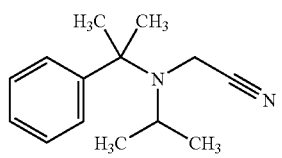

The title compound was prepared from N-isopropyl-2-phenyl-2-propanamine (Preparation 55) using a similar method to Preparation 39.

$\delta_H$ (400 MHz; CDCl$_3$): 7.55–7.45 (2H, m), 7.35–7.30 (2H, m), 7.25–7.20 (1H, m), 3.60 (2H, m), 3.10–3.00 (1H, m), 1.60 (6H, m), 1.10–1.05 (6H, m).

m/z MH$^+$ 217.

Preparation 41

(2,2,6,6-Tetramethyl-1-piperidinyl)acetonitrile

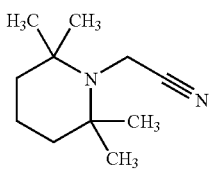

The title compound was prepared from 2,2,6,6-tetramethylpiperidine using a similar method to that of Preparation 39.

$\delta_H$ (400 MHz; CDCl$_3$): 3.45 (2H, s), 1.55–1.50 (4H, m), 1.10 (12H, m).

Preparation 42

N$^1$-Cyclopentyl-N$^1$-isopropyl-1,2-ethanediamine

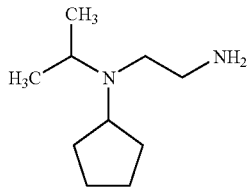

Lithium aluminium hydride (66 ml of a 1 molar solution in tetrahydrofuran, 0.066 mol) was added to a stirred solution of [cyclopentyl(isopropyl)amino]acetonitrile (10 g, 0.66 mol) (Preparation 39) in tetrahydrofuran (100 ml) at 0° C. The reaction mixture was stirred at 0° C. for 20 minutes and then heated under reflux for 2 hours. The reaction mixture was allowed to cool to room temperature and left to stand overnight. The reaction mixture was cooled in an icebath and treated dropwise with 4.8 ml of a 7.5% w/w aqueous sodium hydroxide solution followed by 7.4 ml of water. The solvent was removed under reduced pressure and the residue was slurried with diethyl ether (200 ml) for 30 minutes and then filtered. The filtrate was evaporated under reduced pressure to give the title compound as a colourless oil (10.30 g).

$\delta_H$ (400 MHz; CDCl$_3$): 3.10–2.95 (2H, m), 2.70–2.60 (2H, m), 2.50–2.40 (2H, m), 1.80–1.45 (10H, m), 1.05–0.95 (6H, m).

m/z MH$^+$ 171.

Preparation 43

2-(2,2,6,6-Tetramethyl-1-piperidinyl)ethanamine

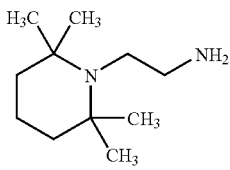

The title compound was prepared by a similar method to that of Preparation 42 using (2,2,6,6-tetramethyl-1-piperidinyl)acetonitrile (Preparation 41).

$\delta_H$ (400 MHz; CDCl$_3$): 2.70–2.60 (2H, m), 2.50–2.40 (2H, m), 1.60–1.40 (4H, m), 1.40–1.30 (4H, m), 1.00 (12H, s).

Preparation 44

N$^1$-Isopropl-N$^1$-(1-methyl-1-phenylethyl)-1,2-ethanediamine

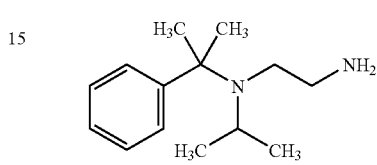

The title compound was prepared by a similar method to that of Preparation 42 using [isopropyl(1-methyl-1-phenylethyl)amino]acetonitrile (Preparation 40).

$\delta_H$ (400 MHz; CDCl$_3$): 7.55–7.50 (2H, m), 7.30–7.25 (2H, m), 7.20–7.15 (1H, m), 2.90–2.80 (1H, m), 2.70–2.60 (4H, m), 1.35 (6H, m), 0.95–0.90 (6H, m).

Preparation 45

(2R,3R,4R,5R)-4-(Acetyloxy)-2-[(acetyloxy)methyl]-5-(6-chloro-2-cyano-9H-purin-9-yl)tetrahydro-3-furanyl acetate

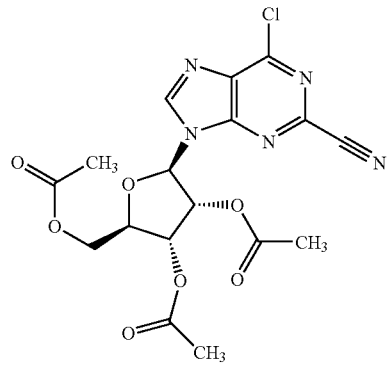

Copper(I) cyanide was added to a solution of (2R,3R,4R,5R)-4-(acetyloxy)-2-[(acetyloxy)methyl]-5-(2,6-dichloro-9H-purin-9-yl)tetrahydro-3-furanyl acetate (*J. Med. Chem.*, 248, 35, 1992) (22 g, 40 mmol) in N'N'-dimethylformamide (150 ml). The suspension was heated to 100° C. for 2 hours and was then allowed to cool to room temperature. The reaction mixture was poured into water (700 ml) with stirring. The solid was filtered off and stirred in dichloromethane (700 ml) for 30 minutes. The solid was filtered off again and then stirred in dichloromethane (700 ml) for another 30 minutes. The dichloromethane portions were combined and evaporated under reduced pressure to a volume of 500 ml. The dichloromethane was then dried over anhydrous sodium sulphate. The solvent was removed under reduced pressure. The residue was redissolved in dichloromethane (300 ml). The solvent was removed under reduced pressure. The residue was then stirred in diethylether (300 ml) for 20 minutes. The solid was filtered off and dried to give the title compound (14.8 g).

δ$_H$ (300 MHz; CDCl$_3$): 8.50 (1H, s), 6.10–6.05 (1H, m), 5.80–5.75 (1H, m), 5.55–5.50 (1H, m), 4.55–4.50 (1H, m), 4.50–4.40 (2H, m), 2.20–2.15 (6H, m), 2.10 (3H, s).

Preparation 46

(2R,3R,4S,5S)-2-(2-Amino-6-chloro-9H-purin-9-yl)-4-(benzoyloxy)-5-[(ethylamino)carbonyl]-tetrahydro-3-furanyl benzoate

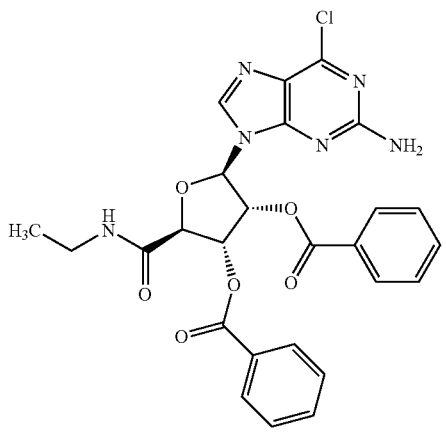

A suspension of 2-amino-6-chloropurine (4.60 g, 27.13 mmol) in 1,1,1-trichloroethane (230 ml) was treated with N,O-bis(trimethylsilyl)acetamide (20 ml, 81.4 mmol). The mixture was heated under reflux for 6 hours. The solution was allowed to cool to room temperature and the solvent was removed under reduced pressure. The residue was treated with a solution of (2S,3S,4R,5R)-5-(acetyloxy)-4-(benzoyloxy)-2-[(ethylamino)carbonyl]tetrahydro-3-furanyl benzoate and (2S,3S,4R,5S)-5-(acetyloxy)-4-(benzoyloxy)-2-[(ethylamino)carbonyl]tetrahydro-3-furanyl benzoate (Preparation 18) (14.39 g, 32.6 mmol) in anhydrous toluene (230 ml) and trimethylsilyl trifluoromethanesulfonate (20 ml, 108.5 mmol). The resulting solution was then heated at 90° C. under a nitrogen atmosphere for 90 minutes. The mixture was cooled to room temperature, diluted with ethyl acetate (250 ml) and washed with a saturated aqueous solution of sodium hydrogen carbonate (350 ml) and then brine (350 ml). The organic layer was separated, dried over anhydrous magnesium sulphate, filtered and evaporated under reduced pressure. The residue was purified by column chromatography on silica gel eluting with dichloromethane:methanol (98:2 by volume) to afford the title compound as a foam (8.1 g).

m/z MH$^+$ 552. δ$_H$ ($^{400}$ MHz; CDCl$_3$): 8.10–7.95 (3H, m), 7.80 (2H, m), 7.50–7.30 (6H, m), 6.90 (1H, m), 6.40–6.20 (3H, m), 5.20 (2H, br s), 4.90 (1H, m), 3.45 (1H, m), 3.30 (1H, m), 1.15 (3H, t).

Preparation 47

(2R,3R,4S,5S)-4-(Benzoyloxy)-2-(6-chloro-2-iodo-9H-purin-9-yl)-5-[(ethylamino)carbonyl]-tetrahydro-3-furanyl benzoate

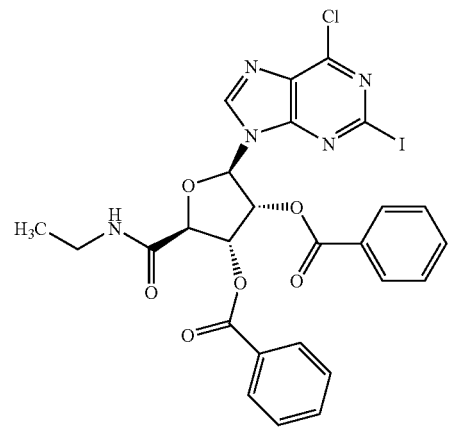

n-Butyl nitrite (4.65 ml, 39.7 mmol) was added to a suspension of (2R,3R,4S,5S)-2-(2-amino-6-chloro-9H-purin-9-yl)-4-(benzoyloxy)-5-[(ethylamino)carbonyl]-tetrahydro-3-furanyl benzoate (Preparation 46) (8.10 g, 14.7 mmol), iodine (3.73 g, 14.7 mmol), copper(I) iodide (6.16 g, 32.3 mmol) and diiodomethane (12.55 ml, 155.8 mmol) in THF (100 ml) and the mixture was heated under reflux for 2.5 hours. The solution was allowed to cool to room temperature and the solvent was removed under reduced pressure. The residue was partitioned between 5% w/w aqueous sodium metabisulfite solution (100 ml) and dichloromethane (100 ml). The organic layer was separated, filtered through Arbocel (Trade Mark), dried over anhydrous magnesium sulphate and evaporated under reduced pressure. The residue was purified by column chromatography on silica gel eluting with dichloromethane:methanol (99:1 by volume) to afford the title compound as a yellow foam (7.55 g).

m/z MNa$^+$ 684. δ$_H$ 400 MHz; CDCl$_3$): 8.55 (1H, s), 8.05 (2H, m), 7.80 (2H, m), 7.65–7.30 (6H, m), 6.75 (1H, m), 6.50 (1H, m), 6.10–6.00 (2H, m), 4.90 (1H, m), 3.60–3.40 (2H, m), 1.25 (3H, t).

Preparation 48

N-{2-[(1-Ethylpropyl)(isobutyl)amino]ethyl}-1H-imidazole-1-carboxamide

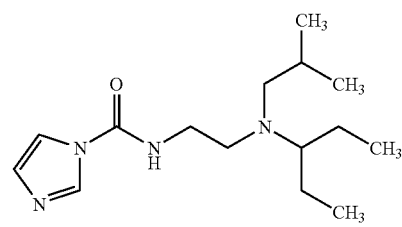

A suspension of Pearlman's catalyst (200 mg) and benzyl 2-[(1-ethylpropyl)(isobutyl)amino]ethylcarbamate (1.3 g, 4.06 mmol) (Preparation 49) in ethyl acetate (20 ml) was stirred under an atmosphere of hydrogen gas (414 kPa, 60 psi) at room temperature for 12 hours. The reaction mixture was filtered through Arbocel (Trade Mark) and then the solvent was removed under reduced pressure. The crude material was dissolved in dichloromethane (10 ml) and the resulting solution was added to a solution of N'N'-carbonyldiimidazole (0.66 g, 4.10 mmol) in dichloromethane (10 ml). The reaction mixture was stirred at room temperature for 30 minutes and then diluted with dichloromethane (50 ml). The solution was washed with water (30 ml) and dried over anhydrous magnesium sulphate. The solvent was removed under reduced pressure and the residue was purified by column chromatography on silica gel eluting with ethyl acetate increasing in polarity to ethyl acetate:methanol (97:3 by volume). This gave the title compound as a gum (0.5 g).

$\delta_H$ (400 MHz; CDCl$_3$): 8.05 (1H, s). 7.25 (1H, s), 7.10 (1H, s), 6.45 (1H, bs), 3.45–3.40 (2H, m), 2.70–2.65 (2H, m), 2.45–2.40 (2H, m), 2.30–2.20 (1H, m), 1.60–1.50 (1H, m), 1.50–1.20 (4H, m), 0.95–0.85 (12H, m).

Preparation 49

Benzyl 2-[(1-ethylpropyl)(isobutyl)amino]ethylcarbamate

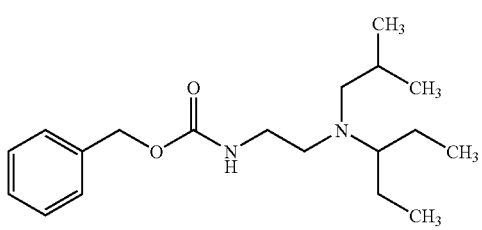

Sodium triacetoxyborohydride (1.87 g, 8.84 mmol) was added to a solution of benzyl 2-[(1-ethylpropyl)amino]ethylcarbamate (1.8 g, 6.8 mmol) (Preparation 50), 3-methylbutanal (0.8 ml, 7.5 mmol) and acetic acid (1 ml, 8.85 mmol) in dichloromethane (50 ml). The reaction mixture was stirred for 16 hours at room temperature. The reaction mixture was diluted with dichloromethane (50 ml) and then washed with saturated aqueous sodium hydrogen carbonate solution (100 ml). The organic phase was dried over anhydrous magnesium sulphate and then the solvent was removed under reduced pressure. The residue was purified by column chromatography on silica gel eluting with dichloromethane methanol (95:5 by volume) increasing in polarity to dichloromethane:methanol:0.88 concentrated aqueous ammonia (95:5:0.5 by volume). This gave the title compound as an oil (1.3 g).

$\delta_H$ (400 MHz; CDCl$_3$): 7.40–7.25 (5H, m), 5.30–5.20 (1H, m), 5.10–5.05 (2H, m), 3.25–3.15 (2H, m), 2.60–2.50 (2H, m), 2.45–2.35 (2H, m), 2.25–2.15 (1H, m), 1.65–1.50 (1H, m), 1.50–1.20 (5H, m), 1.00–0.80 (12H, m).

Preparation 50

Benzyl 2-[(1-ethylpropyl)amino]ethylcarbamate

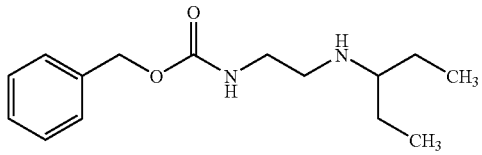

Benzyl 2-aminoethylcarbamate hydrochloride (2 g, 8.65 mmol) was dissolved in dichloromethane (50 ml) and 3-pentanone (3.7 ml, 35 mmol) was added. The reaction mixture was stirred for 1 hour at room temperature. Sodium triacetoxy borohydride (5.5 g, 26 mmol) was added and the reaction mixture was then stirred for 16 hours at room temperature. The solution was washed with saturated aqueous sodium hydrogen carbonate solution (40 ml). The dichloromethane phase was dried over anhydrous magnesium sulphate and the solvent was removed. The residues was purified by column chromatography on silica gel eluting with dichloromethane methanol:0.88 concentrated aqueous ammonia (95:5:0.5 by volume). This gave the title compound as an oil (1.8 g).

$\delta_H$ (300 MHz; CDCl$_3$): 7.20–7.10 (5H, m), 5.30 (1H, bs), 5.10 (2H, s), 3.35–3.20 (2H, m), 2.85–2.70 (2H, m), 2.40–2.30 (1H, m), 1.50–1.30 (4H, m), 0.90–0.80 (6H, m).

Preparation 51

N$^1$,N$^1$-Dicyclopentyl-1,2-ethanediamine hydrochloride

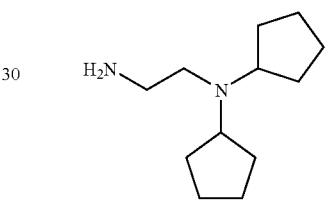

Hydrogen chloride gas was passed through a stirred ice cold solution of tert-butyl 2-(dicyclopentylamino)ethylcarbamate (0.22 g, 0.74 mmol) (Preparation 52) in dichloromethane (15 ml) until the solution was saturated. The reaction mixture was allowed to warm to room temperature and then stirred for 1 hour. The solvent was removed under reduced pressure to give the title compound (0.15 g) as a brown foam.

m/z MH$^+$ 197. $\delta_H$ (400 MHz; CDCl$_3$): 10.80 (1H, s), 8.75 (3H, s), 3.80–3.60 (6H, m), 2.25–1.50 (16H, m).

Preparation 52 tert-Butyl 2-(dicyclopentylamino)ethylcarbamate

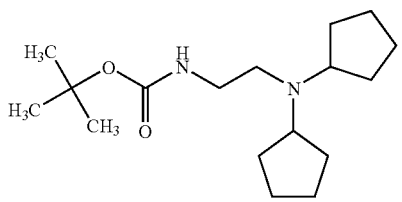

Iodocyclopentane (1.68 g, 8.6 mmol) was added to a suspension of potassium carbonate (1.8 g, 13.2 mmol) and tert-butyl 2-[cyclopentylamino]ethylcarbamate (1.5 g, 6.6 mmol) (Preparation 53) in N',N'-dimethylformamide (10 ml). The reaction mixture was stirred at 60° C. for 72 hours. The reaction mixture was allowed to cool and was then partitioned between ethyl acetate (50 ml) and water (50 ml). The ethyl acetate layer was washed with brine (30 ml) and dried over anhydrous magnesium sulphate. The solvent was removed to give a residue that was purified by chromatography on silica gel eluting with dichloromethane:methanol (98:2 by volume) increasing in polarity to dichloromethane:methanol:0.88 concentrated aqueous ammonia (90:10:1 by volume) to give the title compound (64 mg) as a brown oil.

m/z MH+ 297. $\delta_H$ (400 MHz; CDCl$_3$): 5.10–4.90 (1H, m), 3.30–3.05 (4H, m), 2.65–2.50 (2H, m), 1.85–1.30 (25H, m).

Preparation 53 tert-Butyl 2-[cyclopentylamino]ethylcarbamate

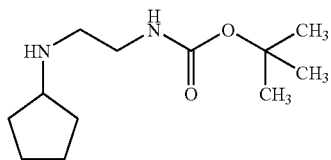

tert-Butyl 2-aminoethylcarbamate (3.0 g, 18.8 mmol) (Preparation 54) was dissolved in cyclopentanone (30 ml). Pearlman's Catalyst (0.1 g) was added and the reaction mixture was stirred under an atmosphere of hydrogen gas (414 kPa, 100 psi) for 48 hours. The catalyst was filtered off through Arbocel (Trade Mark) and the solvent was removed under reduced pressure. The residue was purified by column chromatography on silica gel eluting with dichloromethane:methanol:0.88 concentrated aqueous ammonia (95:5:0.5 by volume) increasing in polarity to dichloromethane:methanol:0.88 concentrated aqueous ammonia (90:10:1 by volume). The solvent was removed under reduced pressure to give the title compound (1.5 g) as an oil.

m/z MH+ 229. $\delta_H$ (400 MHz; CDCl$_3$): 4.90 (1H, s), 3.25–3.10 (2H, m), 3.05–2.95 (1H, m), 2.70–2.60 (2H, m), 1.85–1.75 (2H, m), 1.70–1.20 (17H, m).

Preparation 54 tert-Butyl 2-aminoethylcarbamate

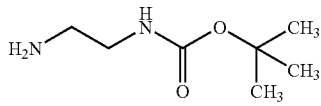

A solution of di(tert-butyl)dicarbonate (27.3 g, 0.125 mol) in dichloromethane (100 ml) was added dropwise to a solution of ethylenediamine (30 g, 0.5 mol) over an hour. The reaction mixture was stirred for a further hour at room temperature. The solvent was then removed under reduced pressure and the residue was partitioned between ethyl acetate (600 ml) and 5% w/w aqueous sodium hydroxide solution (200 ml). The ethyl acetate layer was washed with water (100 ml) and brine (100 ml) and dried over anhydrous sodium sulphate. The solvent was removed under reduced pressure to give the title compound as a white solid (19.1 g).

$\delta_H$ (60 MHz; CDCl$_3$): 3.30–2.60 (4H, m), 1.45–1.30 (9H, m), 1.20–1.05 (2H, m).

Preparation 55

N-Isopropyl-2-phenyl-2-propanamine

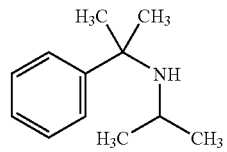

Sodium triacetoxyborohydride (4.5 g, 21.2 mmol) was added portionwise to a solution of 1-methyl-1-phenylethylamine (0.96 g, 7.1 mmol) in a mixture of acetone (5 ml) and dichloromethane (120 ml). The reaction mixture was stirred at room temperature for 16 hours. The solvent was removed under reduced pressure and the residue was partitioned between aqueous sodium hydroxide solution (2M, 100 ml) and ethyl acetate (200 ml). The ethyl acetate layer was washed with water (100 ml) and brine (100 ml) and then dried over anhydrous magnesium sulphate. The solvent was removed under reduced pressure to give the title compound (1 g) as a colourless oil.

$\delta_H$ (400 MHz; CDCl$_3$): 7.40–7.35 (2H, m), 7.30–7.20 (2H, m), 7.15–7.10 (1H, m), 3.40 (1H, bs), 2.60–2.50 (1H, m), 1.40 (6H, s), 0.90–0.85 (6H, m).

Preparation 56

2-[2-(4-Isopropyl-1-piperidinyl)ethyl]-1H-isoindole-1 3(2H)-dione

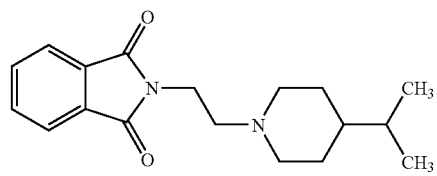

A solution of 4-isopropylpiperidine (3.3 g, 20.2 mmol), N-(2-bromoethyl)phthalimide (5.4 g, 21.3 mmol), potassium carbonate (5.9 g, 45.4 mmol) and acetonitrile (100 ml) and was heated under reflux for 2.5 hours and then stirred at room temperature overnight. The solvent was removed under reduced pressure and the residue was partitioned between ethyl acetate (100 ml) and water (100 ml). The organic layer was separated and the aqueous layer was extracted with further ethyl acetate (100 ml). The combined organic extracts were dried over anhydrous sodium sulphate and the solvent was removed by evaporation under reduced pressure. The resulting oil was purified by column chromatography on silica gel eluting with a gradient system of dichloromethane changing to dichloromethane:diethyl ether (50:50, by volume) changing to diethyl ether to afford the title compound (3.3 g).

m/z MH+ 301. $\delta_H$ (400 MHz, CDCl$_3$): 7.80 (2H, m), 7.70 (2H, m), 3.80 (2H, t), 3.00 (2H, m), 2.60 (2H, t), 1.95 (2H, m), 1.60 (2H, m), 1.40 (1H, m), 1.20 (2H, qd), 0.95 (1H, m), 0.80 (6H, d).

Preparation 57

2-(4-Isopropyl-1-piperidinyl)ethylamine

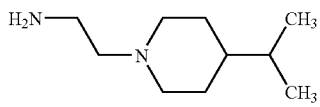

A solution of 2-[2-(4-isopropyl-1-piperidinyl)ethyl]-1H-isoindole-1,3(2H)-dione (Preparation 56) (3.2 g, 10.6 mmol) in a 33 % w/w solution of methylamine in ethanol (60 ml) was heated under reflux for three hours. The solvent was removed under reduced pressure, more ethanol was added (60 ml) and the solvent was again removed under reduced pressure. The residue was suspended in dichloromethane (100 ml) and the solid was filtered off. This was washed with dichloromethane (100 ml). The filtrate was evaporated under reduced pressure and the resulting oil was purified by column chromatography on silica gel eluting with dichloromethane:methanol:0.88 aqueous ammonia solution (90:10:1, by volume) to give a colourless oil. Bulb-to-bulb distillation (150–160° C., 4 kPa) yielded the title compound (1.0 g, 55 %).

m/z MH$^+$ 171. $\delta_H$ (400 MHz; CDCl$_3$): 2.90 (2H, m), 2.80 (2H, t), 2.40 (2H, t), 1.95 (2H, m), 1.65 (2H, m), 1.40 (1H, m), 1.30–1.20 (4H, m), 1.00 (1H, m), 0.85 (6H, d).

Preparation 58

N$^1$-(tert-Butyl)-N$^1$-cyclohexyl-1,2-ethanediamine

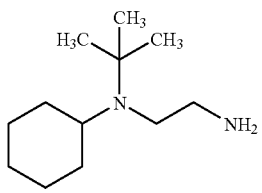

Hydroxyacetonitrile (5.3 ml of of a 70% w/w solution in water, 32 mmol) was added to a stirred solution of N-(tert-butyl)cyclohexanamine (5.3 ml, 32 mmol) in ethanol (50 ml) at room temperature. The reaction mixture was heated under reflux for 16 hours. The solution was allowed to cool to room temperature and the solvent was removed under reduced pressure. The residue was partitioned between dichloromethane (50 ml) and water (50 ml). The organic layer was dried over anhydrous magnesium sulphate and the solvent was removed under reduced pressure. The crude residue was dissolved in tetrahydrofuran (30 ml) and a solution of lithium aluminium hydride in tetrahydrofuran (1M, 55 ml, 55 mmol) was slowly added. The reaction mixture was heated under reflux for 2 hours. An aqueous solution of sodium hydroxide (2M, 6 ml) was then carefully added. The suspension was filtered and the liquid was concentrated under reduced pressure to give the title compound (3 g) as an oil.

$\delta_H$ (300 MHz; CDCl$_3$): 2.90–2.70 (1H, m), 2.70–2.55 (2H, m), 2.20–1.95 (2H, m), 1.85–1.55 (4H, m), 1.40–1.15 (4H, m), 1.15–0.95 (11H, m).

Preparation 59

(2R,3R,4R,5R)-4-(Acetyloxy)-2-[(acetyloxy)methyl]-5-(6-{[2,2-bis(4-methylphenyl)ethyl]amino}-2-cyano-9H-purin-9-yl)tetrahydro-3-furanyl acetate

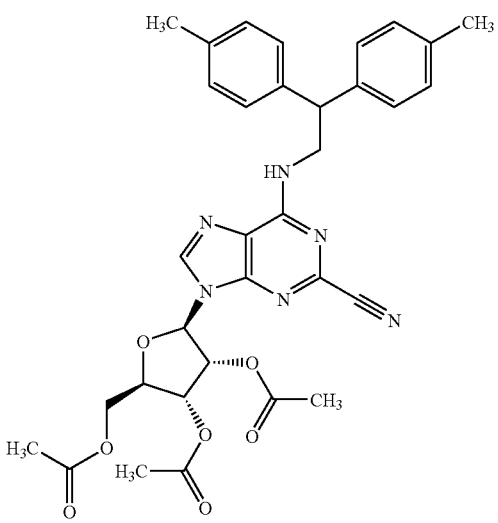

The compound was prepared from (2R,3R,4R,5R)-4-(acetyloxy)-2-[(acetyloxy)methyl]-5-(6-chloro-2-cyano-9H-purin-9-yl)tetrahydro-3-furanyl acetate (Preparation 45) and 2,2-bis(4-methylphenyl)ethanamine (J. Med. Chem., 1969, 12(1), 9) using a similar method to that of Preparation 64.

$\delta_H$ (400 MHz; CDCl$_3$): 7.95 (1H, s), 7.20–7.05 (8H, m), 6.15–6.10 (1H, m), 5.95–5.90 (1H, m), 5.75–5.70 (1H, m), 5.55–5.50 (1H, m), 4.50–4.35 (3H, m), 4.30–4.20 (2H, m), 2.30 (6H, m), 2.20–2.00 (9H, m).

Preparation 60

(2R,3R,4S,5R)-2-(2-(Aminomethyl)-6-{[2,2-bis(4-methylphenyl)ethyl]amino}-9H-purin-9-yl)-5-(hydroxymethyl)tetrahydro-3,4-furandiol

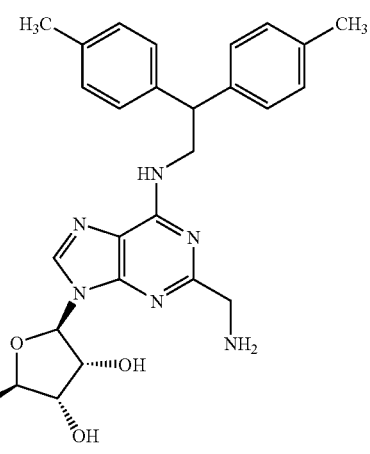

(2R,3R,4R,5R)-4-(Acetyloxy)-2-[(acetyloxy)methyl]-5-(6-{[2,2-bis(4-methylphenyl)ethyl]amino}-2-cyano-9H-purin-9-yl)tetrahydro-3-furanyl acetate (Preparation 59) (837 mg, 1.33 mmol) was dissolved in a saturated solution of ammonia in ethanol (25 ml). 10% Palladium on carbon (168 mg) was added and the suspension was stirred under an atmosphere of hydrogen (414 kPa, 60 psi) for 16 hours. The reaction mixture was filtered through Arbocel (Trade Mark) and the filtrate was evaporated under reduced pressure. The residue was dissolved in methanol (100 ml) and sodium carbonate (100 mg) was added. The suspension was stirred at room temperature for 2 hours. The solvent was removed under reduced pressure and the residue was dissolved in a mixture of dichloromethane (15 ml) and water (15 ml). The dichloromethane layer was washed with water (15 ml) and saturated aqueous sodium chloride solution. The solvent was removed under reduced pressure. The residue was triturated with diethyl ether to give the title compound as a solid (340 mg).

m/z MH$^+$ 503. $\delta_H$ (400 MHz; CDCl$_3$): 8.10 (1H, s), 7.20–7.10 (4H, m), 7.05–7.00 (4H, m), 5.90–5.85 (1H, m), 4.70–4.65 (1H, m), 4.40–4.35 (1H, m), 4.35–4.05 (3H, m), 3.85–3.80 (3H, m), 3.70–3.65 (1H, m), 2.05 (6H, m).

Preparation 61

(2R,3R,4R,5R)-4-(Acetyloxy)-2-[(acetyloxy)methyl]-5-(6-{[2,2-bis(3-chlorophenyl) ethyl]amino}-2-cyano-9H-purin-9-yl)tetrahydro-3-furanyl acetate

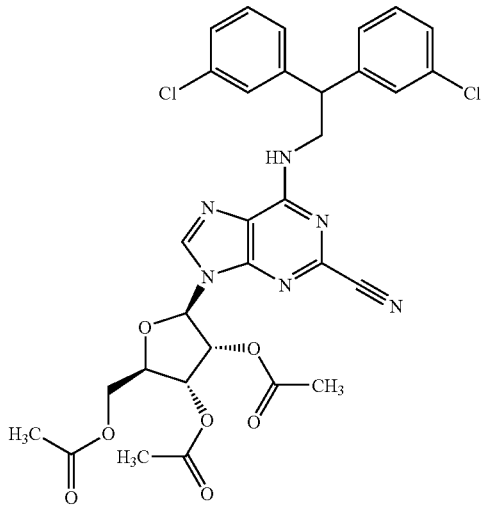

The compound was prepared from (2R,3R,4R,5R)-4-(acetyloxy)-2-[(acetyloxy)methyl]-5-(6-chloro-2-cyano-9H-purin-9-yl)tetrahydro-3-furanyl acetate (Preparation 45) and 2,2-bis(3-chlorophenyl)ethanamine (*J. Med. Chem.*, 1988, 31(7), 1282) using a similar method to that of Preparation 64.

$\delta_H$ (400 MHz; CDCl$_3$): 8.00 (1H, s), 7.30–7.10 (8H, m), 6.20–6.10 (1H, m), 5.80–5.70 (1H, m), 5.60–5.50 (1H, m), 4.50–4.30 (4H, m), 4.30–4.15 (2H, m), 2.20–2.00 (9H, m).

Preparation 62

(2R,3R,4S,5R)-2-(2-(Aminomethyl)-6-{[2,2-bis(3-chlorophenyl)ethyl]amino}-9H-purin-9-yl)-5-(hydroxymethyl)tetrahydro-3,4-furandiol

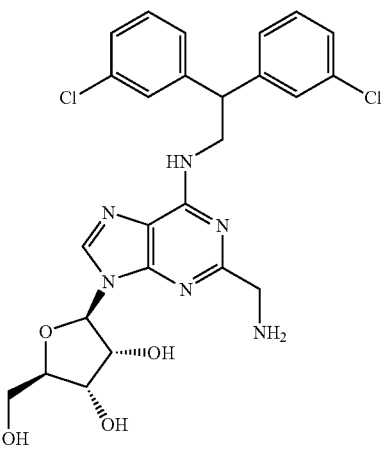

The title compound was prepared from (2R,3R,4R,5R)-4-(acetyloxy)-2-[(acetyloxy)methyl]-5-(6-{[2,2-bis(3-chlorophenyl)ethyl]amino}-2-cyano-9H-purin-9-yl)tetrahydro-3-furanyl acetate (Preparation 61) by the method used in Preparation 60.

$\delta_H$ (400 MHz; CD$_3$OD): 8.15–8.10 (1H, m), 7.35–7.10 (8H, m), 5.90–5.85 (1H, m), 4.70–4.65 (1H, m), 4.40–4.20 (3H, m), 4.10–4.05 (1H, m), 3.90–3.80 (3H, m), 3.70–3.65 (3H, m).

Preparation 63

(2R,3R,4S,5R)-2-(2-(Aminomethyl)-6-{[2,2-bis(4-chlorophenyl)ethyl]amino}-9H-purin-9-yl)-5-(hydroxymethyl)tetrahydro-3,4-furandiol

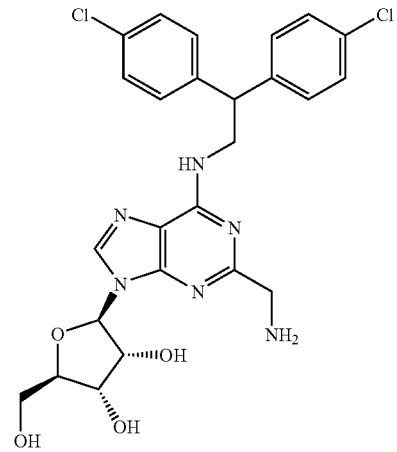

A solution of (2R,3R,4R,5R)-4-(acetyloxy)-2-[(acetyloxy)methyl]-5-(6-{[2,2-bis(4-chlorophenyl)ethyl]amino}-2-cyano-9H-purin-9-yl)tetrahydro-3-furanyl acetate (700 mg, 1 mmol) (Preparation 64) in ethanol (20 ml) was saturated with ammonia gas. 10% Palladium on carbon (140

Preparation 64

(2R,3R,4R,5R)-4-(Acetyloxy)-2-[(acetyloxy)methyl]-5-(6-{[2,2-bis(4-chlorophenyl)ethyl]amino}-2-cyano-9H-purin-9-yl)tetrahydro-3-furanyl acetate

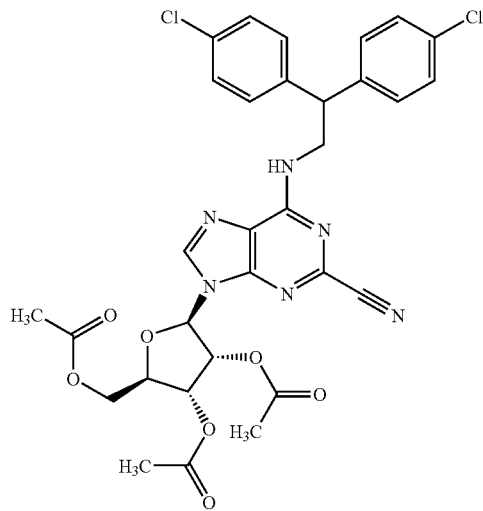

Triethylamine (0.2 ml, 1.14 mmol) was added to a stirred solution of (2R,3R,4R,5R)-4-(acetyloxy)-2-[(acetyloxy)methyl]-5-(6-chloro-2-cyano-9H-purin-9-yl)tetrahydro-3-furanyl acetate (500 mg, 1.14 mmol) (Preparation 45) and 2,2-bis(4-chlorophenyl)ethanamine (919 mg, 1.2 mmol) (J. Am. Chem. Soc., 1983, 105(10), 3138) in acetonitrile (5 ml) at room temperature. The reaction mixture was stirred for 16 hours. The solvent was then removed under reduced pressure and the residue was dissolved in dichloromethane (20 ml). The solution was washed with water (10 ml) and saturated sodium chloride solution (10 ml), dried over anhydrous magnesium sulphate and evaporated under reduced pressure. The residue was purified by column chromatography on silica gel eluting with dichloromethane:methanol:(99:1 by volume) increasing in polarity to dichloromethane:methanol (98.5:1.5 by volume). The solvent was removed under reduced pressure to give the title compound (698 mg) as a foam.

m/z MH$^+$ 667. $\delta_H$ (400 MHz; CD$_3$OD): 7.95 (1H, s), 7.35–7.10 (8H, m), 6.15–6.10 (1H, m), 5.95–5.85 (1H, m), 5.75–5.70 (1H, m), 5.55–5.50 (1H, m), 4.45–4.30 (4H, m), 4.30–4.10 (2H, m), 2.20–2.05 (9H, m).

Preparation 65

(2R,3R,4S,5R)-2-(2-(Aminomethyl)-6-{[2,2-bis(3-methylphenyl)ethyl]amino} -9H-purin-9-yl)-5-(hydroxymethyl)tetrahydro-3,4-furandiol

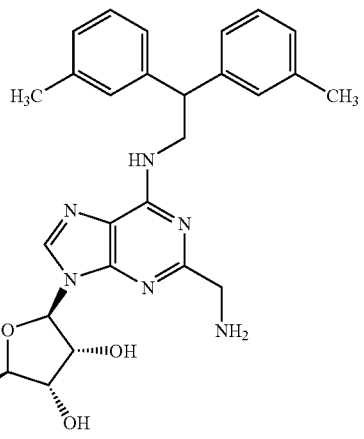

(2R,3R,4R,5R)-4-(Acetyloxy)-2-[(acetyloxy)methyl]-5-(6-{[2,2-bis(3-methylphenyl)ethyl]amino}-2-cyano-9H-purin-9-yl)tetrahydro-3-furanyl acetate (620 mg, 1 mmol) (Preparation 66) was dissolved in a saturated solution of 0.88 concentrated aqueous ammonia in ethanol (20 ml). The solution was then stirred under an atmosphere of hydrogen gas (414 kPa, 60 psi) at room temperature for 64 hours in the presence of 10% Palladium on carbon (120 mg). The reaction mixture was then filtered through Arbocel (Trade Mark) and the filtrate was evaporated to dryness. The residue was purified by column chromatography on silica gel eluting with dichloromethane:methanol:(90:10 by volume) increasing in polarity to dichloromethane:methanol:0.88 concentrated aqueous ammonia (80:20:2 by volume). The solvent was removed under reduced pressure to give the title compound (253 mg) as a foam.

m/z MH$^+$ 503. $\delta_H$ (400 MHz; CD$_3$OD): 8.10 (1H, s), 7.20–7.05 (6H, m), 7.05–6.90 (2H, m), 5.95–5.90 (1H, m), 4.70–4.65 (1H, m), 4.40–4.35 (1H, m), 4.35–4.20 (2H, m), 4.20–4.10 (1H, m), 3.90–3.80 (2H, m), 3.70–3.65 (1H, m), 2.05 (6H, m).

Preparation 66

(2R,3R,4R,5R)-4-(Acetyloxy)-2-[(acetyloxy)methyl]-5-(6-{[2,2-bis(3-methylphenyl)ethyl]amino}-2-cyano-9H-purin-9-yl)tetrahydro-3-furanyl acetate

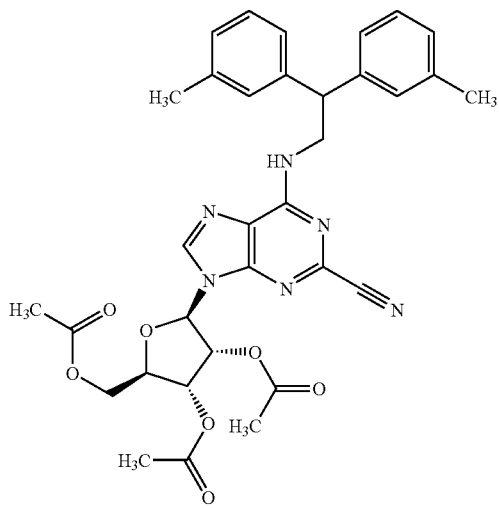

The title compound was prepared from (2R,3R,4R,5R)-4-(acetyloxy)-2-[(acetyloxy)methyl]-5-(6-chloro-2-cyano-9H-purin-9-yl)tetrahydro-3-furanyl acetate (Preparation 45) and 2,2-bis(3-methylphenyl)ethanamine (J. Med. Chem., 1988, 31(7), 1282) using a similar procedure to that of Preparation 64.

m/z MH$^+$ 627. $\delta_H$ (400 MHz; CD$_3$OD): 7.95 (1H, s), 7.25–7.15 (2H, m), 7.10–7.00 (6H, m), 6.15–6.10 (1H, m), 5.95–5.90 (1H, m), 5.80–5.70 (1H, m), 5.60–5.55 (1H, m), 4.50–4.35 (3H, m), 4.30–4.20 (3H, m), 3.30 (6H, s), 2.20–2.05 (9H, m).

Preparation 67

(2R, 3R,4 S,5S)-4-(Benzoyloxy)-2-(6-{[2, 2-bis(4-chlorophenyl)ethyl]amino}-2-iodo-9H-purin-9-yl)-5-[(ethylamino)carbonyl]tetrahydro-3-furanyl benzoate

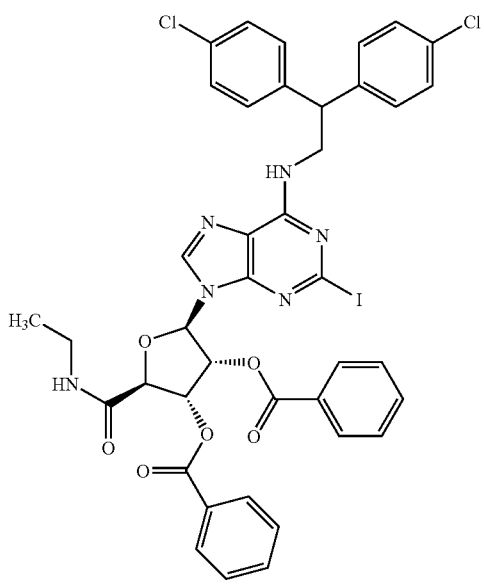

2,2-Bis(4-chlorophenyl)ethanamine (426 mg, 1.51 mmol) (J. Am. Chem. Soc., 1983, 105(10), 3138) was added to a stirred solution of (2R,3R,4S,5S)-4-(benzoyloxy)-2-(6-chloro-2-iodo-9H-purin-9-yl)-5-[(ethylamino)carbonyl]tetrahydro-3-furanyl benzoate (500 mg, 0.755 mmol) (Preparation 47) in isopropyl alcohol (20 ml) at room temperature. The reaction mixture was stirred at room temperature for 48 hours. The solvent was removed under reduced pressure to give a residue that was purified by column chromatography on silica gel eluting with dichloromethane:methanol:(99:1 by volume). The solvent was removed under reduced pressure to give the title compound (329 mg) as a foam.

m/z MH$^+$ 891. $\delta_H$ (400 MHz; CD$_3$OD): 8.10–8.00 (2H, m), 7.85–7.75 (3H, m), 7.65–7.55 (1H, m), 7.55–7.40 (4H, m), 7.30–7.15 (8H, m), 6.30–6.20 (1H, m), 6.15–6.10 (1H, m), 6.10–6.05 (1H, m), 5.85–5.75 (1H, m), 4.90 (1H, s), 4.40–4.30 (2H, m), 4.25–4.10 (2H, m), 3.75–3.60 (1H, m), 3.60–3.45 (1H, m), 1.30–1.20 (3H, m).

Preparation 68

(2R,3R,4S,5S)-4-(Benzoyloxy)-2-(6-{[2,2-bis(4-chlorophenyl)ethyl]amino}-2-cyano-9H-purin-9-yl)-5-[(ethylamino)carbonyl]tetrahydro-3-furanyl benzoate

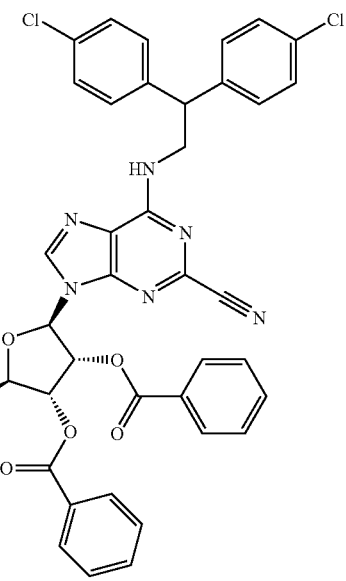

Copper(I) cyanide was added to a solution of (2R,3R,4S,5S)-4-(benzoyloxy)-2-(6-{[2,2-bis(4-chlorophenyl)ethyl]amino}-2-iodo-9H-purin-9-yl)-5-[(ethylamino)carbonyl]tetrahydro-3-furanyl benzoate (440 mg, 0.494 mmol) (Preparation 67) in N'N'-dimethylformamide (10 ml). The reaction mixture was stirred at 90° C. overnight. The reaction mixture was poured into water (15 ml). The precipitate was filtered off and stirred in dichloromethane (50 ml) for 10 minutes. The dichloromethane was filtered, dried over anhydrous magnesium sulphate and evaporated under reduced pressure. The residue was purified by column chromatography on silica gel eluting with dichloromethane:methanol (98: 2 by volume). The solvent was removed under reduced pressure to give the title compound (227 mg) as a foam.

$\delta_H$ (400 MHz; CD$_3$OD): 8.20 (1H, m), 8.10–8.00 (3H, m), 7.85–7.75 (2H, m), 7.65–7.60 (1H, m), 7.60–7.40 (4H, m), 7.35–7.15 (8H, m), 6.40–6.35 (1H, m), 6.30–6.20 (1H, m), 6.10–6.00 (2H, m), 4.90 (1H, m), 4.45–4.35 (1H, m), 4.30–4.15 (2H, m), 3.65–3.45 (2H, m), 1.30–1.20 (3H, m).

Preparation 69

(2S,3S,4R,5R)-5-{2-(Aminomethyl)-6-[(1-naphthylmethyl)amino]-9H-purin-9-yl}-N-ethyl-3,4-dihydroxytetrahydro-2-furancarboxamide

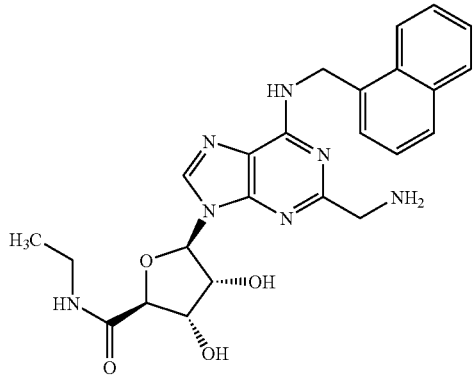

10% Palladium on carbon was added to a solution of (2R,3R,4S,5S)-4-(benzoyloxy)-2-{2-cyano-6-[(1-naphthylmethyl)amino]-9H-purin-9-yl}-5-[(ethylamino)carbonyl]tetrahydro-3-furanyl benzoate (487 mg, 0.71 mmol) (Preparation 70) dissolved in a saturated solution of ammonia in ethanol. The reaction mixture was stirred for 16 hours under an atmosphere of hydrogen gas (414 kPa, 60 psi). The reaction mixture was then filtered through Arbocel (Trade Mark) and the solvent was removed under reduced pressure. The residue was purified by column chromatography on silica gel eluting with dichloromethane:methanol:0.88 concentrated aqueous ammonia (95:5:0.5 by volume) increasing in polarity to dichloromethane:methanol:0.88 concentrated aqueous ammonia (80:20:2 by volume). The solvent was removed under reduced pressure to give the title compound (240 mg) as a foam.

$\delta_H$ (400 MHz; D$_6$DMSO): 8.45–8.20 (4H, m), 7.90–7.85 (1H, m), 7.80–7.75 (1H, m), 7.55–7.45 (3H, m), 7.45–7.35 (1H, m), 5.95–5.90 (1H, m), 5.65–5.55 (1H, m), 5.55–5.45 (1H, m), 5.20–5.10 (2H, m), 4.65–4.55 (1H, m), 4.25 (1H, s), 4.15–4.10 (1H, m), 4.10–3.90 (1H, m), 3.65 (2H, m), 3.20–3.00 (2H, m), 1.05–0.90 (3H, m).

Preparation 70

(2R,3R,4S,5S)-4-(Benzoyloxy)-2-(2-cyano-6-[(1-naphthylmethyl)amino]-9H-purin-9-yl}-5-[(ethylamino)carbonyl]tetrahydro-3-furanyl benzoate

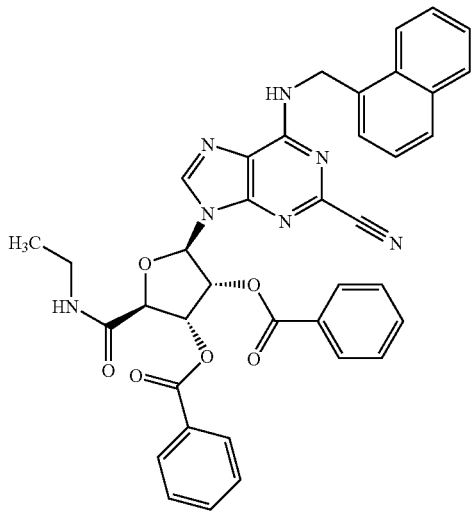

Diazabicycloundecane (0.18 ml, 1.2 mmol) was added to a solution of (6-[(1-naphthylmethyl)amino]-9H-purine-2-carbonitrile (200 mg, 0.67 mmol) (Preparation 10) and (2S,3S,4R,5R)-5-(acetyloxy)-4-(benzoyloxy)-2-[(ethylamino)carbonyl]tetrahydro-3-furanyl benzoate and (2S,3S,4R,5S)-5-(acetyloxy)-4-(benzoyloxy)-2-[(ethylamino)carbonyl]tetrahydro-3-furanyl benzoate (309 mg, 0.70 mmol) (Preparation 18) in acetonitrile (5 ml). Trimethylsilyl trifluoromethanesulfonate (0.24 ml, 1.33 mmol) was added and the reaction mixture heated under reflux for 30 minutes. The reaction mixture was then allowed to cool to room temperature, diluted with ethyl acetate (20 ml) and washed twice with water (20 ml). The ethyl acetate layer was then washed with 10% w/w aqueous citric acid and saturated aqueous sodium chloride solution (20 ml). The organic phase was dried over anhydrous magnesium sulphate and evaporated under reduced pressure. The residue was purified by column chromatography on silica gel eluting with dichloromethane increasing in polarity to dichloromethane:methanol (98:2 by volume). The solvent was removed under reduced pressure to give the title compound (235 mg) as a foam.

$\delta_H$ (400 MHz; d$_6$DMSO): 9.20–9.10 (1H, m), 8.75 (1H, m), 8.30–8.20 (2H, m), 8.00–7.90 (3H, m), 7.80–7.70 (3H, m), 7.70–7.60 (1H, m), 7.60–7.30 (8H, m), 6.70–6.60 (1H, m), 6.30–6.20 (1H, m), 6.10–6.05 (1H, m), 5.15–5.10 (2H, m), 4.90–4.85 (1H, m), 3.20–3.05 (2H, m), 1.00–0.90 (3H, m).

Preparation 71

(2R,3R,4R,5R)-4-(Acetyloxy)-2-[(acetyloxy)methyl]-5-{2-cyano-6-[(9H-fluoren-9-ylmethyl)amino]-9H-purin-9-yl}tetrahydro-3-furanyl acetate

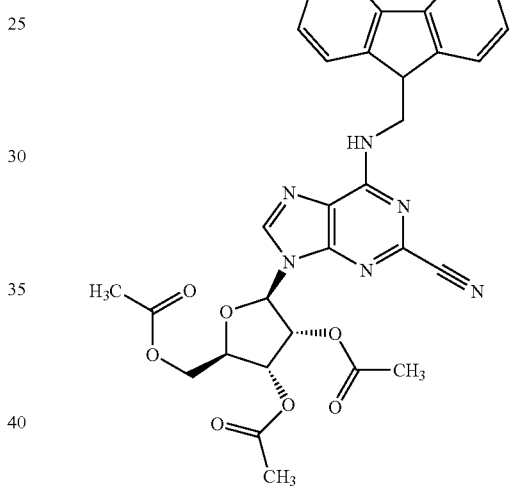

Triethylamine (0.38 ml, 2.7 mmol) was added to a stirred solution of (2R,3R,4R,5R)-4-(acetyloxy)-2-[(acetyloxy)methyl]-5-(6-chloro-2-cyano-9H-purin-9-yl)tetrahydro-3-furanyl acetate (1.0 g, 2.3 mmol) (Preparation 45) and 9H-fluoren-9-ylmethanamine (0.49 g, 2.5 mmol) (J. Org. Chem., 1971, 36(23), 3539) in acetonitrile (30 ml) at room temperature. The reaction mixture was stirred at room temperature for 16 hours. The solvent was removed under reduced pressure. The residue was partially redissoved in ethyl acetate (30 ml). The ethyl acetate was washed with water (1 ml) and a saturated aqueous sodium chloride solution (10 ml). The organic phase was evaporated under reduced pressure and the residue was purified by column chromatography on silica gel eluting with dichloromethane: ethyl acetate (96:4 by volume) increasing in polarity to dichloromethane: ethyl acetate (94:6 by volume). The solvent was removed under reduced pressure to give the title compound (1.23 g) as a foam.

m/z MH$^+$ 595. $\delta_H$ (300 MHz; CDCl$_3$): 8.00 (1H, s), 7.80–7.75 (2H, m), 7.65–7.60 (2H, m), 7.45–7.30 (4H, m), 6.20–6.10 (1H, m), 6.05–5.95 (1H, m), 5.80–5.75 (1H, m), 5.60–5.55 (1H, m), 4.50–4.30 (4H, m), 4.30–4.20 (2H, m), 2.20–2.05 (9H, m).

Preparation 72

(2S,3S,4R,5R)-5-{6-[(2,2-Diphenylethyl)amino]-2-[(methylamino)methyl]-9H-purin-9-yl}-N-ethyl-3,4-dihydroxytetrahydro-2-furancarboxamide

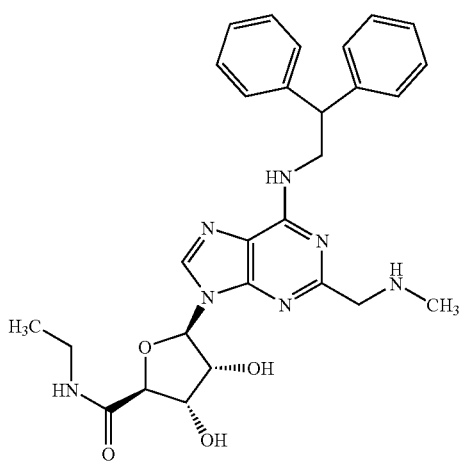

10% Palladium on carbon (0.2 g) was added to a solution of (2S,3R,4R,5R)-4-(benzoyloxy)-5-{2-cyano-6-[(2,2-diphenylethyl)amino]-9H-purin-9-yl}-2-[(ethylamino)carbonyl]tetrahydro-3-furanyl benzoate (1.0 g, 1.4 mmol) (Preparation 7) in 33% w/w methylamine in ethanol (75 ml). The reaction mixture was stirred under an atmosphere of hydrogen gas (4414 kPa, 60 psi) for 16 hours at room temperature. The solid was filtered off and the solvent was removed from the filtrate under reduced pressure. The residue was purified by flash chromatography on silica gel eluting with dichloromethane:methanol:0.88 concentrated aqueous ammonia (95:5:0.5 by volume) increasing in polarity to dichloromethane:methanol:0.88 concentrated aqueous ammonia (90:10:1 by volume) to give the title compound (0.52 g) as a solid.

m/z MH$^+$ 532. $\delta_H$ (400 MHz; CDCl$_3$): 8.25 (1H, s), 7.35–7.20 (8H, m), 7.20–7.10 (2H, m), 6.05–6.00 (1H, m), 4.55–4.45 (1H, m), 4.45 (2H, m), 4.40–4.20 (2H, m), 3.80 (2H, m), 3.40–3.20 (2H, m), 2.45 (3H, m), 1.15–1.05 (3H, m).

Preparation 73

N-[2-(1-Piperidinyl)ethyl]-1H-imidazole-1-carboxamide

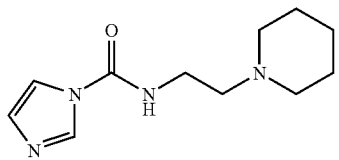

2-(1-Piperidinyl)ethylamine (1.28 g, 10 mmol) was added to a stirred solution of N,N'-carbonyldiimidazole (1.62 g, 10 mmol) in THF (25 ml) at room temperature. The reaction mixture was stirred overnight and the solvent was then removed by evaporation under reduced pressure. The residue was partitioned between ethyl acetate (100 ml) and water (50 ml) and the ethyl acetate layer was separated, washed with brine (30 ml) and dried with anhydrous sodium sulphate. Evaporation of the solvent under reduced pressure yielded the title compound as a white solid (1.8 g).

$\delta_H$ (400 MHz; CDCl$_3$): 8.10 (1H, s), 7.35 (1H, s), 7.10 (1H, s), 6.80 (1H, br s), 3.45 (2H, m), 2.55 (2H, m), 2.50–2.30 (4H, m), 1.60–1.40 (6H, m).

PHARMACOLOGICAL ACTIVITY

All of the compounds of the Examples were tested for anti-inflammatory activity by their ability to inhibit neutrophil function (which indicates A2a receptor agonist activity) by the method described on page 31 and all had an IC$_{50}$ of less than 1 micromolar.

We claim:

1. A method of treating respiratory disease in a mammal comprising administering to a mammal in need of such treatment
   (a) a compound of formula (I)

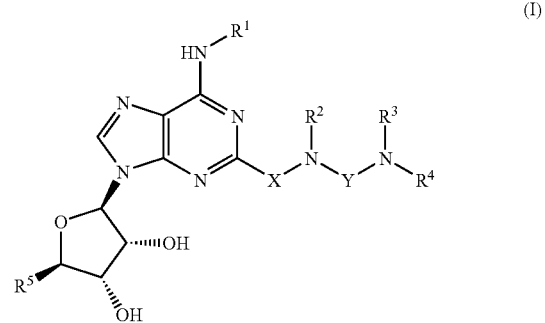

or a pharmaceutically acceptable salt or solvate thereof, wherein

R$^1$ is (i) H, (ii) C$_1$–C$_6$ alkyl optionally substituted by 1 or 2 substituents each independently selected from phenyl, naphthyl and fluorenyl, said phenyl, naphthyl and fluorenyl being optionally substituted by C$_1$–C$_6$ alkyl, C$_1$–C$_6$ alkoxy, halo or cyano, or (iii) fluorenyl;

R$^2$ is H or C$_1$–C$_6$ alkyl; either, R$^3$ and R$^4$, taken together with the nitrogen atom to which they are attached, represent azetidinyl, pyrrolidinyl, piperidinyl, piperazinyl, homopiperidinyl or homopiperazinyl, each being optionally substituted on a ring nitrogen or carbon atom by C$_1$–C$_6$ alkyl or C$_3$–C$_8$ cycloalkyl and optionally substituted on a ring carbon atom not adjacent to a ring nitrogen atom by —NR$^6$R$^7$ or —OR$^9$, or, R$^3$ is H, C$_1$–C$_6$ alkyl, C$_3$–C$_8$ cycloalkyl or benzyl, said C$_1$–C$_6$ alkyl being optionally substituted by C$_3$–C$_8$ cycloalkyl, and R$^4$ is (a) C$_1$–C$_6$ alkyl, C$_3$–C$_8$ cycloalkyl or R$^{15}$, said C$_1$–C$_6$ alkyl being optionally substituted by R$^{15}$; or (b) —(C$_2$–C$_6$ alkylene)-R$^8$, or (c) —(C$_1$–C$_6$ alkylene)-R$^{13}$;

R$^5$ is —CH$_2$OH or —CONHR$^{14}$;

R$^6$ and R$^7$ are either each independently H or C$_1$–C$_6$ alkyl or, taken together with the nitrogen atom to which they are attached, represent azetidinyl, pyrrolidinyl or piperidinyl, said azetidinyl, pyrrolidinyl and piperidinyl being optionally substituted by C$_1$–C$_6$ alkyl;

R$^8$ is (i) azetidin-1-yl, pyrrolidin-1-yl, piperjdin-1-yl, morpholin-4-yl, piperazin-1-yl, homopiperidin-1-yl, homopiperazin-1-yl ortetrahydroisoquinolin-1-yl, each being optionally substituted on a ring carbon atom by $C_1$–$C_6$ alkyl, $C_3$–$C_8$ cycloalkyl, phenyl, $C_1$–$C_6$ alkoxy-($C_1$–$C_6$)-alkyl, $R^9R^9N$—($C_1$–$C_6$)-alkyl, fluoro-($C_1$–$C_6$)-alkyl, —$CONR^9R^9$, —$COOR9$ or $C_2$–$C_5$ alkanoyl, optionally substituted on a ring carbon atom not adjacent to a ring nitrogen atom by fluoro-($C_1$–$C_6$)-alkoxy, halo, —$OR^9$, cyano, —$S(O)_mR^{10}$, —$NR^9R^9$, —$SO_2NR^9R^9$, —$NR^9COR^{10}$ or —$NR^9SO_2R^{10}$ and optionally benzo-fused, and said piperazin-1-yl and homopiperazin-1-yl being optionally substituted on the ring nitrogen atom not attached to the $C_2$–$C_6$ alkylene group by $C_1$–$C_6$ alkyl, phenyl, $C_1$–$C_6$ alkoxy-($C_2$–$C_6$)-alkyl, $R^9R^9N$—($C_2$–$C_6$)-alkyl, fluoro-($C_1$–$C_6$)-alkyl, $C_2$–$C_5$ alkanoyl, —$COOR^{10}$, $C_3C_8$ cycloalkyl, —$SO_2R^{10}$, —$SO_2NR^9R^9$ or —$CONR^9R^9$, or (ii) —$NR^{11}R^{12}$;

$R^9$ is H, $C_1$–$C_6$ alkyl, $C_3$–$C_8$ cycloalkyl or phenyl;

$R^{10}$ is $C_1$–$C_6$ alkyl, $C_3$–$C_8$ cycloalkyl or phenyl;

$R^{11}$ is $C_1$–$C_6$ alkyl, $C_3$–$C_8$ cycloalkyl or benzyl;

$R^{12}$ is $C_1$–$C_6$ alkyl, $C_3$–$C_8$ cycloalkyl, phenyl, benzyl, fluoro-($C_1$–$C_6$)-alkyl, —$CONR_9R_9$, —$COOR_{10}$, —$COR_{10}$, —$SO2R^{10}$ or —$SO_2NR^9 R^9$, said $C_1$–$C_6$ alky being optionally substituted by phenyl;

$R^{13}$ is phenyl, pyridin-2-yl, pyridin-3-yl or pyridin-4-yl, each being optionally substituted by $C_1$–$C_6$ alkyl, $C_1$–$C_6$ alkoxy, halo or cyano;

$R^{14}$ is H or $C_1$–$C_6$ alkyl optionally substituted by cyclopropyl;

$R^{15}$ is azetidin-3-yl, pyrrolidin-3-yl, piperidin-3-yl, piperidin-4-yl, homopiperidin-3-yl or homopiperidin-4-yl, each being optionally substituted by $R^{13}$, $C_1$–$C_6$ alkyl, $C_3$–$C_8$ cycloalkyl or benzyl;

m is 0, 1 or 2;

X is —$CH_2$— or —$CH_2CH_2$—; and

Y is CO, CS, $SO_2$ or C=N(CN); or (b) a pharmaceutical composition comprising a compound of formula (I), or a pharmaceutically acceptable salt or solvate thereof, and a pharmaceutically acceptable carrier, vehicle, or diluent.

2. The method of claim 1 wherein the disease is adult respiratory distress syndrome (ARDS), bronchitis, chronic bronchitis, chronic obstructive pulmonary disease, cystic fibrosis, asthma, emphysema, bronchiectasis, chronic sinusitis or rhinitis.

3. A method of treating inflammation in a mammal s comprising administering to a mammal in need of such treatment:

(a) a compound of formula (I)

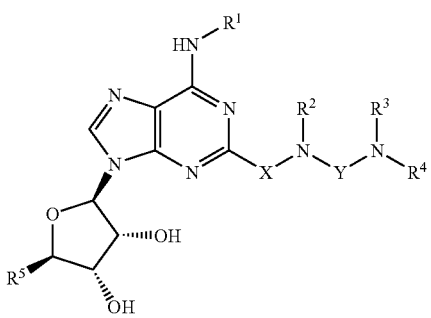

(I)

or a pharmaceutically acceptable salt or solvate thereof, wherein $R^1$ is (i) H, (ii) $C_1$–$C_6$ alkyl optionally substituted by 1 or 2 substituents each independently selected from phenyl, naphthyl and fluorenyl, said phenyl, naphthyl and fluorenyl being optionally substituted by $C_1$–$C_6$ alkyl, $C_1$–$C_6$ alkoxy, halo or cyano, or (iii) fluorenyl;

$R^2$ is H or $C_1$–$C_6$ alkyl; either, R and $R^4$, taken together with the nitrogen atom to which they are attached, represent azetidinyl, pyrrolidinyl, piperidinyl, piperazinyl, homopiperidinyl or homopiperazinyl, each being optionally substituted on a ring nitrogen or carbon atom by $C_1$–$C_6$ alkyl or $C_3$–$C_8$ cycloalkyl and optionally substituted on a ring carbon atom not adjacent to a ring nitrogen atom by —$NR^6R^7$ or —$OR^9$, or, $R^3$ is H, $C_1$–$C_6$ alkyl, $C_3$–$C_8$ cycloalkyl or benzyl, said $C_1$–$C_6$ alkyl being optionally substituted by $C_3$–$C_8$ cycloalkyl, and $R^4$ is (a) $C_1$–$C_6$ alkyl, $C_3$–$C_8$ cycloalkyl or $R^{15}$, said $C_1$–$C_6$ alkyl being optionally substituted by $R^{15}$; or (b) —($C_2$–$C_6$ alkylene)-$R^8$, or (c) —($C_1$–$C_6$ alkylene)-$R^{13}$;

$R^5$ is —$CH_2OH$ or —$CONHR^{14}$;

$R^6$ and $R^7$ are either each independently H or $C_1$–$C_6$ alkyl or, taken together with the nitrogen atom to which they are attached, represent azetidinyl, pyrrolidinyl or piperidinyl, said azetidinyl, pyrrolidinyl and piperidinyl being optionally substituted by $C_1$–$C_6$ alkyl;

$R^8$ is (i) azetidin-1-yl, pyrrolidin-1-yl, piperidin-1-yl, morpholin-4-yl, piperazin-1-yl, homopiperidin-1-yl, homopiperazin-1-yl ortetrahydroisoquinolin-1-yl, each being optionally substituted on a ring carfbon atom by $C_1$–$C_6$ alkyl, $C_3$–$C_8$ cycloalkyl, phenyl, $C_1$–$C_6$ alkoxy-($C_1$–$C_6$) alkyl, $R^9R^9N$—($C_1$–$C_6$)-alkyl, fluoro-($C_1$–$C_6$)-alkyl, —$CONR^9R^9$, —$COOR^9$ or $C_2$–$C_5$ alkanoyl, optionally substituted on a ring carbon atom not adjacent to a ring nitrogen atom by fluoro-($C_1$–$C_6$)-alkoxy, halo, —$OR^9$, cyano, —$S(O)_mR^{10}$, —$NR^9R_9$, —$SO_2NR^9R^9$, —$NR^9COR^{10}$ or —$NR^9SO_2R^{10}$ and optionally benzo-fused, and said piperazin-1-yl and homopiperazin-1-yl being optionally substituted on the ring nitrogen atom not attached to the $C_2$–$C_6$ alkylene group by $C_1$–$C_6$ alkyl, phenyl, $C_1$–$C_6$ alkoxy-($C_2$–$C_6$)-alkyl, $R^9R^9N$-($C_2$–$C_6$)-alkyl, fluoro-($C_1$–$C_6$)-alkyl, $C_2$–$C_5$ alkanoyl, —$COOR^{10}$, $C_3$–$C_6$ cycloalkyl, —$SO_2R^{10}$, —$SO_2NR^9R^9$ or —$CONR^9R^9$, or (ii) —$NR^{11}R^{12}$;

$R^9$ is H, $C_1$–$C_6$ alkyl, $C_3$–$C_8$ cycloalkyl or phenyl;

$R^{10}$ is $C_1$–$C_6$ alkyl, $C_3$–$C_8$ cycloalkyl or phenyl;

$R^{11}$ is $C_1$–$C_6$ alkyl, $C_3$–$C_8$ cycloalkyl or benzyl;

$R^{12}$ is $C_1$–$C_6$ alkyl, $C_3$–$C_8$ cycloalkyl, phenyl, benzyl, fluoro-($C_1$–$C_6$)-alkyl, —$CONR^9R^9$, —$COOR^{10}$, —$COR^{10}$, —$SO_2R^{10}$ or —$SO_2NR^9R^9$, said $C_1$–$C_6$ alkyl being optionally substituted be phenyl;

$R^{13}$ is phenyl, pyridin-2-yl, pyridin-3-yl or pyridin-4-yl, each being optionally substituted by $C_1$–$C_6$ alkyl, $C_1$–$C_6$ alkoxy, halo or cyano;

$R^{14}$ is H or $C_1$–$C_6$ alkyl optionally substituted by cyclopropyl;

$R^{15}$ is azetidin-3-yl, pyrrolidin-3-yl, piperidin-3-yl, piperidin-4-yl, homopiperidin-3-yl or homopiperidin-4-yl, each being optionally substituted by $R^{13}$, $C_1$–$C_6$ alkyl, $C_3$–$C_8$ cycloalkyl or benzyl;

m is 0, 1 or 2;

X is —$CH_2$—or —$CH_2CH_2$—; and

Y is CO, CS, $SO_2$ or C=N(CN); or (b) a pharmaceutical composition comprising a compound of formula (I), or a pharmaceutically acceptable salt or solvate thereof, and a pharmaceutically acceptable carrier, vehicle, or diluent.

4. A method of treating septic shock, male erectile dysfunction, hypertension, stroke, epilepsy, cerebral ischaemia, peripheral vascular disease, postischaemic reperfusion injury, diabetes, rheumatoid arthritis, multiple sclerosis, psoriasis, allergic dermatitis, eczema, ulcerative colitis, Crohns disease, inflammatory bowel disease, *Heliobacter pylori*-gastritis, non-Heliobacter pylori gastritis, non-steroidal anti-inflammatory drug-induced damage to the gastrointestinal tract or a psychotic disorder, or promoting wound healing in a mammal comprising administering to a mammal in need of such treatment:

(a) a compound of formula (I)

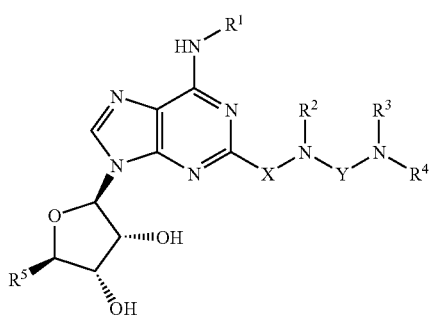

or a pharmaceutically acceptable salt or solvate thereof, wherein $R^1$ is (i) H, (ii) $C_1$–$C_6$ alkyl optionally substituted by 1 or 2 substituents each independently selected from phenyl, naphthyl and fluorenyl, said phenyl, naphthyl and fluorenyl being optionally substituted by $C_1$–$C_6$ alkyl, $C_1$–$C_6$ alkoxy, halo or cyano, or (iii) fluorenyl;

$R^2$ is H or $C_1$–$C_6$ alkyl;

either, $R^3$ and $R^4$, taken together with the nitrogen atom to which they are attached, represent azetidinyl, pyrrolidinyl, piperidinyl, piperazinyl, homopiperidinyl or homopiperazinyl, each being optionally substituted on a ring nitrogen or carbon atom by $C_1$–$C_6$ alkyl or $C_3$–$C_8$ cycloalkyl and optionally substituted on a ring carbon atom not adjacent to a ring nitrogen atom by —$NR^6R^7$ or —$OR^9$, or, $R^3$ is H, $C_1$–$C_6$ alkyl, $C_3$–$C_8$ cycloalkyl or benzyl, said $C_1$–$C_6$ alkyl being optionally substituted by $C_3$–$C_8$ cycloalkyl, and $R^4$ is (a) $C_1$–$C_6$ alkyl, $C_3$–$C_8$ cycloalkyl or $R^{15}$, said $C_1$–$C_6$ alkyl being optionally substituted by $R^{15}$; or (b) —($C_2$–$C_6$ alkylene)-$R^8$, or (c) —($C_1$–$C_6$ alkylene)-$R^{13}$;

$R^5$ is —$CH_2OH$ or —$CONHR^{14}$;

$R^6$ and $R^7$ are either each independently H or $C_1$–$C_6$ alkyl or, taken together with the nitrogen atom to which they are attached, represent azetidinyl, pyrrolidinyl or piperidinyl, said azetidinyl, pyrrolidinyl and piperidinyl being optionally substituted by $C_1$–$C_6$ alkyl;

$R^8$ is (i) azetidin-1-yl, pyrrolidin-1-yl, piperidin-1-yl, morpholin-4-yl, piperazin-1-yl, homopiperidin-1-yl, homopiperazin-1-yl ortetrahydroisoquinolin-1-yl, each being optionally substituted on a ring carbon atom by $C_1$–$C_6$ alkyl, $C_3$–$C_8$ cycloalkyl, phenyl, $C_1$–$C_6$ alkoxy-($C_1$–$C_6$)-alkyl, $R^9R^9N$-($C_1$–$C_6$)-alkyl, fluoro-($C_1$–$C_6$)-alkyl, —$CONR^9R^9$, —$COOR^9$ or $C_2$–$C_5$ alkanoyl, optionally substituted on a ring carbon atom not adjacent to a ring nitrogen atom by fluoro-($C_1$–$C_6$)-alkoxy, halo, —$OR^9$, cyano, —$S(O)_mR^{10}$, —$NR^9R^9$, —$SO_2NR^9R^9$, —$NR^9COR^{10}$ or —$NR^9SO_2R^{10}$ and optionally benzo-fused, and said piperazin-1-yl and homopiperazin-1-yl being optionally substituted on the ring nitrogen atom not attached to the $C_2$–$C_6$ alkylene group by $C_1$–$C_6$ alkyl, phenyl, $C_1$–$C_6$ alkoxy-($C_2$–$C_6$)-alkyl, $R^9R^9N$—($C_2$–$C_6$)-alkyl, fluoro-($C_1$–$C_6$)-alkyl, $C_2$–$C_5$ alkanoyl, —$COOR^{10}$, $C_3$–$C_8$ cycloalkyl, —$SO_2R^{10}$, —$SO_2NR^9R^9$ or —$CONR^9R^9$, or (ii)—$NR^{11}R^{12}$;

$R^9$ is H, $C_1$–$C_6$ alkyl, $C_3$–$C_8$ cycloalkyl or phenyl;

$R^{10}$ is $C_1$–$C_6$ alkyl, $C_3$–$C_8$ cycloalkyl or phenyl;

$R^{11}$ is $C_1$–$C_6$ alkyl, $C_3$–$C_8$ cycloalkyl or benzyl;

$R^{12}$ is $C_1$–$C_6$ alkyl, C3–C8 cycloalkyl, phenyl, benzyl, fluoro-($C_1$–$C_6$)-alkyl, —$CONR^9R^9$, —$COOR^{10}$, —$COR^{10}$, —$SO_2NR^9R^9$ or —$SO_2NR^9R^9$, said $C_1$–$C_6$ alkyl being optionally substituted by phenyl;

$R^{13}$ is phenyl, pyridin-2-yl, pyridin-3-yl or pyridin-4-yl, each being optionally substituted by $C_1$–$C_6$ alkyl, $C_1$–$C_6$ alkoxy, halo or cyano;

$R^{14}$ is H or $C_1$–$C_6$ alkyl optionally substituted by cyclopropyl;

$R^{15}$ is azetidin-3-yl, pyrrolidin-3-yl, piperidin-3-yl, piperidin-4-yl, homopiperidin-3-yl or homopiperidin-4-yl, each being optionally substituted by $R^{13}$, $C_1$–$C_6$ alkyl, $C_3$–$C_8$ cycloalkyl or benzyl;

m is 0, 1 or 2;

X is —$CH_2$— or —$CH_2CH_2$—; and

Y is CO, CS, $SO_2$ or C=N(CN); or (b) a pharmaceutical composition comprising a compound of formula (I), or a pharmaceutically acceptable salt or solvate thereof, and a pharmaceutically acceptable carrier, vehicle, or diluent.

* * * * *